United States Patent
Hong et al.

(10) Patent No.: US 10,328,428 B2
(45) Date of Patent: Jun. 25, 2019

(54) APPARATUS FOR PREPARING CDNA LIBRARIES FROM SINGLE CELLS

(71) Applicant: California Institute of Technology, Pasadena, CA (US)

(72) Inventors: Jong Wook Hong, Seoul (KR); Vincent Studer, Paris (FR); W. French Anderson, Chino, CA (US); Stephen R. Quake, Stanford, CA (US); Jared Leadbetter, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 141 days.

(21) Appl. No.: 15/406,451

(22) Filed: Jan. 13, 2017

(65) Prior Publication Data

US 2019/0009272 A1 Jan. 10, 2019

Related U.S. Application Data

(63) Continuation of application No. 14/494,284, filed on Sep. 23, 2014, now Pat. No. 9,579,650, which is a continuation of application No. 10/678,946, filed on Oct. 2, 2003, now Pat. No. 8,871,446.

(60) Provisional application No. 60/494,377, filed on Aug. 11, 2003, provisional application No. 60/494,388, filed on Aug. 11, 2003, provisional application No. 60/444,022, filed on Jan. 31, 2003, provisional application No. 60/415,407, filed on Oct. 2, 2002.

(51) Int. Cl.
| | | |
|---|---|---|
| *C12Q 1/68* | (2018.01) | |
| *B01L 3/00* | (2006.01) | |
| *C12Q 1/6806* | (2018.01) | |

(52) U.S. Cl.
CPC ..... *B01L 3/502715* (2013.01); *B01L 3/50273* (2013.01); *B01L 3/502738* (2013.01); *B01L 3/502761* (2013.01); *C12Q 1/6806* (2013.01); *B01L 2200/10* (2013.01); *B01L 2300/0809* (2013.01); *B01L 2300/0816* (2013.01); *B01L 2300/0877* (2013.01); *B01L 2300/1827* (2013.01); *B01L 2400/0481* (2013.01); *B01L 2400/0655* (2013.01)

(58) Field of Classification Search
CPC ........... B01L 3/502715; B01L 2200/10; B01L 2300/0877; C12M 3/00
See application file for complete search history.

(56) References Cited

U.S. PATENT DOCUMENTS

| | | |
|---|---|---|
| 2,656,508 A | 10/1953 | Coulter |
| 3,403,698 A | 10/1968 | Klun |
| 3,560,754 A | 2/1971 | Kamentsky |
| 3,570,515 A | 3/1971 | Kinner |
| 3,599,525 A | 8/1971 | Klann |
| 3,747,628 A | 7/1973 | Holster et al. |
| 3,839,176 A | 10/1974 | McCoy et al. |
| 3,915,652 A | 10/1975 | Natelson |
| 3,984,307 A | 10/1976 | Kamentsky et al. |
| 4,018,565 A | 4/1977 | Fletcher, III et al. |
| 4,046,159 A | 9/1977 | Pegourie |
| 4,119,368 A | 10/1978 | Yamakazi |
| 4,153,855 A | 5/1979 | Feingold |
| 4,245,673 A | 1/1981 | Bouteille et al. |
| 4,250,929 A | 2/1981 | Andreev et al. |
| 4,344,064 A | 8/1982 | Bitler et al. |
| 4,373,527 A | 2/1983 | Fischell |
| 4,399,219 A | 8/1983 | Weaver |
| 4,434,704 A | 3/1984 | Surjaatmadja |
| 4,575,681 A | 3/1986 | Grosso et al. |
| 4,581,624 A | 4/1986 | O'Connor |
| 4,585,209 A | 4/1986 | Aine et al. |
| 4,662,710 A | 5/1987 | ten Berge |
| 4,675,300 A | 6/1987 | Zare et al. |
| 4,707,237 A | 11/1987 | Lepp et al. |
| 4,786,165 A | 11/1988 | Yamamoto et al. |
| 4,797,842 A | 1/1989 | Nackman et al. |
| 4,853,336 A | 8/1989 | Saros et al. |
| 4,876,504 A | 10/1989 | Blake et al. |
| 4,898,582 A | 2/1990 | Faste |
| 4,908,112 A | 3/1990 | Pace |

(Continued)

FOREIGN PATENT DOCUMENTS

| | | |
|---|---|---|
| EP | 0 579 997 A1 | 1/1994 |
| EP | 0 592 094 A2 | 4/1994 |

(Continued)

OTHER PUBLICATIONS

"The Liver Chip," Technology Review, pp. 64-67, Mar. 2003.

(Continued)

*Primary Examiner* — David C Thomas
(74) *Attorney, Agent, or Firm* — Kilpatrick Townsend & Stockton LLP

(57) ABSTRACT

Nucleic acid from cells and viruses sampled from a variety of environments may purified and expressed utilizing microfluidic techniques. In accordance with one embodiment of the present invention, individual or small groups of cells or viruses may be isolated in microfluidic chambers by dilution, sorting, and/or segmentation. The isolated cells or viruses may be lysed directly in the microfluidic chamber, and the resulting nucleic acid purified by exposure to affinity beads. Subsequent elution of the purified nucleic acid may be followed by ligation and cell transformation, all within the same microfluidic chip. In one specific application, cell isolation, lysis, and nucleic acid purification may be performed utilizing a highly parallelized microfluidic architecture to construct gDNA and cDNA libraries.

20 Claims, 46 Drawing Sheets

Specification includes a Sequence Listing.

(56) References Cited

U.S. PATENT DOCUMENTS

| | | |
|---|---|---|
| 4,936,465 A | 6/1990 | Zold |
| 4,963,498 A | 10/1990 | Hillman et al. |
| 4,965,743 A | 10/1990 | Malin et al. |
| 4,992,312 A | 2/1991 | Frisch |
| 5,032,381 A | 7/1991 | Bronstein et al. |
| 5,085,562 A | 2/1992 | Van Lintel |
| 5,088,515 A | 2/1992 | Kamen |
| 5,091,652 A | 2/1992 | Mathies et al. |
| 5,096,388 A | 3/1992 | Weinberg |
| 5,100,627 A | 3/1992 | Buican et al. |
| 5,126,022 A | 6/1992 | Soane et al. |
| 5,126,115 A | 6/1992 | Fujita et al. |
| 5,140,161 A | 8/1992 | Hillman et al. |
| 5,143,854 A | 9/1992 | Pirrung et al. |
| 5,164,558 A | 11/1992 | Huff et al. |
| 5,164,598 A | 11/1992 | Hillman et al. |
| 5,171,132 A | 12/1992 | Miyazaki |
| 5,171,764 A | 12/1992 | Katayama et al. |
| 5,224,843 A | 7/1993 | Van Lintel |
| 5,259,737 A | 11/1993 | Kamisuki et al. |
| 5,265,327 A | 11/1993 | Faris et al. |
| 5,271,724 A | 12/1993 | van Lintel |
| 5,290,240 A | 3/1994 | Horres, Jr. |
| 5,304,487 A | 4/1994 | Wilding et al. |
| 5,307,186 A | 4/1994 | Izumi et al. |
| 5,336,062 A | 8/1994 | Richter |
| 5,346,372 A | 9/1994 | Naruse et al. |
| 5,375,979 A | 12/1994 | Trah |
| 5,376,252 A | 12/1994 | Ekstrom |
| 5,400,741 A | 3/1995 | DeTitta et al. |
| 5,417,235 A | 5/1995 | Wise et al. |
| 5,423,287 A | 6/1995 | Usami et al. |
| 5,434,049 A | 7/1995 | Okuno et al. |
| 5,445,934 A | 8/1995 | Fodor et al. |
| 5,452,878 A | 9/1995 | Gravesen et al. |
| 5,454,472 A | 10/1995 | Benecke et al. |
| 5,486,335 A | 1/1996 | Wilding et al. |
| 5,487,003 A | 1/1996 | Iwasawa et al. |
| 5,496,009 A | 3/1996 | Farrell et al. |
| 5,498,392 A | 3/1996 | Wilding et al. |
| 5,500,071 A | 3/1996 | Kaltenbach et al. |
| 5,512,131 A | 4/1996 | Kumar et al. |
| 5,525,464 A | 6/1996 | Drmanac et al. |
| 5,529,465 A | 6/1996 | Zengerle et al. |
| 5,558,998 A | 9/1996 | Hammond et al. |
| 5,571,410 A | 11/1996 | Swedberg et al. |
| 5,574,893 A | 11/1996 | Southgate et al. |
| 5,578,528 A | 11/1996 | Wuu et al. |
| 5,580,523 A | 12/1996 | Bard |
| 5,589,136 A | 12/1996 | Northrup et al. |
| 5,593,130 A | 1/1997 | Hansson et al. |
| 5,595,650 A | 1/1997 | Manz |
| 5,604,098 A | 2/1997 | Mead et al. |
| 5,608,519 A | 3/1997 | Gourley |
| 5,632,876 A | 5/1997 | Zanzucchi et al. |
| 5,637,469 A | 6/1997 | Wilding et al. |
| 5,639,423 A | 6/1997 | Northrup et al. |
| 5,641,400 A | 6/1997 | Kaltenbach et al. |
| 5,642,015 A | 6/1997 | Whitehead et al. |
| 5,646,039 A | 7/1997 | Northrup et al. |
| 5,656,155 A | 8/1997 | Norcross et al. |
| 5,659,171 A | 8/1997 | Young et al. |
| 5,660,370 A | 8/1997 | Webster |
| 5,661,222 A | 8/1997 | Hare |
| 5,665,070 A | 9/1997 | McPhee |
| 5,674,742 A | 10/1997 | Northrup et al. |
| 5,681,024 A | 10/1997 | Lisec et al. |
| 5,681,484 A | 10/1997 | Zanzucchi et al. |
| 5,702,618 A | 12/1997 | Saaski et al. |
| 5,705,018 A | 1/1998 | Hartley |
| 5,716,852 A | 2/1998 | Yager et al. |
| 5,726,404 A | 3/1998 | Brody |
| 5,726,751 A | 3/1998 | Altendorf et al. |
| 5,750,015 A | 5/1998 | Soane et al. |
| 5,757,482 A | 5/1998 | Fuchs et al. |
| 5,759,014 A | 6/1998 | Van Lintel |
| 5,775,371 A | 7/1998 | Pan et al. |
| 5,779,868 A | 7/1998 | Parce et al. |
| 5,788,468 A | 8/1998 | Dewa et al. |
| 5,800,690 A | 9/1998 | Chow et al. |
| 5,802,856 A | 9/1998 | Schaper et al. |
| 5,807,522 A | 9/1998 | Brown et al. |
| 5,812,394 A | 9/1998 | Lewis et al. |
| 5,815,306 A | 9/1998 | Sheridon et al. |
| 5,832,165 A | 11/1998 | Reichert et al. |
| 5,833,926 A | 11/1998 | Wurzel et al. |
| 5,836,750 A | 11/1998 | Cabuz |
| 5,837,200 A | 11/1998 | Diessel et al. |
| 5,837,832 A | 11/1998 | Chee et al. |
| 5,839,722 A | 11/1998 | Berlin et al. |
| 5,842,787 A | 12/1998 | Kopf-Sill et al. |
| 5,846,396 A | 12/1998 | Zanzucchi et al. |
| 5,846,708 A | 12/1998 | Hollis et al. |
| 5,852,495 A | 12/1998 | Parce |
| 5,854,684 A | 12/1998 | Stabile et al. |
| 5,856,174 A | 1/1999 | Lipshutz et al. |
| 5,858,187 A | 1/1999 | Ramsey et al. |
| 5,858,195 A | 1/1999 | Ramsey |
| 5,858,649 A | 1/1999 | Asgari et al. |
| 5,863,502 A | 1/1999 | Southgate et al. |
| 5,863,722 A | 1/1999 | Brenner |
| 5,863,801 A | 1/1999 | Southgate et al. |
| 5,866,345 A | 2/1999 | Wilding et al. |
| 5,867,399 A | 2/1999 | Rostoker et al. |
| 5,869,004 A | 2/1999 | Parce et al. |
| 5,871,697 A | 2/1999 | Rothberg et al. |
| 5,872,010 A | 2/1999 | Karger et al. |
| 5,875,817 A | 3/1999 | Carter |
| 5,876,187 A | 3/1999 | Afromowitz |
| 5,876,675 A | 3/1999 | Kennedy |
| 5,876,946 A | 3/1999 | Burbaum et al. |
| 5,880,071 A | 3/1999 | Parce et al. |
| 5,885,470 A | 3/1999 | Parce et al. |
| 5,888,778 A | 3/1999 | Shuber |
| 5,904,824 A | 5/1999 | Oh |
| 5,922,591 A | 7/1999 | Anderson et al. |
| 5,922,604 A | 7/1999 | Stapelton et al. |
| 5,928,880 A | 7/1999 | Wilding et al. |
| 5,932,100 A | 8/1999 | Yager et al. |
| 5,932,799 A | 8/1999 | Moles |
| 5,939,709 A | 8/1999 | Ghislain et al. |
| 5,942,443 A | 8/1999 | Parce et al. |
| 5,948,227 A | 9/1999 | Dubrow |
| 5,958,344 A | 9/1999 | Levine et al. |
| RE36,350 E | 10/1999 | Swedberg et al. |
| 5,965,001 A | 10/1999 | Chow et al. |
| 5,971,355 A | 10/1999 | Biegelsen et al. |
| 5,972,639 A | 10/1999 | Parandoosh |
| 5,976,822 A | 11/1999 | Landrum et al. |
| 5,994,696 A | 11/1999 | Tai et al. |
| 5,997,961 A | 12/1999 | Feng et al. |
| 6,004,442 A | 12/1999 | Choulga et al. |
| 6,004,515 A | 12/1999 | Parce et al. |
| 6,007,309 A | 12/1999 | Hartley |
| 6,007,690 A | 12/1999 | Nelson et al. |
| 6,015,531 A | 1/2000 | Colin et al. |
| 6,018,616 A | 1/2000 | Schaper |
| 6,040,166 A | 3/2000 | Erlich et al. |
| 6,042,709 A | 3/2000 | Parce et al. |
| 6,043,080 A | 3/2000 | Lipshutz et al. |
| 6,045,994 A | 4/2000 | Zabeau et al. |
| 6,046,056 A | 4/2000 | Parce et al. |
| 6,048,498 A | 4/2000 | Kennedy |
| 6,056,001 A | 5/2000 | Boyles et al. |
| 6,056,428 A | 5/2000 | Devoino et al. |
| 6,062,261 A | 5/2000 | Jacobson et al. |
| 6,074,827 A | 6/2000 | Nelson et al. |
| 6,089,534 A | 7/2000 | Biegelsen et al. |
| 6,094,274 A | 7/2000 | Yokoi |
| 6,102,068 A | 8/2000 | Higdon et al. |
| 6,103,199 A | 8/2000 | Bjornson et al. |
| 6,103,537 A | 8/2000 | Ullman et al. |
| 6,107,044 A | 8/2000 | Nikiforov |
| 6,117,634 A | 9/2000 | Langmore et al. |

(56) References Cited

U.S. PATENT DOCUMENTS

| | | |
|---|---|---|
| 6,123,769 A | 9/2000 | Sanjoh |
| 6,132,580 A | 10/2000 | Mathies et al. |
| 6,132,685 A | 10/2000 | Kercso et al. |
| 6,136,212 A | 10/2000 | Mastrangelo et al. |
| 6,140,045 A | 10/2000 | Wohlstadter et al. |
| 6,143,496 A | 11/2000 | Brown et al. |
| 6,146,842 A | 11/2000 | Josiah et al. |
| 6,149,787 A | 11/2000 | Chow et al. |
| 6,149,870 A | 11/2000 | Parce et al. |
| 6,150,119 A | 11/2000 | Kopf-Sill et al. |
| 6,150,180 A | 11/2000 | Parce et al. |
| 6,155,282 A | 12/2000 | Zachary et al. |
| 6,165,694 A | 12/2000 | Liu |
| 6,167,910 B1 | 1/2001 | Chow |
| 6,171,850 B1 | 1/2001 | Nagle et al. |
| 6,174,365 B1 | 1/2001 | Sanjoh |
| 6,174,675 B1 | 1/2001 | Chow et al. |
| 6,182,020 B1 | 1/2001 | Fairbanks |
| 6,197,595 B1 | 3/2001 | Anderson et al. |
| 6,202,687 B1 | 3/2001 | Park |
| 6,214,246 B1 | 4/2001 | Craighead |
| 6,221,654 B1 | 4/2001 | Quake et al. |
| 6,225,109 B1 | 5/2001 | Juncosa et al. |
| 6,227,809 B1 | 5/2001 | Forster et al. |
| 6,235,175 B1 | 5/2001 | Dubrow et al. |
| 6,235,471 B1 | 5/2001 | Knapp et al. |
| 6,246,330 B1 | 6/2001 | Nielsen |
| 6,274,337 B1 | 8/2001 | Parce et al. |
| 6,296,673 B1 | 10/2001 | Santarsiero et al. |
| 6,306,659 B1 | 10/2001 | Parce et al. |
| 6,321,791 B1 | 11/2001 | Chow |
| 6,329,209 B1 | 12/2001 | Wagner et al. |
| 6,344,325 B1 | 2/2002 | Quake et al. |
| 6,345,502 B1 | 2/2002 | Tai et al. |
| 6,352,838 B1 | 3/2002 | Krulevitch et al. |
| 6,355,420 B1 | 3/2002 | Chan |
| 6,358,387 B1 | 3/2002 | Kopf-Sill et al. |
| 6,361,671 B1 | 3/2002 | Mathies et al. |
| 6,375,871 B1 | 4/2002 | Bentsen et al. |
| 6,376,971 B1 | 4/2002 | Pelrine et al. |
| 6,382,254 B1 | 5/2002 | Yang et al. |
| 6,406,605 B1 | 6/2002 | Moles |
| 6,408,878 B2 | 6/2002 | Unger et al. |
| 6,409,832 B2 | 6/2002 | Weigl et al. |
| 6,431,212 B1 | 8/2002 | Hayenga et al. |
| 6,444,426 B1 | 9/2002 | Short et al. |
| 6,488,832 B2 | 12/2002 | Heller |
| 6,488,872 B1 | 12/2002 | Beebe et al. |
| 6,500,323 B1 | 12/2002 | Chow et al. |
| 6,505,125 B1 | 1/2003 | Ho |
| 6,508,988 B1 | 1/2003 | Van Dam et al. |
| 6,520,936 B1 | 2/2003 | Mann |
| 6,528,249 B1 | 3/2003 | Short |
| 6,533,914 B1 | 3/2003 | Liu |
| 6,537,799 B2 | 3/2003 | Chow et al. |
| 6,540,895 B1 | 4/2003 | Spence et al. |
| 6,541,071 B1 | 4/2003 | Bookbinder et al. |
| 6,555,315 B1 | 4/2003 | Short |
| 6,561,208 B1 | 5/2003 | O'Connor et al. |
| 6,563,111 B1 | 5/2003 | Moon et al. |
| 6,569,382 B1 | 5/2003 | Edman et al. |
| 6,581,441 B1 | 6/2003 | Paul |
| 6,596,545 B1 | 7/2003 | Wagner et al. |
| 6,605,472 B1 | 8/2003 | Skinner et al. |
| 6,619,311 B2 | 9/2003 | O'Connor et al. |
| 6,627,076 B2 | 9/2003 | Griffiths |
| 6,637,463 B1 | 10/2003 | Lei et al. |
| 6,645,432 B1 | 11/2003 | Anderson et al. |
| 6,662,818 B2 | 12/2003 | Paul et al. |
| 6,664,104 B2 | 12/2003 | Pourahmadi et al. |
| 6,667,124 B2 | 12/2003 | Suenaga et al. |
| 6,677,131 B2 | 1/2004 | Yuen |
| 6,689,473 B2 | 2/2004 | Guire et al. |
| 6,713,327 B2 | 3/2004 | Leedy |
| 6,716,378 B2 | 4/2004 | Yang et al. |
| 6,736,978 B1 | 5/2004 | Porter et al. |
| 6,749,814 B1 | 6/2004 | Bergh et al. |
| 6,752,922 B2 | 6/2004 | Huang et al. |
| 6,765,279 B2 | 7/2004 | Leedy |
| 6,767,706 B2 | 7/2004 | Quake et al. |
| 6,829,753 B2 | 12/2004 | Lee et al. |
| 6,833,242 B2 | 12/2004 | Quake et al. |
| 6,847,153 B1 | 1/2005 | Balizer |
| 6,866,785 B2 | 3/2005 | Zare et al. |
| 6,884,346 B2 | 4/2005 | Zare et al. |
| 6,885,982 B2 | 4/2005 | Harris et al. |
| 6,911,345 B2 | 6/2005 | Quake et al. |
| 6,929,030 B2 | 8/2005 | Unger et al. |
| 6,939,452 B2 | 9/2005 | Foret et al. |
| 6,951,632 B2 | 10/2005 | Unger et al. |
| 6,960,437 B2 | 11/2005 | Enzelberger et al. |
| 6,977,145 B2 | 12/2005 | Fouillet et al. |
| 7,042,649 B2 | 5/2006 | Quake et al. |
| 7,059,348 B2 | 6/2006 | Nat |
| 7,062,418 B2 | 6/2006 | Lee et al. |
| 7,097,809 B2 | 8/2006 | Dam et al. |
| 7,118,910 B2 | 10/2006 | Unger et al. |
| 7,143,785 B2 | 12/2006 | Maerkl et al. |
| 7,161,736 B2 | 1/2007 | Legrand et al. |
| 7,192,629 B2 | 3/2007 | Lammertink et al. |
| 7,214,298 B2 | 5/2007 | Spence et al. |
| 7,217,367 B2 | 5/2007 | Huang et al. |
| 7,232,109 B2 | 6/2007 | Driggs et al. |
| 7,248,413 B2 | 7/2007 | Quake et al. |
| 7,258,774 B2 | 8/2007 | Chou et al. |
| 7,262,923 B2 | 8/2007 | Quake et al. |
| 7,279,146 B2 | 10/2007 | Nassef |
| 7,291,512 B2 | 11/2007 | Unger |
| 7,294,503 B2 | 11/2007 | Quake et al. |
| 7,368,163 B2 | 5/2008 | Huang et al. |
| 7,378,280 B2 | 5/2008 | Quake et al. |
| 7,413,712 B2 | 8/2008 | Liu et al. |
| 7,442,556 B2 | 10/2008 | Manger et al. |
| 7,452,726 B2 | 11/2008 | Chou et al. |
| 7,476,363 B2 | 1/2009 | Unger et al. |
| 7,526,741 B2 | 4/2009 | Lee et al. |
| 7,604,965 B2 | 10/2009 | McBride et al. |
| 7,622,081 B2 | 11/2009 | Quake et al. |
| 7,666,361 B2 | 2/2010 | McBride et al. |
| 7,670,471 B2 | 3/2010 | Quake et al. |
| 7,678,547 B2 | 3/2010 | Eyal et al. |
| 7,691,333 B2 | 4/2010 | McBride et al. |
| 7,749,737 B2 | 7/2010 | McBride et al. |
| 7,772,373 B2 | 8/2010 | Hansen et al. |
| 7,792,345 B2 | 9/2010 | Taylor et al. |
| 7,815,868 B1 | 10/2010 | Jones et al. |
| 7,820,427 B2 | 10/2010 | Unger et al. |
| 7,833,708 B2 | 11/2010 | Enzelberger et al. |
| 7,837,946 B2 | 11/2010 | McBride et al. |
| 8,871,446 B2 | 10/2014 | Hong et al. |
| 2001/0027745 A1 | 10/2001 | Weigl et al. |
| 2001/0029983 A1 | 10/2001 | Unger et al. |
| 2001/0041357 A1 | 11/2001 | Fouillet et al. |
| 2002/0005354 A1 | 1/2002 | Spence et al. |
| 2002/0012926 A1 | 1/2002 | Quake et al. |
| 2002/0014673 A1 | 2/2002 | Leedy |
| 2002/0028504 A1 | 3/2002 | MacCaskill et al. |
| 2002/0037499 A1 | 3/2002 | Quake et al. |
| 2002/0045297 A1 | 4/2002 | Leedy |
| 2002/0058332 A1 | 5/2002 | Quake et al. |
| 2002/0064885 A1 | 5/2002 | Bedingham et al. |
| 2002/0108096 A1 | 8/2002 | Lee et al. |
| 2002/0108097 A1 | 8/2002 | Harris et al. |
| 2002/0109114 A1 | 8/2002 | Driggs et al. |
| 2002/0121487 A1 | 9/2002 | Robotti et al. |
| 2002/0124896 A1 | 9/2002 | O'Connor et al. |
| 2002/0127736 A1 | 9/2002 | Fu et al. |
| 2002/0141903 A1 | 10/2002 | Parunak et al. |
| 2002/0145231 A1 | 10/2002 | Hansen et al. |
| 2002/0158022 A1 | 10/2002 | Huang et al. |
| 2002/0164816 A1 | 11/2002 | Quake |
| 2002/0166585 A1 | 11/2002 | O'Connor et al. |
| 2002/0187560 A1 | 12/2002 | Pezzuto et al. |
| 2002/0197603 A1 | 12/2002 | Chow et al. |

(56) References Cited

U.S. PATENT DOCUMENTS

| | | |
|---|---|---|
| 2003/0008308 A1 | 1/2003 | Enzelberger et al. |
| 2003/0019833 A1 | 1/2003 | Unger et al. |
| 2003/0064507 A1 | 4/2003 | Gallagher et al. |
| 2003/0080442 A1 | 5/2003 | Unger |
| 2003/0099928 A1 | 5/2003 | Burlage |
| 2003/0119177 A1 | 6/2003 | Gruber et al. |
| 2003/0134129 A1 | 7/2003 | Lammertink et al. |
| 2003/0138829 A1 | 7/2003 | Unger et al. |
| 2003/0143120 A1 | 7/2003 | Ruediger et al. |
| 2003/0175947 A1 | 9/2003 | Liu et al. |
| 2003/0190608 A1 | 10/2003 | Blackburn |
| 2003/0196695 A1 | 10/2003 | O'Connor et al. |
| 2004/0072278 A1 | 4/2004 | Chou et al. |
| 2004/0096960 A1 | 5/2004 | Burd Mehta et al. |
| 2004/0112442 A1 | 6/2004 | Maerkl et al. |
| 2004/0115838 A1 | 6/2004 | Quake et al. |
| 2004/0141887 A1 | 7/2004 | Mainquist et al. |
| 2004/0180377 A1 | 9/2004 | Manger et al. |
| 2004/0248167 A1 | 12/2004 | Quake et al. |
| 2005/0037471 A1 | 2/2005 | Liu et al. |
| 2005/0065735 A1 | 3/2005 | Lee et al. |
| 2005/0084421 A1 | 4/2005 | Unger et al. |
| 2005/0123947 A1 | 6/2005 | Quake et al. |
| 2005/0164376 A1 | 7/2005 | Balagadde et al. |
| 2005/0180891 A1 | 8/2005 | Webster |
| 2005/0196785 A1 | 9/2005 | Quake et al. |
| 2005/0197652 A1 | 9/2005 | Nat |
| 2005/0221373 A1 | 10/2005 | Enzelberger et al. |
| 2005/0252773 A1 | 11/2005 | McBride et al. |
| 2006/0086309 A1 | 4/2006 | Manger et al. |
| 2006/0172408 A1 | 8/2006 | Quake et al. |
| 2006/0228749 A1 | 10/2006 | Wang |
| 2006/0281183 A1 | 12/2006 | Sun et al. |
| 2007/0004033 A1 | 1/2007 | Unger et al. |
| 2007/0134807 A1 | 6/2007 | Bao et al. |
| 2007/0140926 A1 | 6/2007 | Heimberg et al. |
| 2007/0224617 A1 | 9/2007 | Quake et al. |
| 2007/0248971 A1 | 10/2007 | Maerkl et al. |
| 2008/0029169 A1 | 2/2008 | Maerkl et al. |
| 2008/0050283 A1 | 2/2008 | Chou et al. |
| 2008/0075380 A1 | 3/2008 | Dube et al. |
| 2008/0108063 A1 | 5/2008 | Lucero et al. |
| 2008/0129736 A1 | 6/2008 | Sun et al. |
| 2008/0176211 A1 | 7/2008 | Spence et al. |
| 2008/0210320 A1 | 9/2008 | Quake et al. |
| 2008/0223721 A1 | 9/2008 | Cohen et al. |
| 2008/0230387 A1 | 9/2008 | McBride et al. |
| 2008/0264863 A1 | 10/2008 | Quake et al. |
| 2008/0274493 A1 | 11/2008 | Quake et al. |
| 2008/0281090 A1 | 11/2008 | Lee et al. |
| 2008/0289710 A1 | 11/2008 | Unger et al. |
| 2008/0292504 A1 | 11/2008 | Goodsaid et al. |
| 2009/0018195 A1 | 1/2009 | Balagadde |
| 2009/0035838 A1 | 2/2009 | Quake et al. |
| 2009/0069194 A1 | 3/2009 | Ramakrishnan |
| 2009/0142236 A1 | 6/2009 | Unger et al. |
| 2009/0147918 A1 | 6/2009 | Fowler et al. |
| 2009/0239308 A1 | 9/2009 | Dube et al. |
| 2009/0291435 A1 | 11/2009 | Unger et al. |
| 2010/0104477 A1 | 4/2010 | Liu et al. |
| 2010/0120018 A1 | 5/2010 | Quake et al. |
| 2010/0120077 A1 | 5/2010 | Daridon |
| 2010/0154890 A1 | 6/2010 | Maerkl et al. |
| 2010/0166608 A1 | 7/2010 | Quan et al. |
| 2010/0171954 A1 | 7/2010 | Quake et al. |
| 2010/0183481 A1 | 7/2010 | Facer et al. |
| 2010/0184202 A1 | 7/2010 | McBride et al. |
| 2010/0187105 A1 | 7/2010 | Unger et al. |
| 2010/0196892 A1 | 8/2010 | Quake et al. |
| 2010/0197522 A1 | 8/2010 | Liu et al. |
| 2010/0200782 A1 | 8/2010 | Unger et al. |
| 2010/0230613 A1 | 9/2010 | Pieprzyk et al. |
| 2010/0263732 A1 | 10/2010 | Hansen et al. |
| 2010/0263757 A1 | 10/2010 | Fernandes et al. |
| 2010/0311060 A1 | 12/2010 | Facer et al. |
| 2010/0320364 A1 | 12/2010 | Unger et al. |
| 2015/0238960 A1 | 8/2015 | Hong et al. |

FOREIGN PATENT DOCUMENTS

| | | |
|---|---|---|
| EP | 0 703 364 A1 | 3/1996 |
| EP | 0 706 004 A2 | 4/1996 |
| EP | 0 745 682 B1 | 12/1996 |
| EP | 0 778 351 B1 | 6/1997 |
| EP | 0 779 436 A2 | 6/1997 |
| EP | 0 829 360 A2 | 3/1998 |
| EP | 0 845 603 A1 | 6/1998 |
| EP | 0 846 776 A2 | 6/1998 |
| EP | 0 999 055 A2 | 5/2000 |
| EP | 1 065 378 A2 | 1/2001 |
| GB | 2 097 692 A | 11/1982 |
| GB | 2 155 152 A | 9/1985 |
| GB | 2 264 296 A | 8/1993 |
| GB | 2 264 496 A | 9/1993 |
| GB | 2 308 460 A | 6/1997 |
| JP | H09-43251 A | 2/1997 |
| WO | 90/04652 A1 | 5/1990 |
| WO | 90/15070 A1 | 12/1990 |
| WO | 91/13338 A2 | 9/1991 |
| WO | 91/15750 A1 | 10/1991 |
| WO | 92/16657 A1 | 10/1992 |
| WO | 94/05414 A1 | 3/1994 |
| WO | 95/33846 A1 | 12/1995 |
| WO | 95/33853 A1 | 12/1995 |
| WO | 96/04547 A1 | 2/1996 |
| WO | 96/27025 A1 | 9/1996 |
| WO | 97/02357 A1 | 1/1997 |
| WO | 97/27324 A1 | 7/1997 |
| WO | 97/38300 A1 | 10/1997 |
| WO | 97/45644 A1 | 12/1997 |
| WO | 98/00231 A1 | 1/1998 |
| WO | 98/04742 A1 | 2/1998 |
| WO | 98/07069 A1 | 2/1998 |
| WO | 98/08931 A1 | 3/1998 |
| WO | 98/10267 A1 | 3/1998 |
| WO | 98/45481 A1 | 10/1998 |
| WO | 98/52691 A1 | 11/1998 |
| WO | 99/00655 A2 | 1/1999 |
| WO | 99/04361 A1 | 1/1999 |
| WO | 99/14311 A1 | 3/1999 |
| WO | 99/17093 A1 | 4/1999 |
| WO | 99/36760 A1 | 7/1999 |
| WO | 99/52633 A1 | 10/1999 |
| WO | 99/61888 A2 | 12/1999 |
| WO | 00/00678 A1 | 1/2000 |
| WO | 00/43748 A1 | 7/2000 |
| WO | 00/53801 A1 | 9/2000 |
| WO | 00/60345 A1 | 10/2000 |
| WO | 00/68414 A2 | 11/2000 |
| WO | 00/70082 A1 | 11/2000 |
| WO | 00/01025 A2 | 1/2001 |
| WO | 01/06529 A1 | 1/2001 |
| WO | 01/06575 A1 | 1/2001 |
| WO | 01/07061 A1 | 2/2001 |
| WO | 01/09595 A2 | 2/2001 |
| WO | 01/09595 A3 | 2/2001 |
| WO | 01/24937 A2 | 4/2001 |
| WO | 01/32930 A1 | 5/2001 |
| WO | 01/34302 A2 | 5/2001 |
| WO | 01/45843 A2 | 6/2001 |
| WO | 01/53794 A1 | 7/2001 |
| WO | 01/067369 A2 | 9/2001 |
| WO | 01/89695 A2 | 11/2001 |
| WO | 01/96025 A2 | 12/2001 |
| WO | 02/00343 A2 | 1/2002 |
| WO | 02/29106 A2 | 4/2002 |
| WO | 02/30486 A2 | 4/2002 |
| WO | 02/40874 A1 | 5/2002 |
| WO | 02/43615 A2 | 6/2002 |
| WO | 02/60582 A2 | 8/2002 |
| WO | 02/65005 A1 | 8/2002 |
| WO | 02/72892 A1 | 9/2002 |
| WO | 02/81729 A2 | 10/2002 |

(56) References Cited

FOREIGN PATENT DOCUMENTS

| WO | 02/81935 A2 | 10/2002 |
|---|---|---|
| WO | 02/82047 A2 | 10/2002 |
| WO | 03/037781 A1 | 5/2003 |
| WO | 03/044221 A1 | 5/2003 |
| WO | 03/48295 A1 | 6/2003 |
| WO | 2004/028955 A2 | 4/2004 |
| WO | 2007/033385 A2 | 3/2007 |
| WO | 2007/044091 A2 | 4/2007 |
| WO | 2008/043046 A2 | 4/2008 |
| WO | 2009/100449 A1 | 8/2009 |
| WO | 2010/011852 A1 | 1/2010 |
| WO | 2010/017210 A1 | 2/2010 |
| WO | 2010/077618 A1 | 7/2010 |

OTHER PUBLICATIONS

"Biochips," Nature Biotechnology, vol. 18, Supplement 2000, pp. IT43-IT44, 2000.

"Chapter 9: Microfluidic Devices," Micromachined Transducers Sourcebook, pp. 779-882, 1998.

Affholter, Joseph et al., "Engineering A Revolution," Chemistry in Britain, pp. 48-51, Apr. 1999.

Ahn, Chong H. et al., "Fluid Micropumps Based on Rotary Magnetic Actuators," Proceedings of 1995 IEEE Micro Electro Mechanical Systems Workshop (MEMS '95), Amsterdam, Netherlands, pp. 408-412, Jan. 29-Feb. 2, 1995.

Anderson, Janelle R. et al., "Fabrication of Topologically Complex Three-Dimensional Microfluidic Systems in PDMS by Rapid Prototyping," Analytical Chemistry, vol. 72, No. 14, pp. 3158-3164, Jul. 15, 2000.

Anderson, Rolfe C. et al., "Microfluidic Biochemical Analysis System," Transducers '97, 1997 International Conference on Solid-State Sensors and Actuators, Chicago, Illinois, pp. 477-480, Jun. 16-19, 1997.

Andersson et al., "Consecutive Microcontact Printing—Ligands for Asymmetric Catalysis in Silicon Channel," Sensors & Actuators B, vol. 3997, pp. 1-7, 2001.

Angell, James B. et al., "Silicon Micromechanical Devices," Scientific American, pp. cover, 44-55, Apr. 1983.

Applied Biosystems, "TaqMan® PCR Reagent Kit With AmpliTaq Gold® DNA Polymerase Protocol," Jan. 2003.

Armani, Deniz et al., "Re-Configurable Fluid Circuits by PDMS Elastomer Micromachining," IEEE Int. Conf. Micro Electro Mech. Syst. Tech. Digest, vol. 12, pp. 222-227, 1999.

Arnold, Frances H., "Design by Directed Evolution," Accounts of Chemical Research, vol. 31, No. 3, pp. 125-131, 1998.

Ashkin, A. et al., "Optical Trapping and Manipulation of Single Cells Using Infrared Laser Beams," Nature, vol. 330, No. 24, pp. 769-771, Dec. 31, 1987.

Ashkin, A. et al., "Optical Trapping and Manipulation of Viruses and Bacteria," Science, vol. 235, pp. 1517-1520, Mar. 20, 1987.

Axelrod, Daniel, "Cell-Substrate Contacts Illuminated by Total Internal Reflection Fluorescence," Journal of Cell Biology, vol. 89, pp. 141-145, Apr. 1981.

Bader, Joel S. et al., "DNA Transport by a Micromachined Brownian Ratchet Device," PNAS, vol. 96, No. 23, pp. 13165-13169, Nov. 9, 1999.

Ballantyne, J. P. et al., "Selective Area Metallization by Electron-Beam Controlled Direct Metallic Deposition," J. Vac. Sci. Technol., vol. 10, No. 6, pp. 1094-1097, Nov. 1973.

Barron, Annelise E. et al., "Capillary Electrophoresis of DNA in Uncross-Linked Polymer Solutions," Journal of Chromatography A, vol. 652, pp. 3-16, 1993.

Barron, Annelise E. et al., "DNA Separations by Slab Gel and Capillary Electrophoresis—Theory and Practice," Separation and Purification Methods, vol. 24, No. 1, pp. 1-118, 1995.

Barron, Annelise E. et al., "The Use of Coated and Uncoated Capillaries for the Electrophoretic Separation of DNA in Dilute Polymer-Solutions," Electrophoresis, vol. 16, pp. 64-74, 1995.

Bein, Thomas, "Efficient Assays for Combinatorial Methods for the Discovery of Catalysts," Angew. Chem. Int. Ed., vol. 38, No. 3, pp. 323-326, 1999.

Belgrader et al., "A Battery-Powered Notebook Thermal Cycler for Rapid Multiplex Real-Time PCR Analysis," Anal. Chem., vol. 73, pp. 286-289, 2001.

Belgrader et al., "PCR Detection of Bacteria in Seven Minutes," Science, 284(5413), pp. 449-450, 1999.

Belgrader, Phillip et al., "Rapid Pathogen Detection Using a Microchip PCR Array Instrument," Clinical Chemistry, vol. 44, No. 10, pp. 2191-2194, 1998.

Benard, W. L. et al., "A Titanium-Nickel Shape-Memory Alloy Actuated Micropump," Transducers '97, 1997 International Conference on Solid-State Sensors and Actuators, Chicago, Illinois, pp. 361-364, Jun. 16-19, 1997.

Black, Harvey, "Tiny Technology Promises Tremendous Profits," The Scientist, vol. 15, No. 21, 4 pages, Oct. 29, 2001.

Blanch, Harvey W. et al., Biochemical Engineering, pp. 2 cover pages and 305, 1996.

Blankenstein, Gert et al., "Modular Concept of a Laboratory on a Chip for Chemical and Biochemical Analysis," Biosensors & Bioelectronics, vol. 13, Nos. 3-4, pp. 427-438, 1998.

Bloomstein, T. M. et al., "Laser-Chemical Three-Dimensional Writing for Microelectromechanics and Application to Standard-Cell Microfluidics," J. Vac. Sci. Technol. B, vol. 10, No. 6, pp. 2671-2674, Nov. 1992.

Bousse, Luc et al., "Electrokinetically Controlled Microfluidic Analysis Systems," Annu. Rev. Biophys. Biomol. Struct., vol. 29, pp. 155-181, 2000.

Braslavsky et al.; "Single Molecule Measurements of DNA Polymerase Activity: A Step Towards Single Molecule Sequencing", Biophysics Journal Abstracts Issue, 2002, p. 507A, vol. 82, No. 1.

Brechtel, R. et al., "Control of the Electroosmotic Flow by Metal-Salt-Containing Buffers," Journal of Chromatography A, vol. 716, pp. 97-105, 1995.

Breslauer, Kenneth J. et al., "Predicting DNA Duplex Stability From the Base Sequence," Proc. Natl. Acad. Sci. USA, vol. 83, pp. 3746-3750, Jun. 1986.

Brody, J. P. et al., "Low Reynolds Number Micro-Fluidic Devices," In Proc. of Solid-State Sensor and Actuator Workshop, pp. 105-108, Jun. 1996.

Brody, James P. et al., "Significance and Statistical Errors in the Analysis of DNA Microarray Data," PNAS, vol. 99, No. 20, pp. 12975-12978, Oct. 1, 2002.

Brush, Michael, "Automated Laboratories," The Scientist, vol. 13, No. 4, 10 pages, Feb. 15, 1999.

Bryzek, Janusz et al., "Micromachines on the March", IEEE Spectrum, vol. 31, No. 5, pp. 20-31, May 1994.

Buchaillot, Lionel et al., "Silicon Nitride Thin Films Young's Modulus Determination by an Optical Non Destructive Method," Jpn. J. Appl. Phys., vol. 36, Part 2, No. 6B, pp. L794-L797, Jun. 15, 1997.

Budowle, Bruce et al., "Analysis of the VNTR Locus DIS80 by the PCR Followed by High-Resolution PAGE," Am. J. Hum. Genet., vol. 48, pp. 137-144, 1991.

Buican, Tudor N. et al., "Automated Single-Cell Manipulation and Sorting by Light Trapping," Applied Optics, vol. 26, No. 24, pp. 5311-5316, Dec. 15, 1987.

Bulyk, Martha L. et al., "Quantifying DNA-Protein Interactions by Double-Stranded DNA Arrays," Nature Biotechnology, vol. 17, pp. 573-577, Jun. 1999.

Burbaum, Jonathan J. et al., "New Technologies for High-Throughput Screening," Current Opinion in Chemical Biology, vol. 1, pp. 72-78, 1997.

Burns et al., "An Integrated Nanoliter DNA Analysis Device," Science, vol. 282, pp. 484-487, 1998.

Busch, J. et al., Methods for the Differentiation of Microorganisms, Journal of Chromatography B, vol. 722, pp. 263-278, 1999.

Cai, Weiwen, et al., "High-Resolution Restriction Maps of Bacterial Artificial Chromosomes Constructed by Optical Mapping," Proc. Natl. Acad. Sci. USA, vol. 95, pp. 3390-3395, Mar. 1998.

Calkins, Kathryn, "Mycometrix: Rubber Chips," BioCentury, 2 pages, Oct. 16, 2000.

(56) References Cited

OTHER PUBLICATIONS

Castro, Alonso et al., "Fluorescence Detection and Size Measurement of Single DNA Molecules," Analytical Chemistry, vol. 65, No. 7, pp. 849-852, Apr. 1, 1993.

Chan, Jason H. et al., "Microfabricated Polymer Devices for Automated Sample Delivery of Peptides for Analysis by Electrospray Ionization Tandem Mass Spectrometry," Analytical Chemistry, vol. 71, No. 20, pp. 4437-4444, Oct. 15, 1999.

Chang, Jun Keun et al., "Functional Integration of Serial Dilution and Capillary Electrophoresis on a PDMS Microchip," Biotechnology and Bioprocess Engineering, vol. 8, No. 4, pp. 233-239, 2003.

Chaudhari et al., "Transient Liquid Crystal Thermometry of Microfabricated PCR Vessel Arrays," J. Microelectromechanical Systems, 7(4), pp. 345-355, 1998.

Chee, Mark et al., "Accessing Genetic Information With High-Density DNA Arrays," Science, vol. 274, pp. 610-614, Oct. 25, 1996.

Chen, Chihchen et al., "Gray-Scale Photolithography Using Microfluidic Photomasks," PNAS, vol. 100, No. 4, pp. 1499-1504, Feb. 18, 2003.

Chiang, Yuh-Min et al., "Characterizing the Process of Cast Molding Microfluidic Systems," SPIE, vol. 3877, pp. 303-311, Sep. 1999.

Chiem, N. H. et al., "Microchip Systems for Immunoassay: An Integrated Immunoreactor With Electrophoretic Separation for Serum Theophylline Determination," Clinical Chemistry, vol. 44, No. 3, p. 591, 1998.

Chiou et al., "A Closed-Cycle Capillary Polymerase Chain," Anal. Chem., vol. 73, pp. 2018-2021, 2001.

Chiu, Chi-Sung et al., "Single Molecule Measurements Calibrate Green Fluorescent Protein Surface Densities on Transparent Beads for Use With 'Knock-In' Animals and Other Expression Systems," Journal of Neuroscience Methods, vol. 105, pp. 55-63, 2001.

Chiu, Daniel T. et al., "Patterned Deposition of Cells and Proteins Onto Surfaces by Using Three-Dimensional Microfluidic Systems," PNAS, vol. 97, No. 6, pp. 2408-2413, Mar. 14, 2000.

Chou, Hou-Pu et al., "A Microfabricated Device for Sizing and Sorting DNA Molecules," Proc. Natl. Acad. Sci., vol. 96, pp. 11-13, Jan. 1999.

Chou, Hou-Pu et al., "A Microfabricated Rotary Pump," Biomedical Microdevices, vol. 3, No. 4, pp. 323-330, 2001.

Chou, Hou-Pu et al., "Disposable Microdevices for DNA Analysis and Cell Sorting," Proc. Solid-State Sensor and Actuator Workshop, Hilton Head, South Carolina, pp. 11-14, 6/8-11/1998.

Chou, Hou-Pu et al., "Integrated Elastomer Fluidic Lab-On-A-Chip-Surface Patterning and DNA Diagnostics," Proceedings of the Solid State Actuator and Sensor Workshop, Hilton Head, South Carolina, 4 pages, 2000.

Chou, Hou-Pu et al., "Microfabricated Devices for Sizing DNA and Sorting Cells," Micro- and Nanofabricated Structures and Devices for Biomedical Environmental Applications, Proceedings of SPIE, vol. 3258, pp. 181-187, 1998.

Chou, Hou-Pu et al., "Multiple Disease Diagnostics on a Single Chip," Biophysics Lab, Caltech, pp. 1-4, Mar. 1, 2000.

Chou, Hou-Pu, "Microfabricated Devices for Rapid DNA Diagnostics," Doctoral Thesis, California Institute of Technology, pp. i-xii and 1-106, May 30, 2000.

Costerton, J. William et al., "Microbial Biofilms," Annu. Rev. Microbiol., vol. 49, pp. 711-745, 1995.

Cowen, S. et al., "An On-Chip Miniature Liquid Chromatography System: Design, Construction and Characterization," Micro Total Analysis Systems, Proceedings of the pTAS '94 Workshop, University of Twente, The Netherlands, pp. 2 cover pages and 295-298, 1995.

Crosland-Taylor, P. J., "A Device for Counting Small Particles Suspended in a Fluid Through a Tube," Nature, vol. 171, pp. 37-38, Jan. 3, 1953.

Davila, Herman Moreno, "Molecular and Functional Diversity of Voltage-Gated Calcium Channels," Annals of the New York Academy of Sciences, vol. 868, pp. cover, 102-117, 1999.

Delamarche, Emmanuel et al., "Patterned Delivery of Immunoglobulins to Surfaces Using Microfluidic Networks," Science, vol. 276, pp. 779-781, May 2, 1997.

Delisa, Matthew P. et al., "Mapping Stress-Induced Changes in Autoinducer AI-2 Production in Chemostat-Cultivated *Escherichia coli* K-12," Journal of Bacteriology, vol. 183, No. 9, pp. 2918-2928, May 2001.

Dharmatilleke, Saman et al., "Three-Dimensional Silicone Device Fabrication and Interconnection Scheme for Microfluidic Applications Using Sacrificial Wax Layers," Micro-Electro-Mechanical Systems (MEMS), vol. 2, pp. 413-418, 2000.

Documents from File History for U.S. Appl. No. 11/463,241; Office Actions dated Jan. 11, 2008, Sep. 8, 2008 and Apr. 13, 2009; Amendment filed Aug. 8, 2006; Abandonment dated Nov. 12, 2009, 24 pages 020174-009411US.

Drmanac, R. et al., "DNA Sequence Determination by Hybridization: A Strategy for Efficient Large-Scale Sequencing," Science, vol. 260, pp. 1649-1652, Jun. 11, 1993.

Drmanac, Snezana et al., "Accurate Sequencing by Hybridization for DNA Diagnostics and Individual Genomics," Nature Biotechnology, vol. 16, pp. 54-58, Jan. 1998.

Duffy, David C. et al., "Patterning Electroluminescent Materials With Feature Sizes As Small As 5 µm Using Elastomeric Membranes As Masks for Dry Lift-Off," Advanced Materials, vol. 11, No. 7, pp. 546-552, 1999.

Duffy, David C. et al., "Rapid Prototyping of Microfluidic Switches in Poly(dimethyl siloxane) and Their Actuation by Electro-Osmotic Flow," J. Micromech. Microeng., vol. 9, pp. 211-217, 1999.

Duffy, David C. et al., "Rapid Prototyping of Microfluidic Systems in Poly(dimethylsiloxane)," Analytical Chemistry, vol. 70, No. 23, pp. 4974-4984, Dec. 1, 1998.

Effenhauser, Carlo S. et al., "Integrated Capillary Electrophoresis on Flexible Silicone Microdevices: Analysis of DNA Restriction Fragments and Detection of Single DNA Molecules on Microchips," Analytical Chemistry, vol. 69, No. 17, pp. 3451-3457, Sep. 1, 1997.

Effenhauser, Carlo S. et al., "Integrated Chip-Based Capillary Electrophoresis," Electrophoresis, vol. 18, pp. 2203-2213, 1997.

Effenhauser, Carlo S. et al., "Miniaturizing a Whole Analytical Laboratory Down to Chip Size," American Laboratory, vol. 26, No. 14, pp. cover, 15, 16, 18, 1994.

Effenhauser, Carlo S., "Integrated Chip-Based Microcolumn Separation Systems," Topics in Current Chemistry, vol. 194, pp. cover, 52-82, 1998.

Ericson, Christer et al., "Electroosmosis- and Pressure-Driven Chromatography in Chips Using Continuous Beds," Analytical Chemistry, vol. 72, No. 1, pp. 81-87, Jan. 1, 2000.

Erlich, H.A., PCR Technology, Basic Methodology: Stockton Press, New York, pp. 1-5, 1989.

Eyal, Shulamit et al., "Velocity-Independent Microfluidic Flow Cytometry," Electrophoresis, vol. 23, pp. 2653-2657, 2002.

Fahrenberg, J. et al., "A Microvalve System Fabricated by Thermoplastic Molding," J. Micromech. Microeng., vol. 5, pp. 169-171, 1995.

Felix, Arthur M. et al., "Pegylated Peptides IV—Enhanced Biological Activity of Site-Directed Pegylated GRF Analogs," International Journal of Peptide & Protein Research, vol. 46, pp. 253-264, 1995.

Felix, Arthur M., "Site-Specific Poly(ethylene glycol)ylation of Peptides," Poly(Ethylene Glycol) Chemistry and Biological Applications, ACS Symposium Series 680, pp. 2 cover pages, 218-238, 1997.

Fettinger, J. C. et al., "Stacked Modules for Micro Flow Systems in Chemical Analysis: Concept and Studies Using an Enlarged Model," Sensors and Actuators B, vol. 17, pp. 19-25, 1993.

Fiedler, Stefan et al., "Dielectrophoretic Sorting of Particles and Cells in a Microsystem," Analytical Chemistry, vol. 70, No. 9, pp. 1909-1915, May 1, 1998.

Figeys, Daniel et al., "An Integrated Microfluidics-Tandem Mass Spectrometry System for Automated Protein Analysis," Analytical Chemistry, vol. 70, No. 18, pp. 3728-3734, Sep. 15, 1998.

Figeys, Daniel et al., "Nanoflow Solvent Gradient Delivery From a Microfabricated Device for Protein Identifications by Electrospray Ionization Mass Spectrometry," Analytical Chemistry, vol. 70, No. 18, pp. 3721-3727, Sep. 15, 1998.

(56) References Cited

OTHER PUBLICATIONS

Fitzgerald, Deborah A., "Making Every Nanoliter Count," The Scientist, vol. 15, No. 21, 8 pages, Oct. 29, 2001.
Fodor, Stephen P. A. et al., "Light-Directed, Spatially Addressable Parallel Chemical Synthesis," Science, vol. 251, pp. 767-773, Feb. 15, 1991.
Folch, A. et al., "Molding of Deep Polydimethylsiloxane Microstructures for Microfluidics and Biological Applications," Journal of Biomechanical Engineering, vol. 121, pp. 28-34, Feb. 1999.
Fotin, Alexander V. et al., "Parallel Thermodynamic Analysis of Duplexes on Oilgodeoxyribonucleotide Microchips," Nucleic Acids Research, vol. 26, No. 6, pp. 1515-1521, 1998.
Fu, Anne Y. et al., "A Microfabricated Fluorescence-Activated Cell-Sorter," Nature Biotechnology, vol. 17, pp. 1109-1111, Nov. 1999.
Fu, Anne Y. et al., "An Integrated Microfabricated Cell Sorter," Analytical Chemistry, vol. 74, No. 11, pp. 2451-2457, Jun. 1, 2002.
Fulwyler, M. J., "Electronic Separation of Biological Cells by Volume," Science, pp. 910-911, Nov. 1965.
Galambos, Paul et al., "Electrical and Fluidic Packaging of Surface Micromachined Electro-Microfluidic Devices," 8 pages, no date.
Gao, Jun et al., "Integrated Microfluidic System Enabling Protein Digestion, Peptide Separation, and Protein Identification," Analytical Chemistry, vol. 73, No. 11, pp. 2648-2655, Jun. 1, 2001.
Garno, Jayne C. et al., "Production of Periodic Arrays of Protein Nanostructures Using Particle Lithography," Langmuir, vol. 18, No. 21, pp. 8186-8192, 2002.
Gass, V. et al., "Integrated Flow-Regulated Silicon Micropump," Sensors and Actuators A, vol. 43, pp. 335-338, 1994.
Geng, Xindu et al., "Retention Model for Proteins in Reversed-Phase Liquid Chromatography," Journal of Chromatography, vol. 296, pp. 15-30, 1984.
Gerlach, Torsten, "Pumping Gases by a Silicon Micro Pump With Dynamic Passive Valves," Transducers '97, 1997 International Conference on Solid-State Sensors and Actuators, Chicago, Illinois, pp. 357-360, Jun. 16-19, 1997.
Ginsberg, Michael A., "New Laser System Measure DNA Fragments," Biophotonics International, p. 20, Nov./Dec. 1996.
Giusti, Alan et al., "Application of Deoxyribonucleic Acid (DNA) Polymorphisms to the Analysis of DNA Recovered From Sperm," Journal of Forensic Science, vol. 31, No. 2, pp. 409-417, Apr. 1986.
Goll, C. et al., "Microvalves With Bistable Buckled Polymer Diaphragms," J. Micromech. Microeng., vol. 6, pp. 77-79, 1996.
Gombotz, W. R. et al., "Pegylation: A Tool to Enhance Protein Delivery," Abstracts of Papers, American Chemical Society, vol. 217, Part 2, 2 pages, Mar. 21-25, 1999.
Gonzalez, Jesus E. et al., "Improved Indicators of Cell Membrane Potential That Use Fluorescence Resonance Energy Transfer," Chemistry & Biology, vol. 4, No. 4, pp. 269-277, Apr. 1997.
Goodwin, Peter M. et al., "Rapid Sizing of Individual Fluorescently Stained DNA Fragments by Flow Cytometry," Nucleic Acids Research, vol. 21, No. 4, pp. 803-806, 1993.
Granjeaud, Samuel et al., "Expression Profiling: DNA Arrays in Many Guises," BioEssays, vol. 21, pp. 781-790, 1999.
Gravesen, Peter et al., "Microfluidics—A Review," J. Micromech. Microeng., vol. 3, pp. 168-192, 1993.
Greene, Chana, "Characterizing the Properties of PDMS," pp. 1-11, Summer 2000.
Groisman et al., "Microfluidic Memory and Control Devices" Science 300, 955-958 (2003).
Grover, William H. et al., "Monolithic Membrane Valves and Diaphragm Pumps for Practical Large-Scale Integration Into Glass Microfluidic Devices," Sensors and Actuators B, vol. 89, pp. 315-323, 2003.
Guérin, L. J. et al., "Simple and Low Cost Fabrication of Embedded Micro-Channels by Using a New Thick-Film Photoplastic," Transducers '97, 1997 International Conference on Solid-State Sensors and Actuators, Chicago, Illinois, pp. 1419-1422, Jun. 18-19, 1997.

Guerra, Patricia I. et al., "PEGylation Prevents the N-Terminal Degradation of Megakaryocyte Growth and Development Factor," Pharmaceutical Research, vol. 15, No. 12, pp. 1822-1827, 1998.
Gunderson, K.L. et al. (1998). "Mutation Detection by Ligation to Complete n-mer DNA Arrays," Genome Research 8:1142-1153.
Gunderson, Kevin L. et al., "Mutation Detection by Ligation to Complete n-mer DNA Arrays," Genome Research, vol. 8, pp. 1142-1153, 1998.
Guo, Zhen et al., "Enhanced Discrimination of Single Nucleotide Polymorphisms by Artificial Mismatch Hybridization," Nature Biotechnology, vol. 15, pp. 331-335, Apr. 1997.
Hancock, Robert E. W., "A Brief on Bacterial Biofilms," Nature Genetics, vol. 29, p. 360, Dec. 2001.
Hanes, Jozef, et al., "In Vitro Selection and Evolution of Functional Proteins by Using Ribosome Display," Proc. Natl. Acad. Sci. USA, vol. 94, pp. 4937-4942, May 1997.
Hansen, Carl. L. et al., "A Robust and Scalable Microfluidic Metering Method That Allows Protein Crystal Growth by Free Interface Diffusion," PNAS, vol. 99, No. 26, pp. 16531-16536, Dec. 24, 2002.
Hansen, Carl. L. et al., "Systematic Investigation of Protein-Phase Behavior With a Microfluidic Formulator," PNAS Early Edition, 6 pages, 2004.
Harrison, D. Jed et al., "Integration of Analytical Systems Incorporating Chemical Reactions and Electrophoretic Separation," Micro Total Analysis Systems, Proceedings of the μTAS '94 Workshop, University of Twente, The Netherlands, pp. 2 cover pages and 105-111, 1995.
Harrison, D. Jed et al., "Micromachining a Miniaturized Capillary Electrophoresis-Based Chemical Analysis System on a Chip," Science, vol. 261, pp. 895-897, Aug. 13, 1993.
Henion, Jack et al., "Capillary Electrophoresis/Mass Spectrometry: From One Meter Capillaries to Chip-Based Devices," 2 pages, 1999.
Heo, Jinseok et al., "A Microfluidic Bioreactor Based on Hydrogel-Entrapped E. coli: Cell Viability, Lysis, and Intracellular Enzyme Reactions," Analytical Chemistry, vol. 75, No. 1, pp. 22-26, Jan. 1, 2003.
Herbert, D., "Continuous Culture of Bacteria," The Journal of General Microbiology, vol. 15, pp. 2 cover pages and iv, 1956.
Herbert, D., "Continuous Culture of Bacteria: Principles and Applications," Chemistry and Industry, pp. 381, Mar. 29, 1958.
Hermanson, Greg T. et al., "Chapter 2—Activation Methods," Immobilized Affinity Ligand Techniques, Academic Press, pp. 2 cover pages, 51-136, 1992.
Hicks, Jennifer, "Genetics and Drug Discovery Dominate Microarray Research," R&D Magazine, pp. 28-33, Feb. 1999.
Hoffmuller, Ulrich et al., "In Vitro Evolution and Selection of Proteins: Ribosome Display for Larger Libraries," Angew. Chem. Int. Ed., vol. 37, No. 23, pp. 3241-3243, 1998.
Hofmann, Oliver et al., "Modular Approach to Fabrication of Three-Dimensional Microchannel Systems in PDMS—Application to Sheath Flow Microchips," Lab on a Chip, vol. 1, pp. 108-114, 2001.
Hoheisel, Jorg D., "Sequence-Independent and Linear Variation of Oligonucleotide DNA Binding Stabilities," Nucleic Acids Research, vol. 24, No. 3, pp. 430-432, 1996.
Hong et al., "Integration of Gene Amplification and Capillary Gel Electrophoresis on a Polydimethylsiloxane-Glass Hybrid Microchip," Electrophoresis, vol. 22, pp. 328-333, 2001.
Hong, Jong Wook et al., "A Nanoliter-Scale Nucleic Acid Processor With Parallel Architecture," Nature Biotechnology, vol. 22, No. 4, pp. 1-5, Apr. 2004.
Hopfgartner, Gerard et al., "Exact Mass Measurement of Product Ions for the Structural Elucidation of Drug Metabolites With a Tandem Quadrupole Orthogonal-Acceleration Time-Of-Flight Mass Spectrometer," Journal of the American Society for Mass Spectrometry, vol. 10, pp. cover, 1305-1314, Dec. 1999.
Horn, Howard, "Lab Chips Sector: Microtechnologies Are Changing Healthcare and More," Life Sciences, pp. 19-21, Mar. 20, 2001.

(56) References Cited

OTHER PUBLICATIONS

Hornbeck, Larry J. et al., "Bistable Deformable Mirror Device," Spatial Light Modulators and Applications 1988 Technical Digest Series, vol. 8, Postconference Edition, pp. cover, 107-110, Jun. 15-17, 1988.
Hosokawa, Kazuo et al., "A Microfluidic Device for Mixing of Capillary-Driven Liquids," IEEJ Trans. SM, vol. 123, No. 1, pp. 23-24, 2003.
Hosokawa, Kazuo et al., "Droplet-Based Nano/Picoliter Mixer Using Hydrophobic Microcapillary Vent," 1999 IEEE International Conference on Micro Electro Mechanical Systems, Technical Digest, pp. 388-393, 1999.
Hosokawa, Kazuo et al., "Handling of Picoliter Liquid Samples in a Poly(dimethylsiloxane)-Based Microfluidic Device," Analytical Chemistry, vol. 71, No. 20, pp. 4781-4785, Oct. 15, 1999.
Ibrahim et al., "Real-Time Microchip PCR for Detecting Single-Base Differences in Viral and Human DNA," Anal. Chem., vol. 70, pp. 2013-2017, 1998.
Igloi, Gabor L., "Variability in the Stability of DNA-Peptide Nucleic Acid (PNA) Single-Base Mismatched Duplexes: Real-Time Hybridization During Affinity Electrophoresis in PNA-Containing Gels," Proc. Natl. Acad. Sci. USA, vol. 95, pp. 8562-8567, Jul. 1998.
Ikuta, Koji et al., "Three Dimensional Micro Integrated Fluid Systems (MIFS) Fabricated by Stereo Lithography," IEEE, pp. 1-6, 1994.
Ingraham, John L. et al., Growth of the Bacterial Cell, pp. 3 cover pages and 230, 1983.
Jackman, Rebecca J. et al., "Design and Fabrication of Topologically Complex, Three-Dimensional Microstructures," Science, vol. 280, pp. 2089-2091, Jun. 26, 1998.
Jacobson, Ken et al., "International Workshop on the Application of Fluorescence Photobleaching Techniques to Problems in Cell Biology," Federation Proceedings, vol. 42, No. 1, pp. 72-79, Jan. 1983.
Jacobson, Stephen C. et al., "Open Channel Electrochromatography on a Microchip," Analytical Chemistry, vol. 66, No. 14, pp. 2369-2373, Jul. 15, 1994.
Jacobson, Stephen C. et al., "High-Speed Separations on a Microchip," Analytical Chemistry, vol. 66, No. 7, pp. 1114-1118, Apr. 1, 1994.
Jacobson, Stephen C. et al., "Microfluidic Devices for Electrokinetically Driven Parallel and Serial Mixing," Analytical Chemistry, vol. 71, No. 20, pp. 4455-4459, Oct. 15, 1999.
Jannasch, H. W. et al., "Experimental Bacterial Ecology Studied in Continuous Culture," Advances in Microbial Physiology, vol. 11, pp. cover and 165-212, 1974.
Jeffreys, Alec J. et al., "Hypervariable 'Minisatellite' Regions in Human DNA," Nature, vol. 314, pp. 67-73, Mar. 7, 1985.
Jerman, Hal, "Electrically-Activated, Normally-Closed Diaphragm Valves," Transducers '91, 1991 International Conference on Solid-State Sensors and Actuators, pp. cover, 1045-1048, 1991.
Jermutus, Lutz, et al., "Recent Advances in Producing and Selecting Functional Proteins by Using Cell-Free Translation," Current Opinion in Biotechnology, vol. 9, pp. 534-548, 1998.
Jo, Byung-Ho et al., "Fabrication of Three-Dimensional Microfluidic Systems by Stacking Molded Polydimethylsiloxane (PDMS) Layers" SPIE, vol. 3877, pp. 222-229, Sep. 1999.
Jo, Byung-Ho et al., "Three-Dimensional Micro-Channel Fabrication in Polydimethylsiloxane (PDMS) Elastomer," Journal of Microelectromechanical Systems, vol. 9, No. 1, pp. 76-81, Mar. 2000.
Ju, Li-Ya et al., "Application of Silver Staining to the Rapid Typing of the Polymorphism of HLA-DQ Alleles by Enzymatic Amplification and Allele-Specific Restriction Fragment Length Polymorphism," Electrophoresis, vol. 12, pp. 270-273, 1991.
Juárez-Martínez, G. et al., "High-Throughput Screens for Postgenomics: Studies of Protein Crystallization Using Microsystems Technology," Analytical Chemistry, vol. 74, No. 14, pp. 3505-3510, Jul. 15, 2002.
Jung, D. R. et al., "Chemical and Physical Interactions At Metal/Self-Assembled Organic Monolayer Interfaces," pp. 1-54, 1994.

Kagan, C. R., "Organic-Inorganic Hybrid Materials As Semiconducting Channels in Thin-Film Field-Effect Transistors," Science, vol. 286, pp. 945-947, Oct. 29, 1999.
Kamentsky, Louis A. et al., "Spectrophotometer: New Instrument for Ultrarapid Cell Analysis," Science, vol. 150, pp. 630-631, Oct. 29, 1965.
Kane et al., "Finite element analysis of nonsmooth contact", Computer Methods in Applied Mechanics and Engineering, 180(1-2):1-26 (1999).
Kane, R. S. et al., "Patterning Proteins and Cells Using Soft Lithography," Biomaterials, vol. 20, pp. 2363-2376, 1999.
Kanter, Evan et al., "Analysis of Restriction Fragment Length Polymorphisms in Deoxyribonucleic Acid (DNA) Recovered From Dried Bloodstains," Journal of Forensic Sciences, vol. 31, No. 2, pp. 403-408, Apr. 1986.
Kapur, Ravi et al., "Fabrication and Selective Surface Modification of 3-Dimensionally Textured Biomedical Polymers From Etched Silicon Substrates," Journal of Biomedical Materials Research, vol. 33, pp. 205-216, 1996.
Kawano, Yasushi et al., "Rapid Isolation and Identification of Staphylococcal Exoproteins by Reverse Phase Capillary High Performance Liquid Chromatography-Electrospray Ionization Mass Spectrometry," FEMS Microbiology Letters, vol. 189, pp. 103-108, 2000.
Keller, Richard A. et al., "Single-Molecule Fluorescence Analysis in Solution," Applied Spectroscopy, vol. 50, No. 7, pp. 12A-30A, Jul. 1996.
Kenis, Paul J. A. et al., "Microfabrication Inside Capillaries Using Multiphase Laminar Flow Patterning," Science, vol. 285, pp. 83-85, Jul. 2, 1999.
Khandurina et al., "Bioanalysis in Microfluidic Devices", Journal of Chromatography A, vol. 943, No. 2, Jan. 18, 2002, Elsevier Science B.V., pp. 159-183.
Khandurina et al., "Integrated System for Rapid PCR-Based DNA Analysis in Microfluidic Devices," Anal. Chem., vol. 72, pp. 2995-3000, 2000.
Khoo, Melvin et al., "A Novel Micromachined Magnetic Membrane Microfluid Pump," pp. 1-4, no date.
Kim, Enoch et al., "Micromolding in Capillaries: Applications in Materials Science," J. Am. Chem. Soc., vol. 118, No. 24, pp. 5722-5731, 1996.
Kim, Enoch et al., "Polymer Microstructures Formed by Moulding in Capillaries," Nature, vol. 376, pp. 581-584, Aug. 17, 1995.
Kirk-Othmer, "Concise Encyclopedia of Chemical Technology," John Wiley & Sons, 5 pages, 1985.
Kodera, Yoh et al., "Pegylation of Proteins and Bioactive Substances for Medical and Technical Applications," Prog. Polym. Sci., vol. 23, pp. 1233-1271, 1998.
Kopp, Martin U. et al., "Chemical Amplification: Continuous-Flow PCR on a Chip," Science, vol. 280, pp. 1046-1048, May 15, 1998.
Kuhn, Lawrence et al., "Silicon Charge Electrode Array for Ink Jet Printing," IEEE Transactions on Electron Devices, vol. ED-25, No. 10, pp. 1257-1260, Oct. 1978.
Kumar, Amit et al., "Features of Gold Having Micrometer to Centimeter Dimensions Can Be Formed Through a Combination of Stamping With an Elastomeric Stamp and an Alkanethiol 'Ink' Followed by Chemical Etching," Appl. Phys. Lett., vol. 63, No. 14, pp. 2002-2004, Oct. 4, 1993.
Kumar, Amit et al., "Patterning Self-Assembled Monolayers: Applications in Materials Science," Langmuir, vol. 10, pp. 1498-1511, 1994.
Kutyavin, Igor V. et al., "3'-Minor Groove Binder-DNA Probes Increase Sequence Specificity At PCR Extension Temperatures," Nucleic Acids Research, vol. 28, No. 2, pp. 655-661, 2000.
Lagally, E. T. et al., "Single-Molecule DNA Amplification and Analysis in an Integrated Microfluidic Device," Analytical Chemistry, vol. 73, No. 3, pp. 565-570, Feb. 1, 2001.
Lagally, Eric T. et al., "Fully Integrated PCR-Capillary Electrophoresis Microsystem for DNA Analysis," Lab on a Chip, vol. 1, pp. 102-107, 2001.
Lagally, Eric T. et al., "Monolithic Integrated Microfluidic DNA Amplification and Capillary Electrophoresis Analysis System," Sensors and Actuators B, vol. 63, pp. 138-146, 2000.

(56) References Cited

OTHER PUBLICATIONS

Lammerink, T. S. J. et al., "Modular Concept for Fluid Handling Systems," IEEE, pp. 389-394, 1996.
Lane, P. G., "Analysis of a Continuous-Culture Technique for the Selection of Mutants Tolerant to Extreme Environmental Stress," Biotechnology and Bioengineering, vol. 65, No. 4, pp. 397-406, Nov. 20, 1999.
Last Chance for Micromachines, The Economist Technology Quarterly, located at www.economist.com, 8 pages, Dec. 7, 2000.
Lawrence, J. R. et al., "Optical Sectioning of Microbial Biofilms," Journal of Bacteriology, vol. 173, No. 20, pp. 6558-6567, Oct. 1991.
Lazar, Iulia M. et al., "Novel Microfabricated Device for Electrokinetically Induced Pressure Flow and Electrospray Ionization Mass Spectrometry," Journal of Chromatography A, vol. 892, pp. 195-201, 2000.
Lee, L. Stanford et al., "Prolonged Circulating Lives of Single-Chain Fv Proteins Conjugated With Polyethylene Glycol: A Comparison of Conjugation Chemistries and Compounds," Bioconjugate Chem., vol. 10, pp. 973-981, 1999.
Lessard, Guillaume A. et al., "A Scanning Apertureless Fluorescence Microscope," 8 pages, 1999.
Levine, Leanna M. et al., "Measurement of Specific Protease Activity Utilizing Fluorescence Polarization," Analytical Biochemistry, vol. 247, pp. 83-88, 1997.
Li, Jianjun et al., "Integration of Microfabricated Devices to Capillary Electrophoresis-Electrospray Mass Spectrometry Using a Low Dead Volume Connection: Application to Rapid Analyses of Proteolytic Digests," Analytical Chemistry, vol. 71, No. 15, pp. 3036-3045, Aug. 1, 1999.
Li, Paul C. H. et al., "Transport, Manipulation, and Reaction of Biological Cells On-Chip Using Electrokinetic Effects," Analytical Chemistry, vol. 69, No. 8, pp. 1564-1568, Apr. 15, 1997.
Lichtenberg, Jan et al., "Sample Pretreatment on Microfabricated Devices," Talanta, vol. 56, pp. 233-266, 2002.
Licklider, Larry et al., "A Micromachined Chip-Based Electrospray Source for Mass Spectrometry," Analytical Chemistry, vol. 72, No. 2, pp. 367-375, Jan. 15, 2000.
Lin, L. Y. et al., "Free-Space Micromachined Optical Switches for Optical Networking," IEEE Journal of Selected Topics in Quantum Electronics, vol. 5, No. 1, pp. 4-9, Jan. 1999.
Lin, Yuehe et al., "Laser Micromachined Isoelectric Focusing Device on Polymer Substrate for Electrospray Mass Spectrometry," SPIE, vol. 3877, pp. 28-35, Sep. 1999.
Liu et al., "Solving the "World-to-chip" Interface Problem with a Microfluidic Matrix" Anal. Biochem. (2003) 75:4718-4723.
Liu, Hanghui et al., "Development of Multichannel Devices With an Array of Electrospray Tips for High-Throughput Mass Spectrometry," Analytical Chemistry, vol. 72, No. 14, pp. 3303-3310, Jul. 15, 2000.
Liu, Jian et al., "A Nanoliter Rotary Device for Polymerase Chain Reaction," Electrophoresis, vol. 23, pp. 1531-1536, 2002.
Llopis, Juan et al., "Ligand-Dependent Interactions of Coactivators Steroid Receptor Coactivator-1 and Peroxisome Proliferator-Activated Receptor Binding Protein With Nuclear Hormone Receptors Can Be Imaged in Live Cells and Are Required for Transcription," PNAS, vol. 97, No. 8, pp. 4363-4368, Apr. 2000.
Lorenz et al., "Screening for Novel Enzymes for Biocatalytic Processes: Accessing the Metagenome as a Resource of Novel Functional Sequence Space," *Current Opinion in Biotechnology*, (2002) 13:572-577.
Lötters, J C et al., "The Mechanical Properties of the Rubber Elastic Polymer Polydimethylsiloxane for Sensor Applications," J. Micromech. Microeng., vol. 7, pp. 145-147, 1997.
Lucy, Charles A. et al., "Characterization of the Cationic Surfactant Induced Reversal of Electroosmotic Flow in Capillary Electrophoresis," Anal. Chem., vol. 68, pp. 300-305, 1996.
Mahajan, Nupam P. et al., "Novel Mutant Green Fluorescent Protein Protease Substrates Reveal the Activation of Specific Caspases During Apoptosis," Chemistry & Biology, vol. 6, No. 6, pp. 401-409, Jun. 1999.

Maier, Elmar et al., "Automated Array Technologies for Gene Expression Profiling," DDT, vol. 2, No. 8, pp. 315-324, Aug. 1997.
Maldonado-Rodriguez, Rogelio et al., "Mutation Detection by Stacking Hybridization on Genosensor Arrays," Molecular Biotechnology, vol. 11, pp. 13-25, 2000.
Maluf, N., "An Introduction to Microelectromechanical Systems Engineering," Artech House Publishers, Boston London, pp. 42-45, Dec. 1999.
Manz, A. et al., "Micromachining of Monocrystalline Silicon and Glass for Chemical Analysis Systems," Trends in Analytical Chemistry, vol. 10, No. 5, pp. 144-149, 1991.
Marešová, H. et al., "A Chemostat Culture As a Tool for the Improvement of a Recombinant *E. coli* Strain Over-Producing Penicillin G Acylase," Biotechnology and Bioengineering, vol. 75, No. 1, pp. 46-52, Oct. 5, 2001.
Marshall, SID, "Fundamental Changes Ahead for Lab Instrumentation," R&D Magazine, 5 pages, Feb. 1999.
Marsili, Ray, "Lab-On-A-Chip Poised to Revolutionize Sample Prep," R&D Magazine, 5 pages, Feb. 1999.
Marton, Matthew J. et al., "Drug Target Validation and Identification of Secondary Drug Target Effects Using DNA Microarrays," Nature Medicine, vol. 4, No. 11, pp. 1293-1301, Nov. 1998.
Mastrangelo, C. H. et al., "Vacuum-Sealed Silicon Micromachined Incandescent Light Source," IEDM, pp. 503-506, 1989.
Maule, John, "Pulsed-Field Gel Electrophoresis," Molecular Biotechnology, vol. 9, pp. 107-126, 1998.
McDonald, J. Cooper et al., "Fabrication of Microfluidic Systems in Poly(dimethylsiloxane)," Electrophoresis, vol. 21, pp. 27-40, 2000.
McDonald, J. Cooper et al., "Poly(dimethylsiloxane) As a Material for Fabricating Microfluidic Devices," Accounts of Chemical Research, vol. 35, No. 7, pp. 491-499, 2002.
Meiners, Jens-Christian et al., "Direct Measurement of Hydrodynamic Cross Correlations Between Two Particles in an External Potential," Physical Review Letters, vol. 82, No. 10, pp. 2211-2214, Mar. 8, 1999.
Melamed, Myron R. et al., "Flow Cytometry and Sorting," John Wiley & Sons, 32 pages, 1979.
Menchen, Steve et al., "Flowable Networks As DNA Sequencing Media in Capillary Columns," Electrophoresis, vol. 17, pp. 1451-1459, 1996.
Moldavan, Andrew, "Photo-Electric Technique for the Counting of Microscopical Cells," Science, vol. 80, No. 2069, pp. 188-189, Aug. 24, 1934.
Monod, Jacques, "The Growth of Bacterial Cultures," Annual Review of Microbiology, vol. III, pp. cover and 371-394, 1949.
Muller, Richard S. et al., "Surface-Micromachined Microoptical Elements and Systems," Proceedings of the IEEE, vol. 86, No. 8, pp. 1705-1720, Aug. 1998.
Murray, Vincent et al., "Detection of Polymorphisms Using Thermal Cycling With a Single Oligonucleotide on a DNA Sequencing Gel," Human Mutation, vol. 2, pp. 118-122, 1993.
Nagai, Yasuo et al., "A Fluorescent Indicator for Visualizing cAMP-Induced Phosphorylation In Vivo," Nature Biotechnology, vol. 18, pp. 313-316, Mar. 2000.
Nakamura, Yusuke et al., "Variable Number of Tanden Repeat (VNTR) Markers for Human Gene Mapping," Science, vol. 235, pp. 1616-1622, Mar. 27, 1987.
Nakano et al., "High Speed Polymerase Chain Reaction in Constant Flow," Biosci. Biotech. Biochem., 58(2), pp. 349-352, 1994.
New Objective, Inc., "What Is Electrospray," www.newobjective.com/electrospray/electrospray.html, 4 pages, 1999.
Ng, Jessamine M. K. et al., "Components for Integrated Poly(Dimethylsiloxane) Microfluidic Systems," Electrophoresis, vol. 23, pp. 3461-3473, 2002.
Nielsen, Jens et al., Bioreaction Engineering Principles, Second Edition, pp. 2 cover pages and 42-45, 2003.
Nolan, John P. et al., "The Emergence of Flow Cytometry for Sensitive, Real-Time Measurements of Molecular Interactions," Nature Biotechnology, vol. 16, pp. 633-638, Jul. 1998.
Novick, Aaron et al., "Description of the Chemostat," Science, vol. 112, pp. 715-716, Dec. 15, 1950.

(56) References Cited

OTHER PUBLICATIONS

Novick, Aaron et al., "Experiments With the Chemostat on Spontaneous Mutations of Bacteria," Proc. N. A. S., vol. 36, pp. 708-719, 1950.

Oakley and Knight, "Adaptive dynamic relaxation algorithm for non-linear hyperelastic structures", *Computer Methods in Applied Mechanics and Engineering*, 126:67-89 (1995).

Ogden, "Elastic Deformations of Rubberlike Solids", in *Mechanics of Solids*, pp. 499-537 (1982).

Oleschuk, Richard D. et al., "Analytical Microdevices for Mass Spectrometry," Trends in Analytical Chemistry, vol. 19, No. 6., pp. 379-388, 2000.

Olsson, Anders et al., "Simulation Studies of Diffuser and Nozzle Elements for Valve-Less Micropumps," Transducers '97, 1997 International Conference on Solid-State Sensors and Actuators, Chicago, Illinois, pp. 1039-1042, Jun. 16-19, 1997.

O'Reilly, Marie-Anne J. et al., "The Technique of Pulsed Field Gel Electrophoresis and Its Impact on Molecular Immunology," Journal of Immunological Methods, vol. 131, pp. 1-13, 1990.

Pandolfi et al., "Time-Discretized Variational Formulation of Non-Smooth Frictional Contact," International Journal for Numerical Methods in Engineering, vol. 53, No. 8, pp. 1801-1829, 2002.

Parker, Gregory J. et al., "Development of High Throughput Screening Assays Using Fluorescence Polarization: Nuclear Receptor-Ligand-Binding and Kinase/Phophatase Assays," Journal of Biomolecular Screening, vol. 5, No. 2, pp. 77-88, 2000.

Persson, Bjorn et al., "Analysis of Oligonucleotide Probe Affinities Using Surface Plasmon Resonance: A Means for Mutational Scanning," Analytical Biochemistry, vol. 246, pp. 34-44, 1997.

Pethig, Ronald et al., "Applications of Dielectrophoresis in Biotechnology," Tibtech, vol. 15, pp. 426-432, Oct. 1997.

Petty, Jeffrey T. et al., "Characterization of DNA Size Determination of Small Fragments by Flow Cytometry," Anal. Chem., vol. 67, pp. 1755-1761, 1995.

Phillips, W.C. and Rayment, I. "A systematic method for aligning double focusing mirrors." Methods in Enzymology, 1985, vol. 114 (Wyckoff, Hirs and Timasheff, eds.), 316-329, Academic Press.

Poplawski, M. E. et al., "A Simple Packaging Process for Chemical Sensors," Solid-State Sensor and Actuator Workshop, Hilton Head, South Carolina, pp. 25-28, Jun. 13-16, 1994.

Qin, Dong et al., "Photolithography With Transparent Reflective Photomasks," J. Vac. Sci. Technol. B, vol. 16, No. 1, pp. 98-103, Jan. 1998.

Qin, Dong et al., "Elastomeric Light Valves," Adv. Mater., vol. 9, No. 5, pp. 407-410, 1997.

Qu, Mingbo et al., "Toxicity and Biodegradation of Formaldehyde in Anaerobic Methanogenic Culture," Biotechnology and Bioengineering, vol. 55, No. 5, pp. 727-736, Sep. 5, 1997.

Quake, Stephen R. et al., "From Micro- to Nanofabrication With Soft Materials," Science, vol. 290, pp. 1536-1540, Nov. 24, 2000.

Rapp, R. et al., "LIGA Micropump for Gases and Liquids," Sensors and Actuators A, vol. 40, pp. 57-61, Jan. 1994.

Roberts, Richard W. et al., "RNA-Peptide Fusions for the In Vitro Selection of Peptides and Proteins," Proc. Natl. Acad. Sci. USA, vol. 94, pp. 12297-12302, Nov. 1997.

Rondon et al., "Cloning the Soil Metagenome: A Strategy for Accessing the Genetic and Functional Diversity of Uncultured Microorganisims," *Applied and Environmental Microbiology*, (Jun. 2000), 66, 6:2541-2547.

Rotman, Boris, "A Simplified Device for Continuous Growth of Microorganisms," Journal of Bacteriology, vol. 70, pp. 485-486, 1955.

Rouhi, Maureen, "Sizing, Sorting DNA One Piece At a Time," C&EN, pp. 5-6, Jan. 11, 1999.

Roylance, Lynn Michelle et al., "A Batch-Fabricated Silicon Accelerometer," IEEE Transactions on Electron Devices, vol. ED-26, No. 12, pp. 1911-1917, Dec. 1979.

Samad, Akhtar et al., "Optical Mapping: A Novel, Single-Molecule Approach to Genomic Analysis," Genome Research, pp. 1-4, 1995.

Sandia National Laboratories, "Electro Microfluidic Dual In-Line Package (EMDIP)," 2 pages, no date.

Sanjoh, Akira et al., "Spatiotemporal Protein Crystal Growth Studies Using Microfluidic Silicon Devices," Journal of Crystal Growth, vol. 196, pp. 691-702, 1999.

Sasserath, J. et al., "Rapid Prototyping and Development of Microfluidic and BioMEMS Devices," IVD Technology, 12 pages, Jun. 2002.

Schasfoort, Richard B. M. et al., "Field-Effect Flow Control for Microfabricated Fluidic Networks," Science, vol. 286, pp. 942-945, Oct. 29, 1999.

Schena, Mark et al., "Quantitative Monitoring of Gene Expression Patterns With a Complementary DNA Microarray," Science, vol. 270, pp. 467-470, Oct. 20, 1995.

Schilling et al., "Cell Lysis and Protein Extraction in a Microfluidic Device with Detection by a Fluorogenic Enzyme Assay", Anal. Chem., 2002, p. 1798-1804, vol. 74.

Scholoss et al., "Biotechnological Prospects from Metagenomics," *Current Opinion in Biotechnology*, (2003), 14:303-310.

Schomburg, W. K. et al., "Fabrication of Polymer Microcomponents With the AMANDA-Process," New Materials and Directions, Eurosensors XII, pp. 711-714, Sep. 13-16, 1998.

Schueller, Olivier J. A. et al., "Fabrication of Glassy Carbon Microstructures by Soft Lithography," Sensors and Actuators A, vol. 72, pp. 126-139, 1999.

Schullek, John R., "A High-Density Screening Format for Encoded Combinatorial Libraries: Assay Miniaturization and Its Application to Enzymatic Reactions," Analytical Biochemistry, vol. 246, pp. 20-29, 1997.

Schwartz, David C. et al., "Optical Mapping Approaches to Molecular Genomics," Current Opinion in Biotechnology, vol. 8, pp. 70-74, 1997.

Seethala, Ramakrishna et al., "A Fluorescence Polarization Competition Immunoassay for Tyrosine Kinases," Analytical Biochemistry, vol. 255, pp. 257-262, 1998.

Shevchenko, Andrej et al., "Rapid 'de Novo' Peptide Sequencing by a Combination of Nanoelectospray, Isotopic Labeling and a Quadrupole/Time-Of-Flight Mass Spectometer," Rapid Communications in Mass Spectrometry, vol. 11, pp. 1015-1024, 1997.

Shinohara, Jun et al., "A High Pressure-Resistance Micropump Using Active and Normally-Closed Valves," IEEE, pp. 86-91, 2000.

Shoji, Shuichi et al., "Smallest Dead Volume Microvalves for Integrated Chemical Analyzing Systems," Transducers '91, 1991 International Conference on Solid-State Sensors and Actuators, San Francisco, California, pp. cover, 1052-1055, 1991.

Shoji, Shuichi, "Fluids for Sensor Systems," Topics in Current Chemistry, vol. 194, pp. 163-188, 1998.

Shuler, Michael L. et al., "Chapter 6—How Cells Grow," Bioprocess Engineering Basic Concepts, Second Edition, pp. 2 cover pages and 155-200, 2002.

Sklar, Larry A. et al., Sample Handling for Kinetics and Molecular Assembly in Flow Cytometry, SPIE, vol. 3256, pp. 144-153, 1998.

Smits, J.G., "Piezoelectric Micropump With Three Valves Working Peristaltically," Sensors and Actuators, vol. A21-A23, pp. 203-206, 1990.

Sohn, L. L. et al., "Capacitance Cytometry: Measuring Biological Cells One by One," PNAS, vol. 97, No. 20, pp. 10687-10690, Sep. 26, 2000.

Sosnowski, Ronald G. et al., "Rapid Determination of Single Base Mismatch Mutations in DNA Hybrids by Direct Electric Field Control," Proc. Natl. Acad. Sci. USA, vol. 94, pp. 1119-1123, Feb. 1997.

Southern, E. M. et al., "Analyzing and Comparing Nucleic Acid Sequences by Hybridization to Arrays of Oligonucleotides: Evaluation Using Experimental Models," Genomics, vol. 13, pp. 1008-1017, 1992.

Spellman, Paul T. et al., "Comprehensive Identification of Cell Cycle-Regulated Genes of the Yeast *Saccharomyces cerevisiae* by Microarray Hybridization," Molecular Biology of the Cell, vol. 9, pp. 3273-3297, Dec. 1998.

Spicer, C. C., "The Theory of Bacterial Constant Growth Apparatus," Biometrics, pp. 225-230, Jun. 1955.

Stemmer, Willem P. C. et al., "Rapid Evolution of a Protein in vitro by DNA Shuffling," Nature, vol. 370, pp. 389-390, Aug. 4, 1994.

(56) References Cited

OTHER PUBLICATIONS

Stomakhin, Andrey A. et al., "DNA Sequence Analysis by Hybridization With Oligonucleotide Microchips: MALDI Mass Spectrometry Identification of 5mers Contiguously Stacked to Microchip Oligonucleotides," Nucleic Acids Research, vol. 28, No. 5, pp. 1193-1198, 2000.
Studer et al., "Nanoembossing of thermoplastic polymers for microfluidic applications", Applied Physics Letters 80:3614-16 (2002).
Sussman, Norman L. et al., "The Predictive Nature of High-Throughput Toxicity Screening Using a Human Hepatocyte Cell Line," Cell Notes, Issue 3, pp. 7-10, 2002.
Swart, Remco et al., "Recent Progress in Open Tubular Liquid Chromatography," Trends in Analytical Chemistry, vol. 16, No. 6, pp. 332-342, 1997.
Sweet, Richard G., "Flow Sorters for Biologic Cells," pp. 177-189, no date.
Takahashi, Akiyuki et al., "Measurement of Intracellular Calcium," Physiological Reviews, vol. 79, No. 4, pp. 1089-1125, Oct. 1999.
Tatari, Zohreh et al., "HLA-Cw Allele Analysis by PCR-Restriction Fragment Length Polymorphism: Study of Known and Additional Alleies," Proc. Natl. Acad. Sci. USA, vol. 92, pp. 8803-8807, Sep. 1995.
Tawfik, Dan S. et al., "Man-Made Cell-Like Compartments for Molecular Evolution," Nature Biotechnology, vol. 16, pp. 652-656, Jul. 1998.
Taylor, Anne M. et al., "Microfluidic Multicompartment Device for Neuroscience Research," Langmuir, vol. 19, pp. 1551-1556, 2003.
Telleman et al., "Cell Sorting in Microfluidic Systems", Proceedings of the uTAS '98 Workshop, Banff, Canada, Oct. 1998, p. 39-44.
Terry, Stephen C. et al., "A Gas Chromatographic Air Analyzer Fabricated on a Silicon Wafer," IEEE Transactions on Electron Devices, vol. ED-26, No. 12, pp. 1880-1886, Dec. 1979.
Thompson, H. Garrett R. et al., "Identification and Confirmation of a Module of Coexpressed Genes," Genome Research, vol. 12, pp. 1517-1522, 2002.
Thompson, L. F. et al., "Introduction to Microlithography," 185th Meeting of the American Chemical Society, Seattle, WA, pp. 2 cover pages, 1-13, Mar. 20-25, 1983.
Thorsen, Todd et al., "Dynamic Pattern Formation in a Vesicle-Generating Microfluidic Device," Physical Review Letters, vol. 86, No. 18, pp. 4163-4166, Apr. 30, 2001.
Thorsen, Todd et al., "Microfluidic Large-Scale Integration," Science, vol. 298, No. 5593, pp. 580-584, Oct. 18, 2002.
Thorsen, Todd, "Microfluidic Technologies for High-Throughput Screening Applications," http://resolver.caltech.edu/CaltechETD:etd-12012002-092026, California Institute of Technology, Sep. 23, 2002.
Todd, Paul et al., "Chapter 12—Cell Electrophoresis," Flow Cytometry and Sorting, John Wiley & Sons, pp. 5 cover pages and 217-229, 1979.
Toussaint et al., "A New Evaluation of Our Life-Support System," EMBO Reports, <<http//www.nature.com/cgi-taf/DynaPage.taf?file=/embor/journal/v4/n9/full/embor930.html>>, 13 pages total.
Tufte, O. N. et al., "Silicon Diffused-Element Piezoresistive Diaphragms," Journal of Applied Physics, vol. 33, No. 11, pp. 3322-3327, Nov. 1962.
Tyagi et al., "Molecular Beacons: Probes that Fluoresce upon Hybridization," Nature Biotechnology, 14:303-308 (1996).
Ullmann's Encyclopedia of Industrial Chemistry, Sections 6 to 6.3, Topic: Carbon Black, Sixth Edition, 7 pages, 1999.
Umdanhowar, P. B. et al., "Monodisperse Emulsion Generation Via Drop Break Off in a Coflowing Stream," Langmuir, vol. 16, pp. 347-351, 2000.
Underwood et al., "Dynamic relaxation", in *Computational Methods for Transient Dynamic Analysis*, Belytschko and Hughes, eds., pp. 245-265, Elsevier Science Publishers, Amsterdam (1983).
Unger, M et al., "Single-Molecule Fluorescence Observed With Mercury Lamp Illumination," Biotechniques, vol. 27, No. 5, pp. 1008-1014, Nov. 1999.
Unger, Marc A. et al., "Monolithic Microfabricated Valves and Pumps by Multilayer Soft Lithography," Science, vol. 288, pp. 113-116, Apr. 7, 2000.
Vahey, Paul G. et al., "Development of a Positive Pressure Driven Micro-Fabricated Liquid Chromatographic Analyzer Through Rapid-Prototyping With Poly(dimethylsiloxane) Optimizing Chromatographic Efficiency With Sub-Nanoliter Injections," Talanta, vol. 51, pp. 1205-1212, 2000.
Van Dam, R. Michael et al., "Gene Expression Analysis With Universal n-mer Arrays," Genome Research, vol. 12, pp. 145-152, 2002.
Van De Pol, F.C.M. et al., "A Thermo-Pneumatic Actuation Principle for a Microminiature Pump and Other Micromechanical Devices," Sensors and Actuators, vol. 17, Nos. 1-2, pp. 139-143, May 3, 1989.
Van De Pol, F.C.M. et al., "Micro Liquid Handling Devices—A Review," Micro Systems Technologies, vol. 90, pp. 799-805, 1990.
Van Den Berg, A. et al., "Micro Total Analysis Systems," Proceedings of the μTAS '94 Workshop, University of Twente, The Netherlands, 17 pages, Nov. 21-22, 1994.
Van Der Woerd, Mark et al., "Lab-On-A-Chip Based Protein Crystallization," National Aeronautics and Space Administration and Caliper, pp. 1-27, Oct. 25, 2001.
Van Der Woerd, Mark et al., "The Promise of Macromolecular Crystallization in Microfluidic Chips," Journal of Structural Biology, vol. 142, pp. 180-187, 2003.
Van Dilla, M. A. et al., "Cell Microfluorometry: A Method for Rapid Fluorescence Measurement," Science, vol. 163, pp. 1213-1214, Mar. 14, 1969.
Van Orden, Alan et al., "High-Throughput Flow Cytometric DNA Fragment Sizing," Anal. Chem., vol. 72, No. 1, pp. 37-41, Jan. 1, 2000.
Veronese, F. M. et al., "Influence of PEGylation on the Release of Low and High Molecular-Weight Proteins From PVA Matrices," Journal of Bioactive and Compatible Polymers, vol. 14, pp. 315-330, Jul. 1999.
Veronese, Francesco M., "Peptide and Protein PEGylation: A Review of Problems and Solutions," Biomaterials, vol. 22, pp. 405-417, 2001.
Verpoorte, Elisabeth M. J. et al., "Three-Dimensional Micro Flow Manifolds for Miniaturized Chemical Analysis Systems," J. Micromech. Microeng., vol. 7, pp. 246-256, 1994.
Vieider, Christian et al., "A Pneumatically Actuated Micro Valve With a Silicon Rubber Membrane for Integration With Fluid Handling Systems," Transducers '95, 8th International Conference on Solid-State Sensors and Actuators and Eurosensors IX, Stockholm, Sweden, pp. 284-286, Jun. 25-29, 1995.
Vogelstein, Bert et al., "Digital PCR," Proc. Natl. Acad. Sci. USA, vol. 96, pp. 9236-9241, Aug. 1999.
Volkmuth, W. D. et al., DNA Electrodiffusion in a 2D Array of Posts, Physical Review Letters, vol. 72, No. 13, pp. 2117-2120, Mar. 28, 1994.
Volkmuth, W. D. et al., "DNA Electrophoresis in Microlithographic Arrays," Nature, vol. 358, pp. 600-602, Aug. 13, 1992.
Ward, Keith B. et al., "Automatic Preparation of Protein Crystals Using Laboratory Robotics and Automated Visual Inspection," Journal of Crystal Growth, vol. 90, pp. 325-339, 1988.
Washizu, Masao et al., "Molecular Dielectrophoresis of Biopolymers," IEEE Transactions on Industry Applications, vol. 30, No. 4, pp. 835-843, Jul. 1994.
Waters, L. C. et al., "Microchip Devices for Cell Lysis, Multiplex PCR Amplification, and Electrophoretic Sizing," Analytical Chemistry, vol. 70, No. 1, pp. 158-162, Jan. 1, 1998.
Webster, J. R. et al., "Monolithic Capillary Gel Electrophoresis Stage With On-Chip Detector," IEEE, pp. 491-496, 1996.
Weigl, Bernhard H., "Microfluidics-Based Lab-On-A-Chip Systems," IVD Technology Magazine, 8 pages, Nov./Dec. 2000.
Whelen, A. Christian et al., "The Role of Nucleic Acid Amplification and Detection in the Clinical Microbiology Laboratory," Annu. Rev. Microbiol., vol. 50, pp. 349-373, 1996.
Whitesides, George M. et al., "Flexible Methods for Microfluidics," Physics Today, pp. 42-48, Jun. 2001.

(56) References Cited

OTHER PUBLICATIONS

Whitesides, George M. et al., "Soft Lithography in Biology and Biochemistry," Annu. Rev. Biomed. Eng., vol. 3, pp. 335-373, 2001.
Wiebe, Marilyn G. et al., "Evolution of a Recombinant (Gucoamylase-Producing) Strain of *Fusarium venenatum* A3/5 in Chemostat Culture," Biotechnology and Bioengineering, vol. 73, No. 2, pp. 146-156, Apr. 20, 2001.
Wilbur, James L. et al., "Lithographic Molding: A Convenient Route to Structures With Sub-Micrometer Dimensions," Adv. Mater., vol. 7, No. 7, pp. 649-652, 1995.
Wilm, Matthias et al., "Femtomole Sequencing of Proteins From Polyacrylamide Gels by Nano-Electrospray Mass Spectrometry," Nature, vol. 379, pp. 466-469, Feb. 1, 1996.
Wooley et al., "Functional Integration of PCR Amplification and Capillary Electrophoresis in a Microfabricated DNA Analysis Device," Anal. Chem., vol. 68, pp. 4081-4086, 1996.
Wooley, A. T. et al., "Capillary Electrophoresis Chips With Integrated Electrochemical Detection," Analytical Chemistry, vol. 70, No. 4, pp. 684-688, Feb. 15, 1998.
Wu, Chunhung et al., "Viscosity-Adjustable Block Copolymer for DNA Separation by Capillary Electrophoresis," Electrophoresis, vol. 19, pp. 231-241, 1998.
Wu, Hongkai et al., "Fabrication of Complex Three-Dimensional Microchannel Systems in PDMS," J. Am. Chem. Soc., vol. 125, No. 2, pp. 554-559, 2003.
Wu, Shuyun et al., "MEMS Flow Sensors for Nano-Fluidic Applications," Sensors and Actuators A, vol. 89, pp. 152-158, 2001.
Xia, Younan et al., "Micromolding of Polymers in Capillaries: Applications in Microfabrication," Chem. Mater., vol. 8, No. 7, pp. 1559-1566, 1996.
Xia, Younan et al., "Complex Optical Surfaces Formed by Replica Molding Against Elastomeric Masters," Science, vol. 273, pp. 347-349, Jul. 19, 1996.
Xia, Younan et al., "Reduction in the Size of Features of Patterned SAMs Generated by Microcontact Printing With Mechanical Compression of the Stamp," Adv. Mater., vol. 7, No. 5, pp. 471-473, 1995.
Xia, Younan et al., "Soft Lithography," Angew. Chem. Int. Ed., vol. 37, pp. 551-575, 1998.
Xu, Bing et al., "Making Negative Poisson's Ratio Microstructures by Soft Lithography," Adv. Mater., vol. 11, No. 14, pp. 1186-1189, 1999.
Xu, Jingdong et al., "Room-Temperature Imprinting Method for Plastic Microchannel Fabrication," Analytical Chemistry, vol. 72, No. 8, pp. 1930-1933, Apr. 15, 2000.
Xu, Xiang et al., "Detection of Programmed Cell Death Using Fluorescence Energy Transfer," Nucleic Acids Research, vol. 26, No. 8, pp. 2034-2035, 1998.
Xue, Qifeng et al., "Integrated Multichannel Microchip Electrospray Ionization Mass Spectrometry: Analysis of Peptides From On-Chip Tryptic Digestion of Melittin," Rapid Communications in Mass Spectrometry, vol. 11, 1253-1256, 1997.
Xue, Qifeng et al., "Multichannel Microchip Electrospray Mass Spectrometry," Analytical Chemistry, vol. 69, No. 3, pp. 426-430, Feb. 1, 1997.
Yang, T. J. et al., "An Apertureless Near-Field Microscope for Fluorescence Imaging," Applied Physics Letters, vol. 76, No. 3, pp. 378-380, Jan. 17, 2000.
Yang, Xing et al., "A Low Power MEMS Silicone/Parylene Valve," Solid-State Sensor and Actuator Workshop, Hilton Head Island, South Carolina, 4 pages, Jun. 7-11, 1998.
Yang, Xing et al., "A MEMS Thermopneumatic Silicone Membrane Valve," IEEE 10th Annual International Workshop of Micro Electro Mechanical Systems, Nagoya, Japan, pp. cover, 114-118, Jan. 26-30, 1997.
Yazdi, Navid et al., "Micromachined Inertial Sensors," Proceedings of IEEE, vol. 86, No. 8, pp. 1640-1659, Aug. 1998.
Yershov, Gennady et al., "DNA Analysis and Diagnostics on Oligonucleotide Microchips," Proc. Natl. Acad. Sci. USA, vol. 93, pp. 4913-4918, May 1996.
Yokobayashi, Yohei et al., "Evolutionary Design of Genetic Circuits and Cell-Cell Communications," Advances in Complex Systems, vol. 6, No. 1, pp. 37-45, 2003.
Young, A. M. et al., "Contoured Elastic-Membrane Microvalves for Microfluidic Network Integration," Journal of Biomechanical Engineering, vol. 121, pp. 2-6, Feb. 1999.
Zaccolo, Manuela et al., "A Genetically Encoded, Fluorescent Indicator for Cyclic AMP in Living Cells," Nature Cell Biology, vol. 2, pp. 25-29, Jan. 2000.
Zalipsky, Samuel, "Chemistry of Polyethyelene Glycol Conjugates With Biologically Active Molecules," Advanced Drug Delivery Reviews, vol. 16, pp. 157-182, 1995.
Zdeblick, Mark J. et al., "A Microminiature Electric-To-Fluidic Valve," Transducers '87, Proceedings of the 4th International Conference on Solid-State Sensors and Actuators, reprinted in Micromechanics and MEMS Classic and Seminal Papers to 1990, pp. 2 cover pages, 437-439, Jun. 1987.
Zengerle, R. et al., "A Micro Membrane Pump With Electrostatic Actuation," Micro Electro Mechanical Systems '92, Travemünde, Germany, pp. 19-24, Feb. 4-7, 1992.
Zengerle, R. et al., "Performance Simulation of Microminiaturized Membrane Pumps," 7th International Conference on Solid-State Sensors and Actuators, Yokohama, Japan, pp. 2 cover pages, 106-109, Jun. 7-10, 1993.
Zhang, B. et al., "Microfabricated Devices for Capillary Electrophoresis-Electrospray Mass Spectrometry," Analytical Chemistry, vol. 71, No. 15, pp. 3258-3264, Aug. 1, 1999.
Zhao, Zhan, et al., "An Integrated Biochip Design and Fabrication," Proceedings of SPIE, vol. 4936, pp. 321-326, 2002.
Zheng, Bo et al., "A Droplet-Based, Composite PDMS/Glass Capillary Microfluidic System for Evaluating Protein Crystallization Conditions by Microbatch and Vapor-Diffusion Methods With On-Chip X-Ray Diffraction," Angew. Chem., pp. 1-4, 2004.
Ziauddin, Junaid et al., "Microarrays of Cells Expressing Defined cDNAs," Nature, vol. 411, pp. 107-110, May 3, 2001.

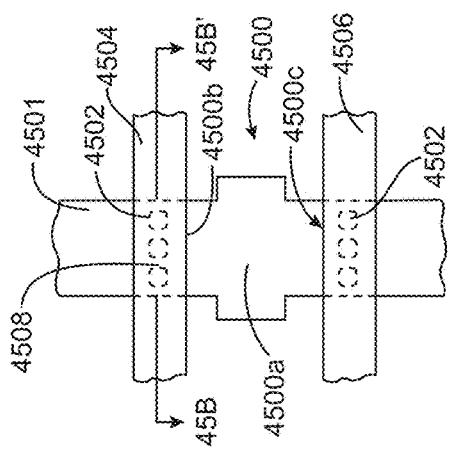
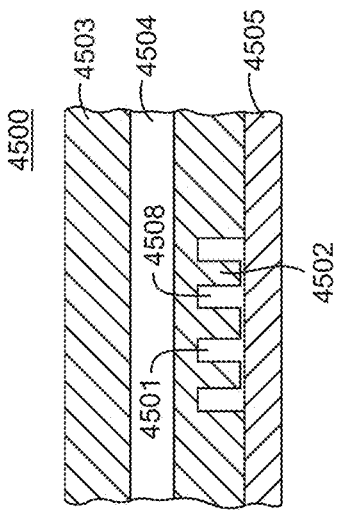
FIG. 19A
FIG. 19B

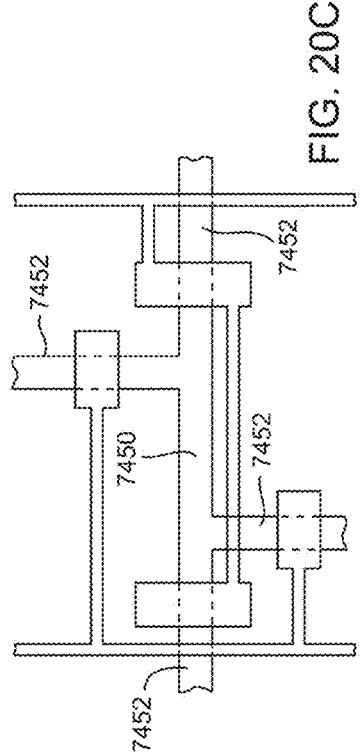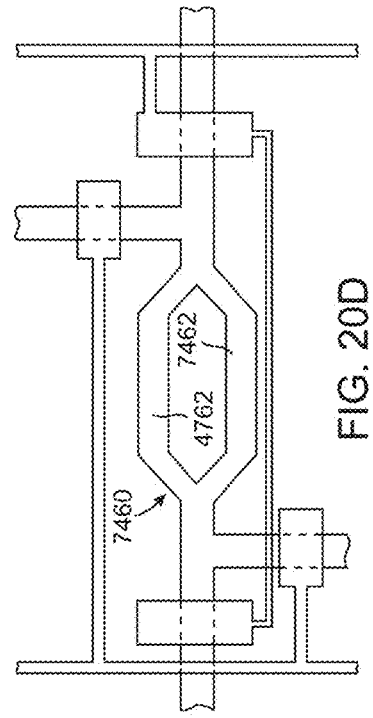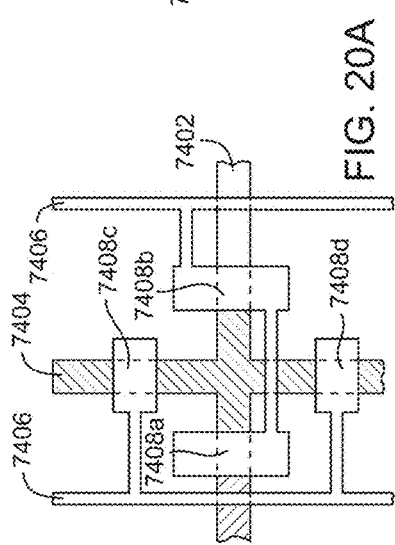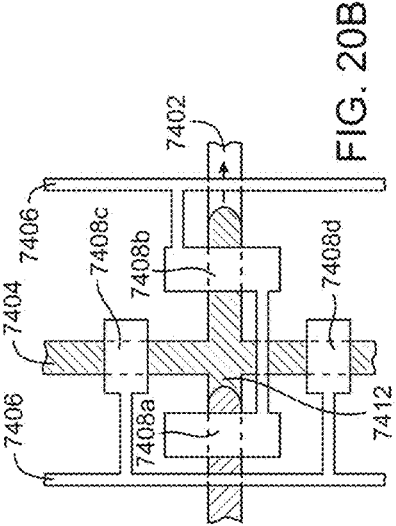

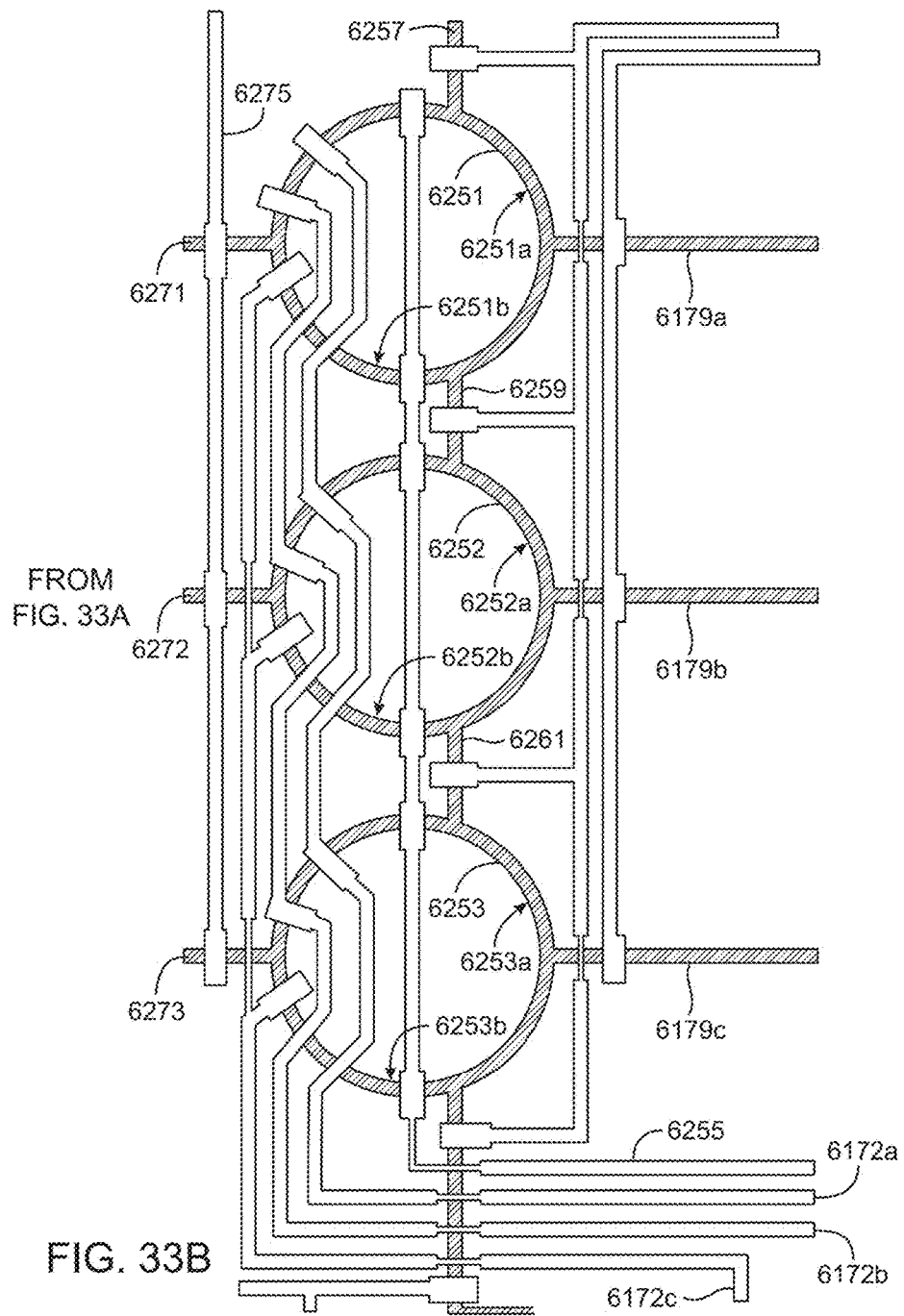

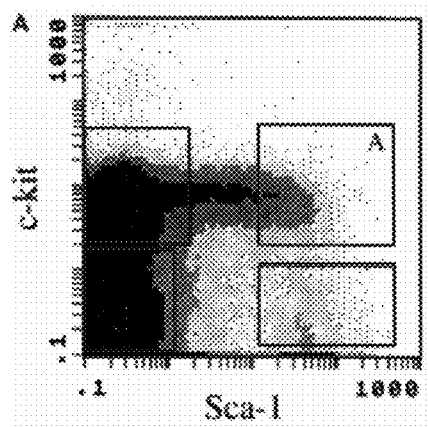
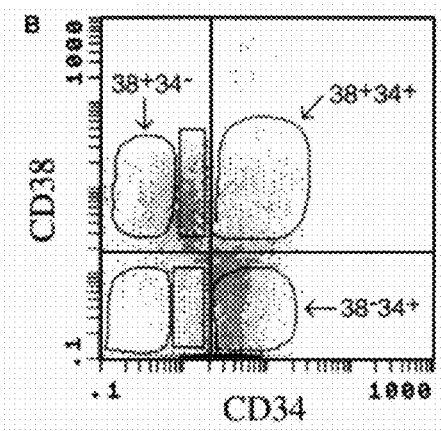
FIG. 41A        FIG. 41B
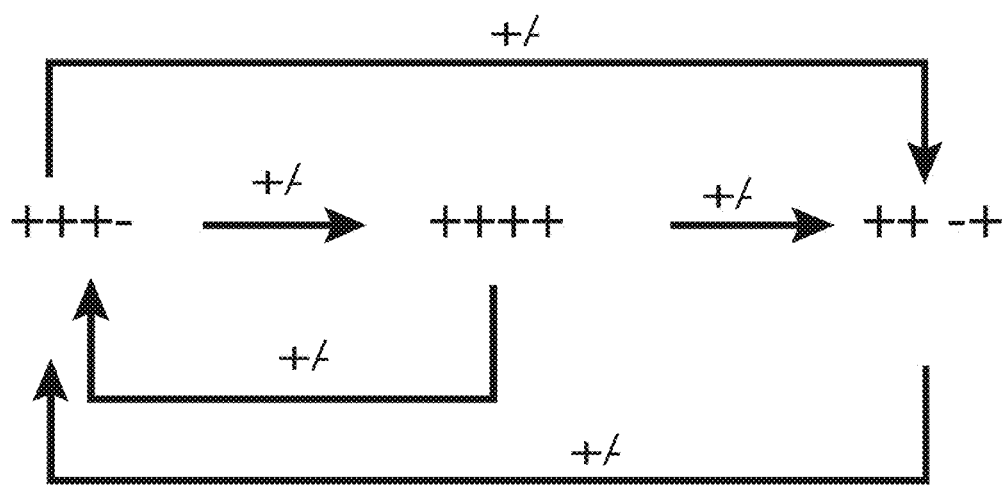
FIG. 42

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic Forward Primer

<400> SEQUENCE: 1
ggtggttatt ggcatcattg c                                            21

<210> SEQ ID NO 2
<211> LENGTH: 20
<212> TYPE: DNA
<213> ORGANISM: Artificial Sequence
<220> FEATURE:
<223> OTHER INFORMATION: Synthetic Reverse Primer

<400> SEQUENCE: 2
gttatcccaa cccggtgtca                                              20

APPARATUS FOR PREPARING CDNA LIBRARIES FROM SINGLE CELLS

CROSS-REFERENCE TO RELATED APPLICATIONS

This application is a continuation of U.S. patent application Ser. No. 14/494,284, filed on Sep. 23, 2014, which is a continuation of U.S. patent application Ser. No. 10/678,946, filed on Oct. 2, 2003 (now U.S. Pat. No. 8,871,446), which claims priority from U.S. provisional patent application No. 60/415,407, filed Oct. 2, 2002; U.S. provisional patent application No. 60/444,022, filed Jan. 31, 2003; U.S. provisional patent application No. 60/494,377, filed Aug. 11, 2003; and U.S. provisional patent application No. 60/494,388, filed Aug. 11, 2003. Each of these previously filed patent applications are hereby incorporated by reference for all purposes.

STATEMENT AS TO RIGHTS TO INVENTIONS MADE UNDER FEDERALLY SPONSORED RESEARCH AND DEVELOPMENT

This invention was made with government support under Grant No. BES-0119493 awarded by the National Science Foundation and under Grant No. DAAD19-00-1-0392 awarded by DARPA. The government has certain rights in the invention.

REFERENCE TO A SEQUENCE LISTING

The Sequence Listing written in file SequenceListing_087159-1031245.txt created on Dec. 2, 2016, 866 bytes, machine format IBM-PC, MS-Windows operating system, is hereby incorporated by reference in its entirety for all purposes.

BACKGROUND OF THE INVENTION

There evidence that in many ecosystems more than 99% of the microbial population resists laboratory cultivation. N. R. Pace, "A Molecular View of Microbial Diversity and the Biosphere", *Science* 276, 734 (1997). This has led to the suggestion that microbial ecosystems in human beings are more complex than previously suspected, and that some or many of the uncultivatable microbes may be infectious agents. D. A. Relman, "The Search for Unrecognized Pathogens", *Science* 284, 1308 (1999).

A substantial number of illnesses resemble infectious disease, and unexplained death or critical illnesses occur in 0.5 persons per 100,000 population. B. A. Perkins et al., "Unexplained Deaths Due to Possibly Infectious Causes in the United States: Defining the Problem and Designing Surveillance and Laboratory Approaches", *Emerging Inject. Dis.* 2, 47 (1996). Many such pathogens resist identification by traditional phenotypic methods, which has led to the development of genotypic methods of pathogen identification.

As a result, the last twenty years have seen a growing list of connections between human disease and previously unsuspected microbial pathogens. TABLE 1 lists examples of human disease and associated microbial pathogens revealed during the past 20 years. All of these infectious agents, except Heliobacter pylori, were first identified directly from clinical specimens using genotypic approaches.

TABLE 1

| Disease | Infectious Agent |
| --- | --- |
| Peptic ulcer disease | *Heliobacter pylori* |
| Non-A, non-B hepatitis | Hepatitis C virus |
| Bacillary angiomatosis | *Bartonella henselae* |
| Whipple's disease | *Tropheryma whippelii* |
| Hantavirus pulmonary syndrome | Sin Nombre virus |
| Kaposi's sarcoma | Kaposi's sarcoma-associated herpesvirus |

Although the human body offers a highly diverse ecosystem for bacteria and viruses, it has been difficult to make precise measurements of diversity and population distribution because many organisms living within it have proven difficult or impossible to culture.

Accordingly, there is a need in the art for techniques and apparatuses for characterizing and analyzing bacteria and viruses existing in a variety of environments.

SUMMARY OF THE INVENTION

Nucleic acid from cells and viruses sampled from a variety of environments may purified and expressed utilizing microfluidic techniques. In accordance with one embodiment of the present invention, individual or small groups of cells or viruses may be isolated in microfluidic chambers by dilution, sorting, and/or segmentation. The isolated cells or viruses may be lysed directly in the microfluidic chamber, and the resulting nucleic acid purified by exposure to affinity beads. Subsequent elution of the purified nucleic acid may be followed by ligation and cell transformation. In one specific application, cell isolation, lysis, and nucleic acid purification may be performed utilizing a highly parallelized microfluidic architecture to create genomic and complementary DNA libraries.

An embodiment of a microfluidic device in accordance with the present invention comprises a first microfluidic chamber, and a first microfluidic channel configured to deliver a sample containing at least one of a virus, a bacterium, and a cell to the first microfluidic chamber. A second microfluidic flow channel is configured to deliver a lysis chemical to the first microfluidic chamber.

An embodiment of a method in accordance with the present invention for purifying nucleic acid, comprises, providing a sample comprising at least one of bacteria, viruses, and cells. A subset of at least one of bacteria, viruses, and cells is physically isolated within a microfluidic chamber. The at least one of the bacteria, viruses, and cells is lysed within the microfluidic chamber. Nucleic acid is flowed from the at least one of the lysed bacteria, viruses, and cells through a second microfluidic chamber containing a nucleic acid purification medium.

An embodiment of a method in accordance with the present invention for microfluidic processing, comprises, providing a sample in parallel to a plurality of microfluidic structures, and controlling processing of the sample by the plurality of microfluidic structures by manipulation of a single control structure in common communication with the plurality of microfluidic structures.

An embodiment of a method in accordance with the present invention for analyzing a sample, comprises, flowing a sample comprising at least one of viruses and cells down a microfluidic channel. Portions of the microfluidic channel are isolated into segments containing a limited number of bacteria, viruses, or cells. At least one of genetic analysis, biochemical analysis, and cloning of genomic DNA or cDNA is performed on the limited number of bacteria, viruses, or cells.

An embodiment of a method in accordance with the present invention for processing nucleic acid, comprises, providing a sample comprising multiple biological entities, and physically isolating an individual biological entity or a subset of the biological entities within a microfluidic chamber. The individual biological entity or the subset of biological entities is lysed, and experimentally manipulatable nucleic acid preparations are obtained from the individual biological entity or the subset of biological entities.

An embodiment of a method in accordance with the present invention for obtaining nucleic acid from a sample of heterogenous biological elements, comprises, providing a sample comprising heterogenous biological elements, and physically isolating an individual biological element or a subset of the biological elements of the sample within a microfluidic chamber. The individual biological element or the subset of biological elements is lysed, and nucleic acid from the individual biological entity or the subset of biological entities is purified. At least a portion of the purified nucleic acid is amplified.

An embodiment of a method in accordance with the present invention for characterizing phylogenetic, gene, and functional diversity exhibited by a specific environment comprising a plurality of biological elements, comprises, providing a sample from the environment comprising heterogenous biological elements. An individual biological element or a subset of the biological elements of the sample is physically isolated within a microfluidic chamber. The individual biological element or the subset of biological elements are lysed to expose nucleic acid present therein. The exposed nucleic acid from the individual biological entity or the subset of biological entities is purified. At least a portion of the purified nucleic acid is amplified, and at least one of phylogenetic, gene, and functional diversity of the amplified portion of the purified nucleic acid is identified.

An embodiment of a method in accordance with the present invention for obtaining genetic information regarding an individual biological element of a complex environmental sample, comprises, providing an environmental sample comprising heterogenous biological elements, and physically isolating within a microfluidic chamber an individual biological element or a subset of the biological elements of the sample. The individual biological element or the subset of biological elements is lysed to expose nucleic acid present therein. The exposed nucleic acid is purified, and at least a portion of the purified nucleic acid is amplified.

These and other embodiments of the present invention, as well as its advantages and features, are described in more detail in conjunction with the text below and attached figures.

BRIEF DESCRIPTION OF THE DRAWINGS

FIGS. 19A and 19B show plan and cross-sectional views illustrating operation of one embodiment of a cell cage structure in accordance with the present invention.

FIGS. 20A to 20D show plan views of operation of a structure utilizing cross-channel injection in accordance with the embodiment of the present invention.

FIG. 33B shows an enlarged view of the region of the microfluidic architecture of FIG. 33 allowing cell transformation with the ligated purified nucleic acid.

FIGS. 41A to 41B show flow cytometric analysis of the surface marker expression profile of murine bone marrow cells.

FIG. 42 illustrates a proposed regulatory network for murine pluripotent hematopoietic stem cells

DETAILED DESCRIPTION OF THE PRESENT INVENTION

I. Microfabrication Overview

The following discussion relates to formation of microfabricated fluidic devices utilizing elastomer materials, as described generally in U.S. patent application Ser. Nos. 10/10/679,997 (now U.S. Pat. No. 7,143,785), filed Sep. 24, 2003), Ser. No. 10/265,473 filed Oct. 4, 2002, Ser. No. 10/118,466 filed Apr. 5, 2002, Ser. No. 09/826,585 filed Apr. 6, 2001, Ser. No. 09/724,784 filed Nov. 28, 2000, and Ser. No. 09/605,520, filed Jun. 27, 2000. These previously-filed patent applications are hereby incorporated by reference for all purposes.

1. Methods of Fabricating

Exemplary methods of fabricating the present invention are provided herein. It is to be understood that the present invention is not limited to fabrication by one or the other of these methods. Rather, other suitable methods of fabricating the present microstructures, including modifying the present methods, are also contemplated.

FIGS. 1 to 7B illustrate sequential steps of a first preferred method of fabricating the present microstructure, (which may be used as a pump or valve). FIGS. 8 to 18 illustrate sequential steps of a second preferred method of fabricating the present microstructure, (which also may be used as a pump or valve).

As will be explained, the preferred method of FIGS. 1 to 7B involves using pre-cured elastomer layers which are assembled and bonded. In an alternative method, each layer of elastomer may be cured "in place". In the following description "channel" refers to a recess in the elastomeric structure which can contain a flow of fluid or gas.

Figure 1:
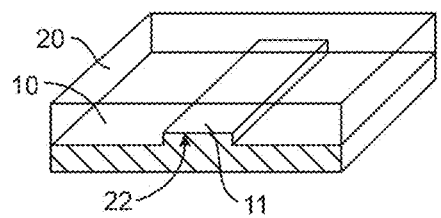
FIG. 1 is an illustration of a first elastomeric layer formed on top of a micromachined mold.

Referring to FIG. 1, a first micro-machined mold 10 is provided. Micro-machined mold 10 may be fabricated by a number of conventional silicon processing methods, including but not limited to photolithography, ion-milling, and electron beam lithography.

As can be seen, micro-machined mold 10 has a raised line or protrusion 11 extending therealong. A first elastomeric layer 20 is cast on top of mold 10 such that a first recess 21 will be formed in the bottom surface of elastomeric layer 20, (recess 21 corresponding in dimension to protrusion 11), as shown.

Figure 2:
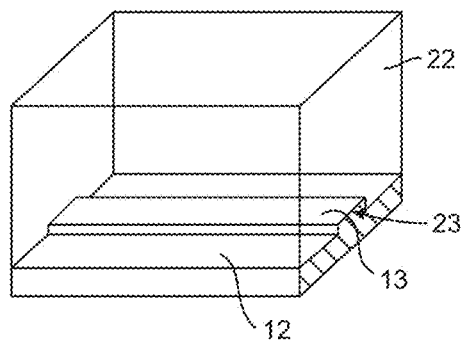
FIG. 2 is an illustration of a second elastomeric layer formed on top of a micromachined mold.

As can be seen in FIG. 2, a second micro-machined mold 12 having a raised protrusion 13 extending therealong is also provided. A second elastomeric layer 22 is cast on top of mold 12, as shown, such that a recess 23 will be formed in its bottom surface corresponding to the dimensions of protrusion 13.

Figure 3:
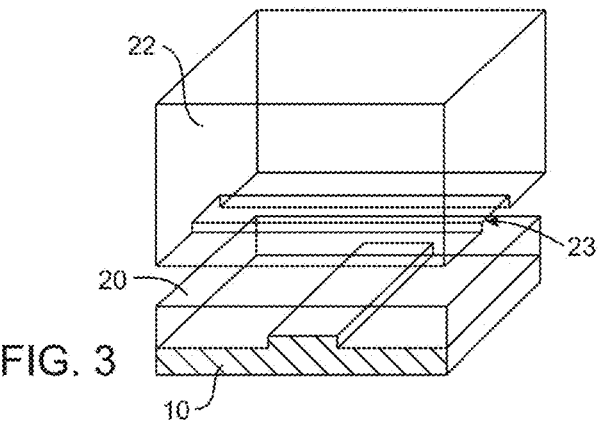
FIG. 3 is an illustration of the elastomeric layer of FIG. 2 removed from the micromachined mold and positioned over the top of the elastomeric layer of FIG. 1.
Figure 4:
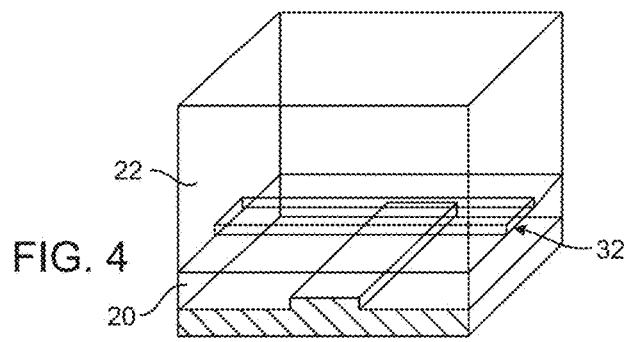
FIG. 4 is an illustration corresponding to FIG. 3, but showing the second elastomeric layer positioned on top of the first elastomeric layer.

As can be seen in the sequential steps illustrated in FIGS. 3 and 4, second elastomeric layer 22 is then removed from mold 12 and placed on top of first elastomeric layer 20. As can be seen, recess 23 extending along the bottom surface of second elastomeric layer 22 will form a flow channel 32.

Figure 5:
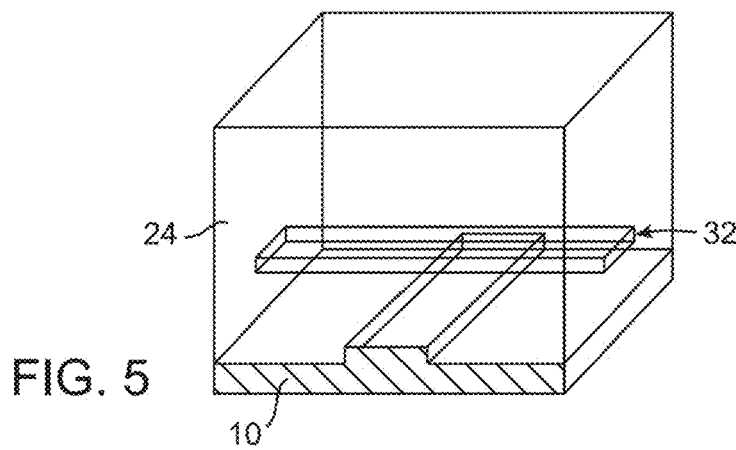
FIG. 5 is an illustration corresponding to FIG. 4, but showing the first and second elastomeric layers bonded together.

Referring to FIG. 5, the separate first and second elastomeric layers 20 and 22 (FIG. 4) are then bonded together to form an integrated (i.e.: monolithic) elastomeric structure 24.

Figure 6:
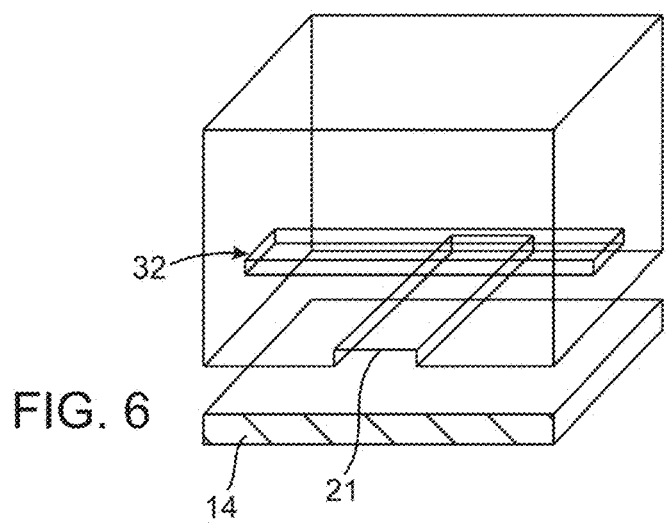
FIG. 6 is an illustration corresponding to FIG. 5, but showing the first micromachined mold removed and a planar substrate positioned in its place.
Figure 7A:
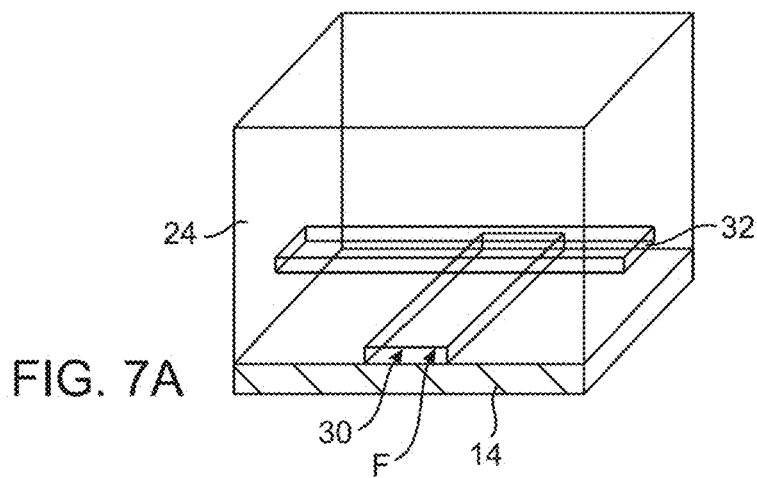
FIG. 7A is an illustration corresponding to FIG. 6, but showing the elastomeric structure sealed onto the planar substrate.
Figure 7B:
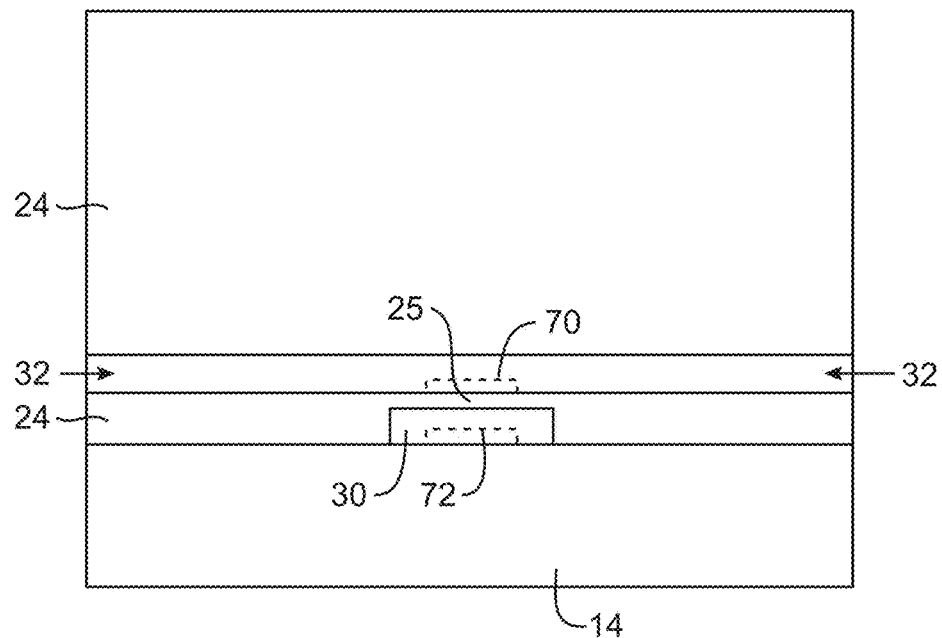
FIG. 7B is a front sectional view corresponding to FIG. 7A, showing an open flow channel.

As can been seen in the sequential step of FIGS. 6 and 7A, elastomeric structure 24 is then removed from mold 10 and positioned on top of a planar substrate 14. As can be seen in FIGS. 7A and 7B, when elastomeric structure 24 has been sealed at its bottom surface to planar substrate 14, recess 21 will form a flow channel 30.

The present elastomeric structures form a reversible hermetic seal with nearly any smooth planar substrate. An advantage to forming a seal this way is that the elastomeric structures may be peeled up, washed, and re-used. In preferred aspects, planar substrate 14 is glass. A further advantage of using glass is that glass is transparent, allowing optical interrogation of elastomer channels and reservoirs. Alternatively, the elastomeric structure may be bonded onto a flat elastomer layer by the same method as described above, forming a permanent and high-strength bond. This may prove advantageous when higher back pressures are used.

As can be seen in FIGS. 7A and 7B, flow channels 30 and 32 are preferably disposed at an angle to one another with a small membrane 25 of substrate 24 separating the top of flow channel 30 from the bottom of flow channel 32.

In preferred aspects, planar substrate 14 is glass. An advantage of using glass is that the present elastomeric structures may be peeled up, washed and reused. A further advantage of using glass is that optical sensing may be employed. Alternatively, planar substrate 14 may be an elastomer itself, which may prove advantageous when higher back pressures are used.

The method of fabrication just described may be varied to form a structure having a membrane composed of an elastomeric material different than that forming the walls of the channels of the device. This variant fabrication method is illustrated in FIGS. 7C-7G.

Figure 7H:
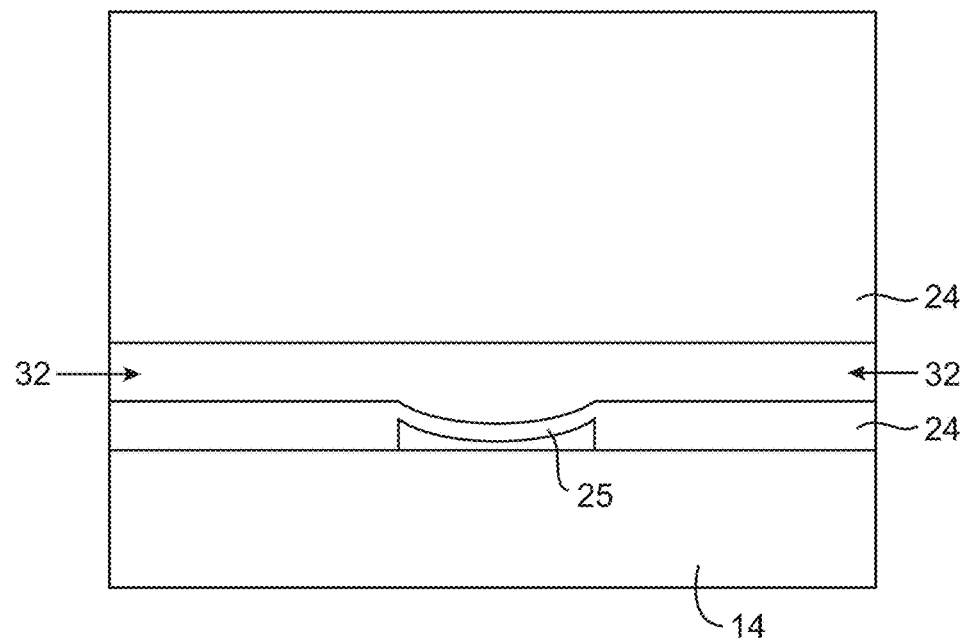
FIG. 7H is a front sectional view showing the valve of FIG. 7B in an actuated state.
Figure 7C:
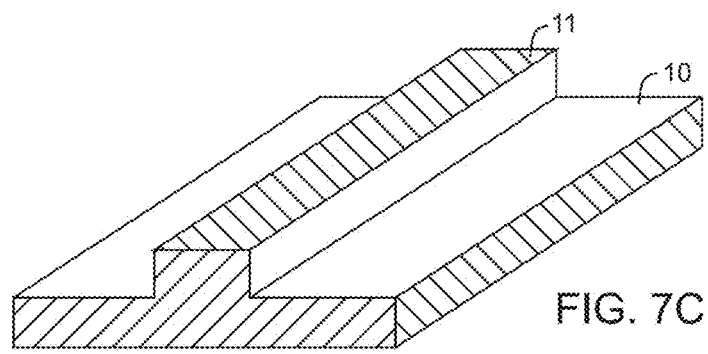
FIGS. 7C-7G are illustrations showing steps of a method for forming an elastomeric structure having a membrane formed from a separate elastomeric layer.
Figure 7D:
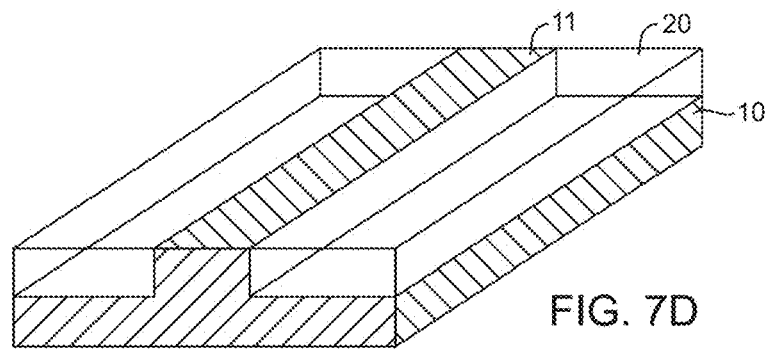

Referring to FIG. 7C, a first micro-machined mold 10 is provided. Micro-machined mold 10 has a raised line or protrusion 11 extending therealong. In FIG. 7D, first elastomeric layer 20 is cast on top of first micro-machined mold 10 such that the top of the first elastomeric layer 20 is flush with the top of raised line or protrusion 11. This may be accomplished by carefully controlling the volume of elastomeric material spun onto mold 10 relative to the known height of raised line 11. Alternatively, the desired shape could be formed by injection molding.

Figure 7E:
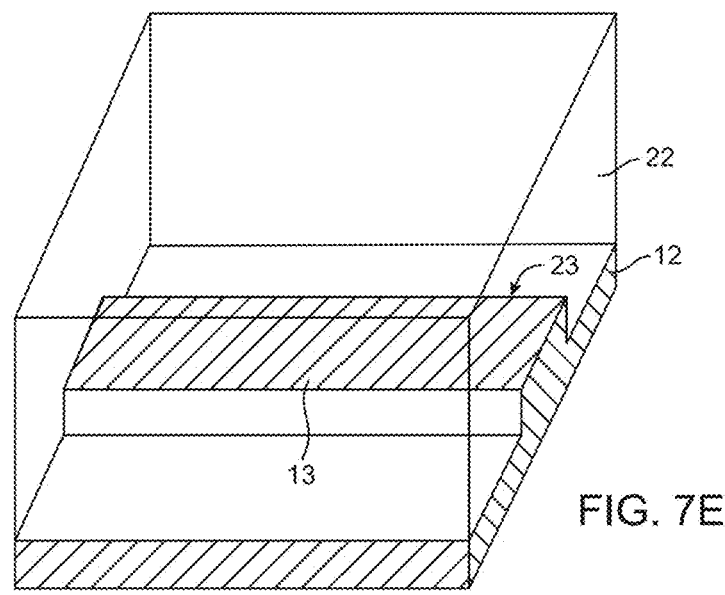

In FIG. 7E, second micro-machined mold 12 having a raised protrusion 13 extending therealong is also provided. Second elastomeric layer 22 is cast on top of second mold 12 as shown, such that recess 23 is formed in its bottom surface corresponding to the dimensions of protrusion 13.

Figure 7F:
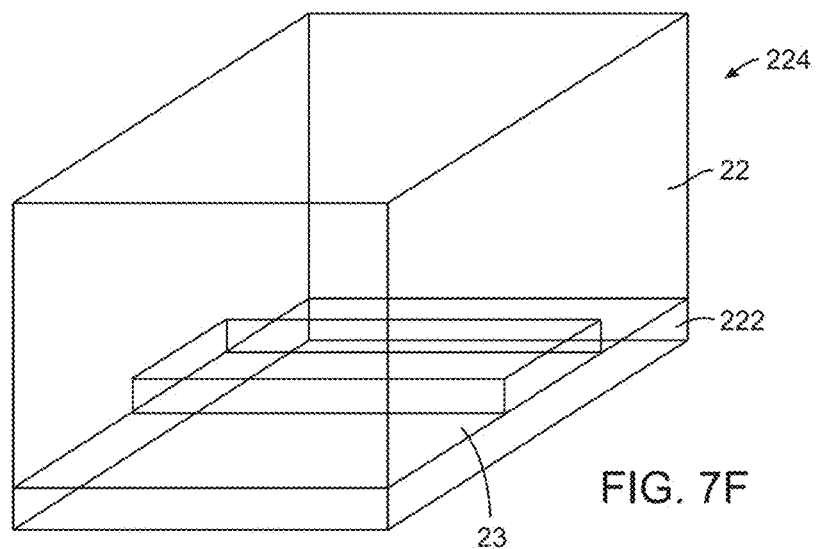

In FIG. 7F, second elastomeric layer 22 is removed from mold 12 and placed on top of third elastomeric layer 222. Second elastomeric layer 22 is bonded to third elastomeric layer 20 to form integral elastomeric block 224 using techniques described in detail below. At this point in the process, recess 23 formerly occupied by raised line 13 will form flow channel 23.

Figure 7G:
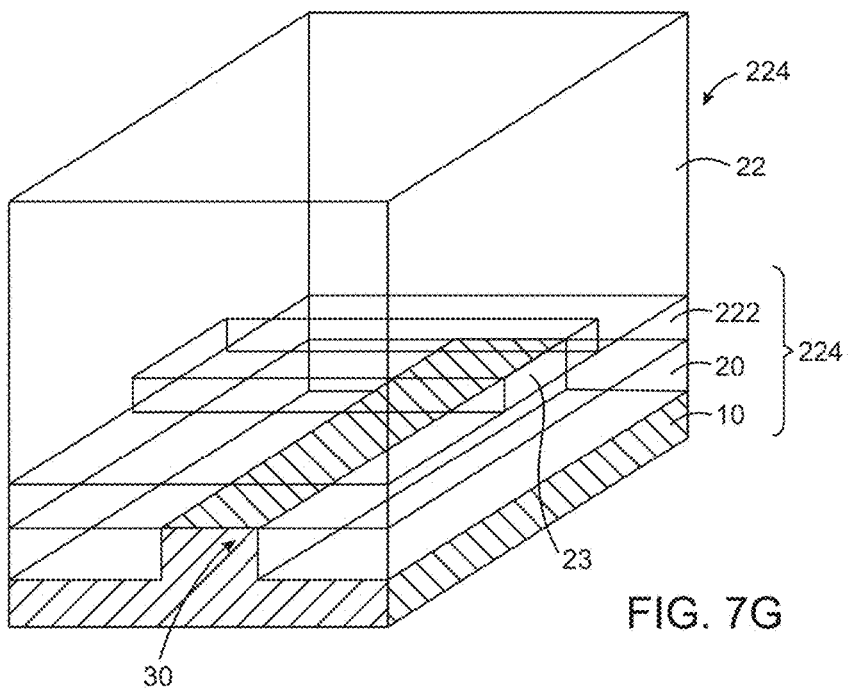

In FIG. 7G, elastomeric block 224 is placed on top of first micro-machined mold 10 and first elastomeric layer 20. Elastomeric block and first elastomeric layer 20 are then bonded together to form an integrated (i.e.: monolithic) elastomeric structure 24 having a membrane composed of a separate elastomeric layer 222.

When elastomeric structure 24 has been sealed at its bottom surface to a planar substrate in the manner described above in connection with FIG. 7A, the recess formerly occupied by raised line 11 will form flow channel 30.

The variant fabrication method illustrated above in conjunction with FIGS. 7C-7G offers the advantage of permitting the membrane portion to be composed of a separate material than the elastomeric material of the remainder of the structure. This is important because the thickness and elastic properties of the membrane play a key role in operation of the device. Moreover, this method allows the separate elastomer layer to readily be subjected to conditioning prior to incorporation into the elastomer structure. As discussed in detail below, examples of potentially desirable condition include the introduction of magnetic or electrically conducting species to permit actuation of the membrane, and/or the introduction of dopant into the membrane in order to alter its elasticity.

While the above method is illustrated in connection with forming various shaped elastomeric layers formed by replication molding on top of a micromachined mold, the present invention is not limited to this technique. Other techniques could be employed to form the individual layers of shaped elastomeric material that are to be bonded together. For example, a shaped layer of elastomeric material could be formed by laser cutting or injection molding, or by methods utilizing chemical etching and/or sacrificial materials as discussed below in conjunction with the second exemplary method.

An alternative method fabricates a patterned elastomer structure utilizing development of photoresist encapsulated within elastomer material. However, the methods in accordance with the present invention are not limited to utilizing photoresist. Other materials such as metals could also serve as sacrificial materials to be removed selective to the surrounding elastomer material, and the method would remain within the scope of the present invention. For example, gold metal may be etched selective to RTV 615 elastomer utilizing the appropriate chemical mixture.

2. Layer and Channel Dimensions

Microfabricated refers to the size of features of an elastomeric structure fabricated in accordance with an embodiment of the present invention. In general, variation in at least one dimension of microfabricated structures is controlled to the micron level, with at least one dimension being microscopic (i.e. below 1000 µm). Microfabrication typically involves semiconductor or MEMS fabrication techniques such as photolithography and spincoating that are designed for to produce feature dimensions on the microscopic level, with at least some of the dimension of the microfabricated structure requiring a microscope to reasonably resolve/image the structure.

In preferred aspects, flow channels 30, 32, 60 and 62 preferably have width-to-depth ratios of about 10:1. A non-exclusive list of other ranges of width-to-depth ratios in accordance with embodiments of the present invention is 0.1:1 to 100:1, more preferably 1:1 to 50:1, more preferably 2:1 to 20:1, and most preferably 3:1 to 15:1. In an exemplary aspect, flow channels 30, 32, 60 and 62 have widths of about 1 to 1000 microns. A non-exclusive list of other ranges of widths of flow channels in accordance with embodiments of the present invention is 0.01 to 1000 microns, more preferably 0.05 to 1000 microns, more preferably 0.2 to 500 microns, more preferably 1 to 250 microns, and most preferably 10 to 200 microns. Exemplary channel widths include 0.1 µm, 1 µm, 2 µm, 5 µm, 10 µm, 20 µm, 30 µm, 40 µm, 50 µm, 60 µm, 70 µm, 80 µm, 90 µm, 100 µm, 110 µm, 120 µm, 130 µm, 140 µm, 150 µm, 160 µm, 170 µm, 180 µm, 190 µm, 200 µm, 210 µm, 220 µm, 230 µm, 240 µm, and 250 µm.

Flow channels 30, 32, 60, and 62 have depths of about 1 to 100 microns. A non-exclusive list of other ranges of depths of flow channels in accordance with embodiments of the present invention is 0.01 to 1000 microns, more preferably 0.05 to 500 microns, more preferably 0.2 to 250 microns, and more preferably 1 to 100 microns, more preferably 2 to 20 microns, and most preferably 5 to 10 microns. Exemplary channel depths include including 0.01 µm, 0.02 µm, 0.05 µm, 0.1 µm, 0.2 µm, 0.5 µm, 1 µm, 2 µm, 3 µm, 4 µm, 5 µm, 7.5 µm, 10 µm, 12.5 µm, 15 µm, 17.5 µm, 20 µm, 22.5 µm, 25 µm, 30 µm, 40 µm, 50 µm, 75 µm, 100 µm, 150 µm, 200 µm, and 250 µm.

The flow channels are not limited to these specific dimension ranges and examples given above, and may vary in width in order to affect the magnitude of force required to deflect the membrane as discussed at length below in conjunction with FIG. 27. For example, extremely narrow flow channels having a width on the order of 0.01 µm may be useful in optical and other applications, as discussed in detail below. Elastomeric structures which include portions having channels of even greater width than described above are also contemplated by the present invention, and examples of applications of utilizing such wider flow channels include fluid reservoir and mixing channel structures.

The Elastomeric layers may be cast thick for mechanical stability. In an exemplary embodiment, elastomeric layer 22 of FIG. 1 is 50 microns to several centimeters thick, and more preferably approximately 4 mm thick. A non-exclusive list of ranges of thickness of the elastomer layer in accordance with other embodiments of the present invention is between about 0.1 micron to 10 cm, 1 micron to 5 cm, 10 microns to 2 cm, 100 microns to 10 mm.

Accordingly, membrane 25 of FIG. 7B separating flow channels 30 and 32 has a typical thickness of between about 0.01 and 1000 microns, more preferably 0.05 to 500 microns, more preferably 0.2 to 250, more preferably 1 to 100 microns, more preferably 2 to 50 microns, and most preferably 5 to 40 microns. As such, the thickness of elastomeric layer 22 is about 100 times the thickness of elastomeric layer 20. Exemplary membrane thicknesses include 0.01 µm, 0.02 µm, 0.03 µm, 0.05 µm, 0.1 µm, 0.2 µm, 0.3 µm, 0.5 1 µm, 2 µm, 3 µm, 5 µm, 10 µm, 12.5 µm, 15 µm, 17.5 µm, 20 µm, 22.5 µm, 25 µm, 30 µm, 40 µm, 50 µm, 75 µm, 100 µm, 150 µm, 200 µm, 250 µm, 300 µm, 400 µm, 500 µm, 750 µm, and 1000 µm.

3. Soft Lithographic Bonding

Preferably, elastomeric layers are bonded together chemically, using chemistry that is intrinsic to the polymers comprising the patterned elastomer layers. Most preferably, the bonding comprises two component "addition cure" bonding.

In a preferred aspect, the various layers of elastomer are bound together in a heterogenous bonding in which the layers have a different chemistry. Alternatively, a homogenous bonding may be used in which all layers would be of the same chemistry. Thirdly, the respective elastomer layers may optionally be glued together by an adhesive instead. In a fourth aspect, the elastomeric layers may be thermoset elastomers bonded together by heating.

In one aspect of homogeneous bonding, the elastomeric layers are composed of the same elastomer material, with the same chemical entity in one layer reacting with the same chemical entity in the other layer to bond the layers together. In one embodiment, bonding between polymer chains of like elastomer layers may result from activation of a crosslinking agent due to light, heat, or chemical reaction with a separate chemical species.

Alternatively in a heterogeneous aspect, the elastomeric layers are composed of different elastomeric materials, with a first chemical entity in one layer reacting with a second chemical entity in another layer. In one exemplary heterogenous aspect, the bonding process used to bind respective elastomeric layers together may comprise bonding together two layers of RTV 615 silicone. RTV 615 silicone is a two-part addition-cure silicone rubber. Part A contains vinyl groups and catalyst; part B contains silicon hydride (Si—H) groups. The conventional ratio for RTV 615 is 10A:1B. For bonding, one layer may be made with 30A:1B (i.e. excess vinyl groups) and the other with 3A:1B (i.e. excess Si—H groups). Each layer is cured separately. When the two layers are brought into contact and heated at elevated temperature, they bond irreversibly forming a monolithic elastomeric substrate.

In an exemplary aspect of the present invention, elastomeric structures are formed utilizing Sylgard 182, 184 or 186, or aliphatic urethane diacrylates such as (but not limited to) Ebecryl 270 or Irr 245 from UCB Chemical.

In one embodiment in accordance with the present invention, two-layer elastomeric structures were fabricated from pure acrylated Urethane Ebe 270. A thin bottom layer was spin coated at 8000 rpm for 15 seconds at 170° C. The top and bottom layers were initially cured under ultraviolet light for 10 minutes under nitrogen utilizing a Model ELC 500 device manufactured by Electrolite corporation. The assembled layers were then cured for an additional 30 minutes. Reaction was catalyzed by a 0.5% vol/vol mixture of Irgacure 500 manufactured by Ciba-Geigy Chemicals. The resulting elastomeric material exhibited moderate elasticity and adhesion to glass.

In another embodiment in accordance with the present invention, two-layer elastomeric structures were fabricated from a combination of 25% Ebe 270/50% Irr245/25% isopropyl alcohol for a thin bottom layer, and pure acrylated Urethane Ebe 270 as a top layer. The thin bottom layer was initially cured for 5 min, and the top layer initially cured for 10 minutes, under ultraviolet light under nitrogen utilizing a Model ELC 500 device manufactured by Electrolite corporation. The assembled layers were then cured for an additional 30 minutes. Reaction was catalyzed by a 0.5% vol/vol mixture of Irgacure 500 manufactured by Ciba-Geigy Chemicals. The resulting elastomeric material exhibited moderate elasticity and adhered to glass.

Alternatively, other bonding methods may be used, including activating the elastomer surface, for example by plasma exposure, so that the elastomer layers/substrate will bond when placed in contact. For example, one possible approach to bonding together elastomer layers composed of the same material is set forth by Duffy et al, "Rapid Prototyping of Microfluidic Systems in Poly (dimethylsiloxane)", *Analytical Chemistry* (1998), 70, 4974-4984, incorporated herein by reference. This paper discusses that exposing polydimethylsiloxane (PDMS) layers to oxygen plasma causes oxidation of the surface, with irreversible bonding occurring when the two oxidized layers are placed into contact.

Yet another approach to bonding together successive layers of elastomer is to utilize the adhesive properties of uncured elastomer. Specifically, a thin layer of uncured elastomer such as RTV 615 is applied on top of a first cured elastomeric layer. Next, a second cured elastomeric layer is placed on top of the uncured elastomeric layer. The thin middle layer of uncured elastomer is then cured to produce a monolithic elastomeric structure. Alternatively, uncured elastomer can be applied to the bottom of a first cured elastomer layer, with the first cured elastomer layer placed on top of a second cured elastomer layer. Curing the middle thin elastomer layer again results in formation of a monolithic elastomeric structure.

Where encapsulation of sacrificial layers is employed to fabricate the elastomer structure, bonding of successive elastomeric layers may be accomplished by pouring uncured elastomer over a previously cured elastomeric layer and any sacrificial material patterned thereupon. Bonding between elastomer layers occurs due to interpenetration and reaction of the polymer chains of an uncured elastomer layer with the polymer chains of a cured elastomer layer. Subsequent curing of the elastomeric layer will create a bond between the elastomeric layers and create a monolithic elastomeric structure.

Referring to the first method of FIGS. 1 to 7B, first elastomeric layer 20 may be created by spin-coating an RTV mixture on microfabricated mold 12 at 2000 rpm's for 30 seconds yielding a thickness of approximately 40 microns. Second elastomeric layer 22 may be created by spin-coating an RTV mixture on microfabricated mold 11. Both layers 20 and 22 may be separately baked or cured at about 80° C. for 1.5 hours. The second elastomeric layer 22 may be bonded onto first elastomeric layer 20 at about 80° C. for about 1.5 hours.

Micromachined molds 10 and 12 may be patterned photoresist on silicon wafers. In an exemplary aspect, a Shipley SJR 5740 photoresist was spun at 2000 rpm patterned with a high resolution transparency film as a mask and then developed yielding an inverse channel of approximately 10 microns in height. When baked at approximately 200° C. for about 30 minutes, the photoresist reflows and the inverse channels become rounded. In preferred aspects, the molds may be treated with trimethylchlorosilane (TMCS) vapor for about a minute before each use in order to prevent adhesion of silicone rubber.

4. Suitable Elastomeric Materials

Allcock et al, Contemporary *Polymer Chemistry*, $2^{nd}$ Ed. describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials may be characterized by a Young's modulus. Elastomeric materials having a Young's modulus of between about 1 Pa-1 TPa, more preferably between about 10 Pa-100 GPa, more preferably between about 20 Pa-1 GPa, more preferably between about 50 Pa-10 MPa, and more preferably between about 100 Pa-1 MPa are useful in accordance with the present invention, although elastomeric materials having a Young's modulus outside of these ranges could also be utilized depending upon the needs of a particular application.

The systems of the present invention may be fabricated from a wide variety of elastomers. In an exemplary aspect, the elastomeric layers may preferably be fabricated from silicone rubber. However, other suitable elastomers may also be used.

In an exemplary aspect of the present invention, the present systems are fabricated from an elastomeric polymer such as GE RTV 615 (formulation), a vinyl-silane cross-linked (type) silicone elastomer (family). However, the present systems are not limited to this one formulation, type or even this family of polymer; rather, nearly any elastomeric polymer is suitable. An important requirement for the preferred method of fabrication of the present microvalves is the ability to bond multiple layers of elastomers together. In the case of multilayer soft lithography, layers of elastomer are cured separately and then bonded together. This scheme requires that cured layers possess sufficient reactivity to bond together. Either the layers may be of the same type, and are capable of bonding to themselves, or they may be of two different types, and are capable of bonding to each other. Other possibilities include the use an adhesive between layers and the use of thermoset elastomers.

Given the tremendous diversity of polymer chemistries, precursors, synthetic methods, reaction conditions, and potential additives, there are a huge number of possible elastomer systems that could be used to make monolithic elastomeric microvalves and pumps. Variations in the materials used will most likely be driven by the need for particular material properties, i.e. solvent resistance, stiffness, gas permeability, or temperature stability.

There are many, many types of elastomeric polymers. A brief description of the most common classes of elastomers is presented here, with the intent of showing that even with relatively "standard" polymers, many possibilities for bonding exist. Common elastomeric polymers include polyisoprene, polybutadiene, polychloroprene, polyisobutylene, poly(styrene-butadiene-styrene), the polyurethanes, and silicones.

Polyisoprene, Polybutadiene, Polychloroprene:

Polyisoprene, polybutadiene, and polychloroprene are all polymerized from diene monomers, and therefore have one double bond per monomer when polymerized. This double bond allows the polymers to be converted to elastomers by vulcanization (essentially, sulfur is used to form crosslinks between the double bonds by heating). This would easily allow homogeneous multilayer soft lithography by incomplete vulcanization of the layers to be bonded; photoresist encapsulation would be possible by a similar mechanism.

Polyisobutylene:

Pure Polyisobutylene has no double bonds, but is cross-linked to use as an elastomer by including a small amount (~1%) of isoprene in the polymerization. The isoprene monomers give pendant double bonds on the Polyisobutylene backbone, which may then be vulcanized as above.

Poly(Styrene-Butadiene-Styrene):

Poly(styrene-butadiene-styrene) is produced by living anionic polymerization (that is, there is no natural chain-terminating step in the reaction), so "live" polymer ends can exist in the cured polymer. This makes it a natural candidate for the present photoresist encapsulation system (where there will be plenty of unreacted monomer in the liquid layer poured on top of the cured layer). Incomplete curing would allow homogeneous multilayer soft lithography (A to A bonding). The chemistry also facilitates making one layer with extra butadiene ("A") and coupling agent and the other layer ("B") with a butadiene deficit (for heterogeneous multilayer soft lithography). SBS is a "thermoset elastomer", meaning that above a certain temperature it melts and becomes plastic (as opposed to elastic); reducing the temperature yields the elastomer again. Thus, layers can be bonded together by heating.

Polyurethanes:

Polyurethanes are produced from di-isocyanates (A-A) and di-alcohols or di-amines (B-B); since there are a large variety of di-isocyanates and di-alcohols/amines, the number of different types of polyurethanes is huge. The A vs. B nature of the polymers, however, would make them useful for heterogeneous multilayer soft lithography just as RTV 615 is: by using excess A-A in one layer and excess B-B in the other layer.

Silicones:

Silicone polymers probably have the greatest structural variety, and almost certainly have the greatest number of commercially available formulations. The vinyl-to-(Si—H) crosslinking of RTV 615 (which allows both heterogeneous multilayer soft lithography and photoresist encapsulation) has already been discussed, but this is only one of several crosslinking methods used in silicone polymer chemistry.

5. Operation of Device

FIGS. 7B and 7H together show the closing of a first flow channel by pressurizing a second flow channel, with FIG. 7B (a front sectional view cutting through flow channel 32 in corresponding FIG. 7A), showing an open first flow channel 30; with FIG. 7H showing first flow channel 30 closed by pressurization of the second flow channel 32.

Referring to FIG. 7B, first flow channel 30 and second flow channel 32 are shown. Membrane 25 separates the flow channels, forming the top of first flow channel 30 and the bottom of second flow channel 32. As can be seen, flow channel 30 is "open".

As can be seen in FIG. 7H, pressurization of flow channel 32 (either by gas or liquid introduced therein) causes membrane 25 to deflect downward, thereby pinching off flow F passing through flow channel 30. Accordingly, by varying the pressure in channel 32, a linearly actuable valving system is provided such that flow channel 30 can be opened or closed by moving membrane 25 as desired. (For illustration purposes only, channel 30 in FIG. 7G is shown in a "mostly closed" position, rather than a "fully closed" position).

Since such valves are actuated by moving the roof of the channels themselves (i.e.: moving membrane 25) valves and pumps produced by this technique have a truly zero dead volume, and switching valves made by this technique have a dead volume approximately equal to the active volume of the valve, for example about 100×100×10 µm=100 pL. Such dead volumes and areas consumed by the moving membrane are approximately two orders of magnitude smaller than known conventional microvalves. Smaller and larger valves and switching valves are contemplated in the present invention, and a non-exclusive list of ranges of dead volume includes 1 aL to 1 uL, 100 aL to 100 nL, 1 fL to 10 nL, 100 fL to 1 nL, and 1 pL to 100 pL.

The extremely small volumes capable of being delivered by pumps and valves in accordance with the present invention represent a substantial advantage. Specifically, the smallest known volumes of fluid capable of being manually metered is around 0.1 µl. The smallest known volumes capable of being metered by automated systems is about ten-times larger (1 µl). Utilizing pumps and valves in accordance with the present invention, volumes of liquid of 10 nl or smaller can routinely be metered and dispensed. The accurate metering of extremely small volumes of fluid enabled by the present invention would be extremely valuable in a large number of biological applications, including diagnostic tests and assays.

Equation 1 represents a highly simplified mathematical model of deflection of a rectangular, linear, elastic, isotropic plate of uniform thickness by an applied pressure:

$$w=(BPb^4)/(Eh^3), \qquad (1)$$

where:
  w=deflection of plate;
  B=shape coefficient (dependent upon length vs. width and support of edges of plate);
  P=applied pressure;
  b=plate width
  E=Young's modulus; and
  h=plate thickness.

Thus even in this extremely simplified expression, deflection of an elastomeric membrane in response to a pressure will be a function of: the length, width, and thickness of the membrane, the flexibility of the membrane (Young's modulus), and the applied actuation force. Because each of these parameters will vary widely depending upon the actual dimensions and physical composition of a particular elastomeric device in accordance with the present invention, a wide range of membrane thicknesses and elasticity's, channel widths, and actuation forces are contemplated by the present invention.

It should be understood that the formula just presented is only an approximation, since in general the membrane does not have uniform thickness, the membrane thickness is not necessarily small compared to the length and width, and the deflection is not necessarily small compared to length, width, or thickness of the membrane. Nevertheless, the equation serves as a useful guide for adjusting variable parameters to achieve a desired response of deflection versus applied force.

Figure 8A:
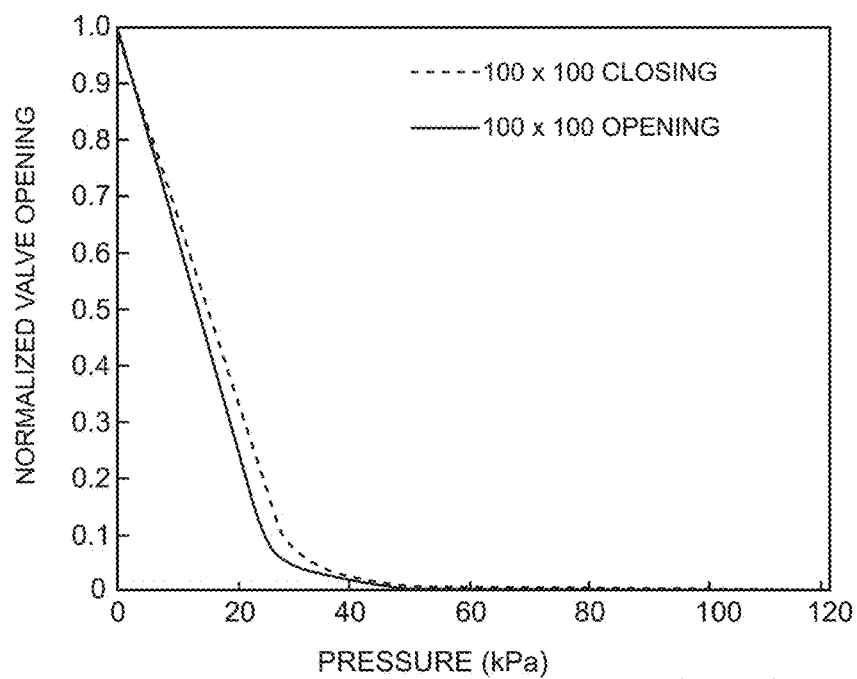
FIGS. 8A and 8B illustrates valve opening vs. applied pressure for various flow channels.
Figure 8B:
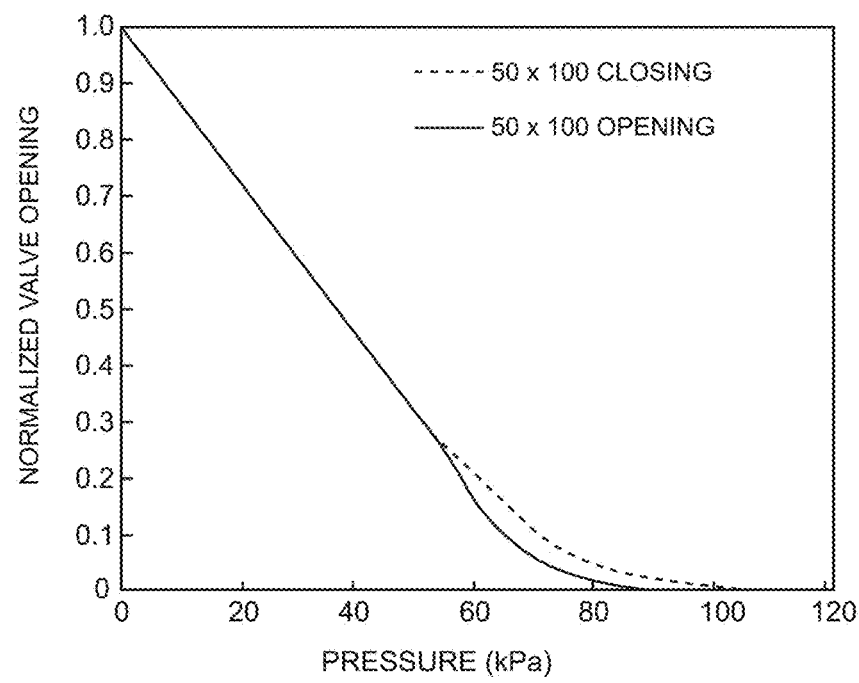

FIGS. 8A and 8B illustrate valve opening vs. applied pressure for a 100 µm wide first flow channel 30 and a 50 µm wide second flow channel 32. The membrane of this device was formed by a layer of General Electric Silicones RTV 615 having a thickness of approximately 30 µm and a Young's modulus of approximately 750 kPa. FIGS. 21a and 21b show the extent of opening of the valve to be substantially linear over most of the range of applied pressures.

Air pressure was applied to actuate the membrane of the device through a 10 cm long piece of plastic tubing having an outer diameter of 0.025" connected to a 25 mm piece of stainless steel hypodermic tubing with an outer diameter of 0.025" and an inner diameter of 0.013". This tubing was placed into contact with the control channel by insertion into the elastomeric block in a direction normal to the control channel. Air pressure was applied to the hypodermic tubing from an external LHDA miniature solenoid valve manufactured by Lee Co.

While control of the flow of material through the device has so far been described utilizing applied gas pressure, other fluids could be used.

For example, air is compressible, and thus experiences some finite delay between the time of application of pressure by the external solenoid valve and the time that this pressure is experienced by the membrane. In an alternative embodiment of the present invention, pressure could be applied from an external source to a noncompressible fluid such as water or hydraulic oils, resulting in a near-instantaneous transfer of applied pressure to the membrane. However, if the displaced volume of the valve is large or the control channel is narrow, higher viscosity of a control fluid may contribute to delay in actuation. The optimal medium for transferring pressure will therefore depend upon the particular application and device configuration, and both gaseous and liquid media are contemplated by the invention.

While external applied pressure as described above has been applied by a pump/tank system through a pressure regulator and external miniature valve, other methods of applying external pressure are also contemplated in the present invention, including gas tanks, compressors, piston systems, and columns of liquid. Also contemplated is the use of naturally occurring pressure sources such as may be found inside living organisms, such as blood pressure, gastric pressure, the pressure present in the cerebrospinal fluid, pressure present in the intra-ocular space, and the pressure exerted by muscles during normal flexure. Other methods of regulating external pressure are also contemplated, such as miniature valves, pumps, macroscopic peristaltic pumps, pinch valves, and other types of fluid regulating equipment such as is known in the art.

As can be seen, the response of valves in accordance with embodiments of the present invention have been experimentally shown to be almost perfectly linear over a large portion of its range of travel, with minimal hysteresis. Accordingly, the present valves are ideally suited for microfluidic metering and fluid control. The linearity of the valve response demonstrates that the individual valves are well modeled as Hooke's Law springs. Furthermore, high pressures in the flow channel (i.e.: back pressure) can be countered simply by increasing the actuation pressure. Experimentally, the present inventors have achieved valve closure at back pressures of 70 kPa, but higher pressures are also contemplated. The following is a nonexclusive list of pressure ranges encompassed by the present invention: 10 Pa-25 MPa; 100 Pa-10 Mpa, 1 kPa-1 MPa, 1 kPa-300 kPa, 5 kPa-200 kPa, and 15 kPa-100 kPa.

While valves and pumps do not require linear actuation to open and close, linear response does allow valves to more easily be used as metering devices. In one embodiment of the invention, the opening of the valve is used to control flow rate by being partially actuated to a known degree of closure. Linear valve actuation makes it easier to determine the amount of actuation force required to close the valve to a desired degree of closure. Another benefit of linear actuation is that the force required for valve actuation may be easily determined from the pressure in the flow channel. If actuation is linear, increased pressure in the flow channel may be countered by adding the same pressure (force per unit area) to the actuated portion of the valve.

Linearity of a valve depends on the structure, composition, and method of actuation of the valve structure. Furthermore, whether linearity is a desirable characteristic in a valve depends on the application. Therefore, both linearly and non-linearly actuable valves are contemplated in the present invention, and the pressure ranges over which a valve is linearly actuable will vary with the specific embodiment.

Figure 9:
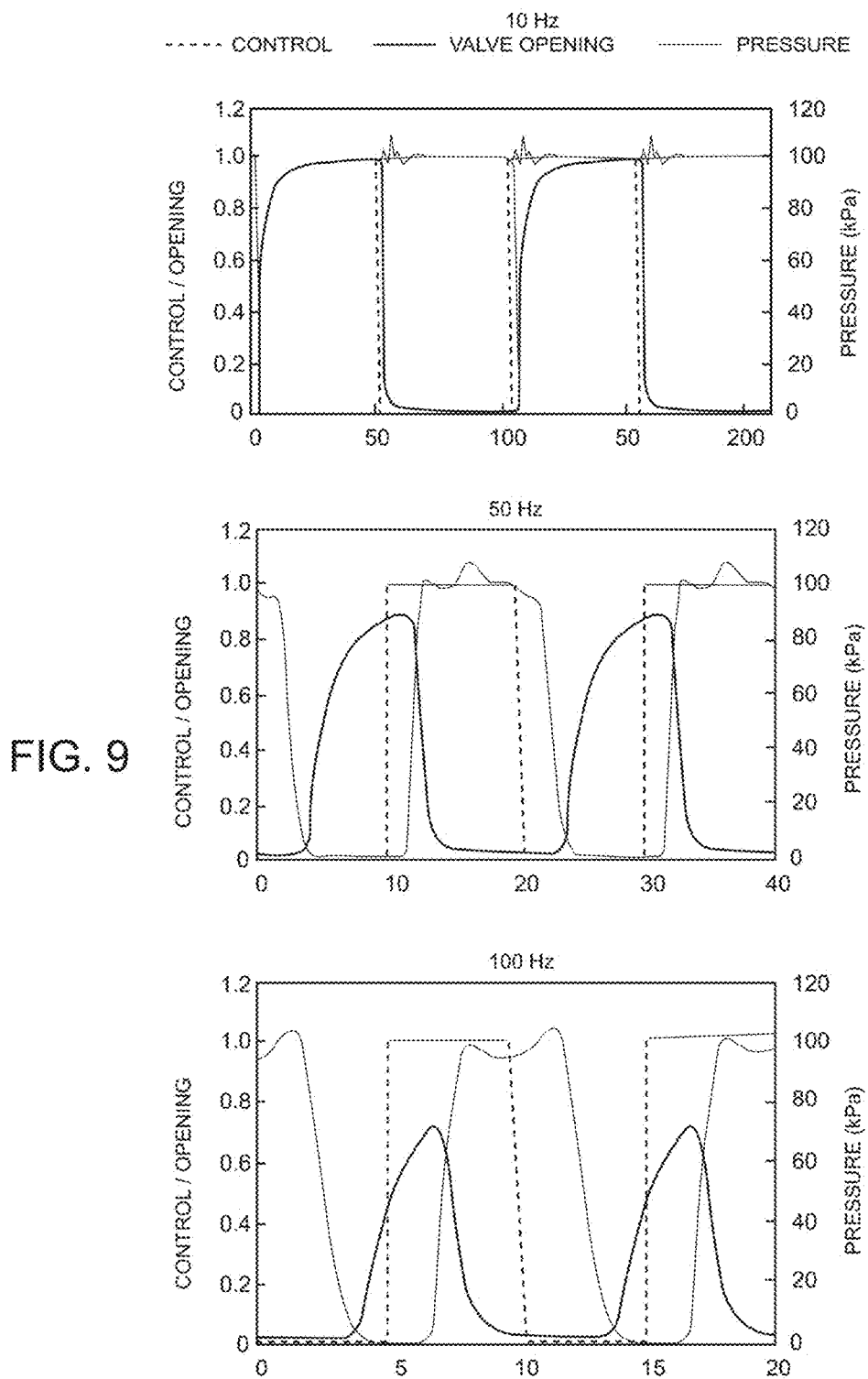
FIG. 9 illustrates time response of a 100 μm×100 μm×10 μm RTV microvalve.

FIG. 9 illustrates time response (i.e.: closure of valve as a function of time in response to a change in applied pressure) of a 100 μm×100 μm×10 μm RTV microvalve with 10-cm-long air tubing connected from the chip to a pneumatic valve as described above.

Two periods of digital control signal, actual air pressure at the end of the tubing and valve opening are shown in FIG. 9. The pressure applied on the control line is 100 kPa, which is substantially higher than the ~40 kPa required to close the valve. Thus, when closing, the valve is pushed closed with a pressure 60 kPa greater than required. When opening, however, the valve is driven back to its rest position only by its own spring force (≤40 kPa). Thus, τclose is expected to be smaller than τopen. There is also a lag between the control signal and control pressure response, due to the limitations of the miniature valve used to control the pressure. Calling such lags t and the 1/e time constants τ, the values are: topen=3.63 ms, τopen=1.88 ms, tclose=2.15 ms, τclose=0.51 ms. If 3τ each are allowed for opening and closing, the valve runs comfortably at 75 Hz when filled with aqueous solution.

If one used another actuation method which did not suffer from opening and closing lag, this valve would run at ~375 Hz. Note also that the spring constant can be adjusted by changing the membrane thickness; this allows optimization for either fast opening or fast closing. The spring constant could also be adjusted by changing the elasticity (Young's modulus) of the membrane, as is possible by introducing dopant into the membrane or by utilizing a different elastomeric material to serve as the membrane (described above in conjunction with FIGS. 7C-7H.)

When experimentally measuring the valve properties as illustrated in FIG. 9 the valve opening was measured by fluorescence. In these experiments, the flow channel was filled with a solution of fluorescein isothiocyanate (FITC) in buffer (pH≥8) and the fluorescence of a square area occupying the center ~⅓rd of the channel is monitored on an epi-fluorescence microscope with a photomultiplier tube with a 10 kHz bandwidth. The pressure was monitored with a Wheatstone-bridge pressure sensor (SenSym SCC15GD2) pressurized simultaneously with the control line through nearly identical pneumatic connections.

6. Flow Channel Cross Sections

The flow channels of the present invention may optionally be designed with different cross sectional sizes and shapes, offering different advantages, depending upon their desired application. For example, the cross sectional shape of the lower flow channel may have a curved upper surface, either along its entire length or in the region disposed under an upper cross channel). Such a curved upper surface facilitates valve sealing, as follows.

Figure 10:
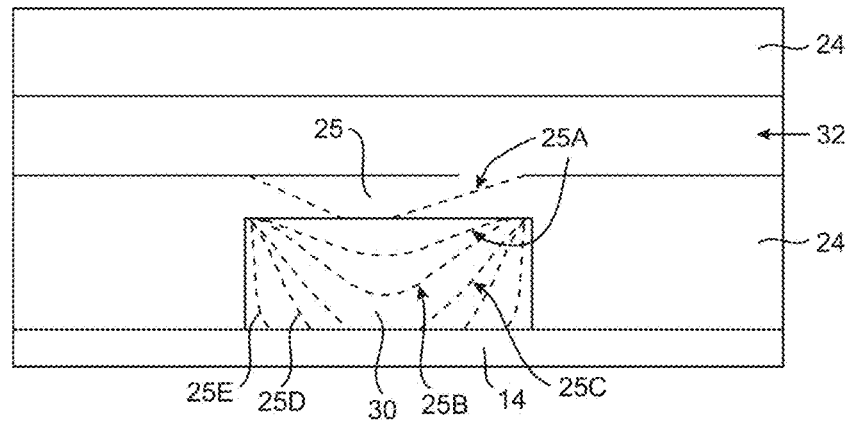
FIG. 10 is a front sectional view of the valve of FIG. 7B showing actuation of the membrane.

Referring to FIG. 10, a cross sectional view (similar to that of FIG. 7B) through flow channels 30 and 32 is shown. As can be seen, flow channel 30 is rectangular in cross sectional shape. In an alternate preferred aspect of the invention, as shown in FIG. 10, the cross-section of a flow channel 30 instead has an upper curved surface.

Referring first to FIG. 10, when flow channel 32 is pressurized, the membrane portion 25 of elastomeric block 24 separating flow channels 30 and 32 will move downwardly to the successive positions shown by the dotted lines 25A, 25B, 25C, 25D, and 25E. As can be seen, incomplete sealing may possibly result at the edges of flow channel 30 adjacent planar substrate 14.

Figure 11:
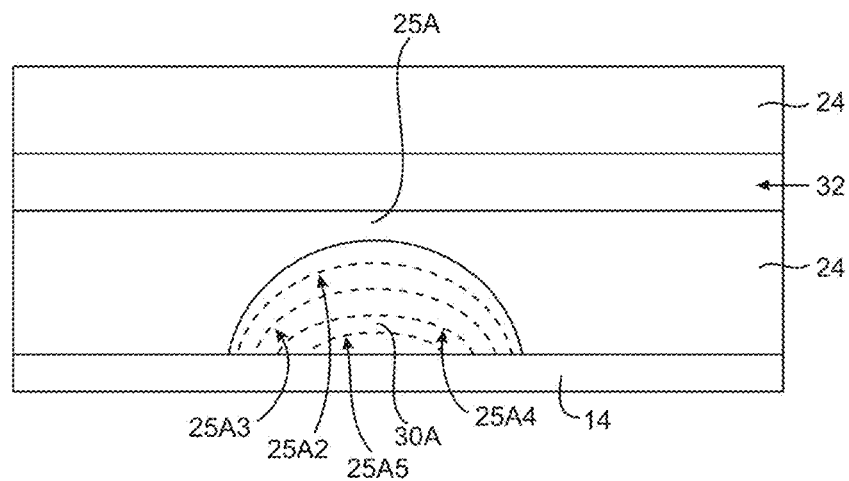
FIG. 11 is a front sectional view of an alternative embodiment of a valve having a flow channel with a curved upper surface.

In the alternate preferred embodiment of FIG. 11, flow channel 30a has a curved upper wall 25A. When flow channel 32 is pressurized, membrane portion 25 will move downwardly to the successive positions shown by dotted lines 25A2, 25A3, 25A4 and 25A5, with edge portions of the membrane moving first into the flow channel, followed by top membrane portions. An advantage of having such a curved upper surface at membrane 25A is that a more complete seal will be provided when flow channel 32 is pressurized. Specifically, the upper wall of the flow channel 30 will provide a continuous contacting edge against planar substrate 14, thereby avoiding the "island" of contact seen between wall 25 and the bottom of flow channel 30 in FIG. 10.

Another advantage of having a curved upper flow channel surface at membrane 25A is that the membrane can more readily conform to the shape and volume of the flow channel in response to actuation. Specifically, where a rectangular flow channel is employed, the entire perimeter (2× flow channel height, plus the flow channel width) must be forced into the flow channel. However where an arched flow channel is used, a smaller perimeter of material (only the semi-circular arched portion) must be forced into the channel. In this manner, the membrane requires less change in perimeter for actuation and is therefore more responsive to an applied actuation force to block the flow channel In an alternate aspect, (not illustrated), the bottom of flow channel 30 is rounded such that its curved surface mates with the curved upper wall 25A as seen in FIG. 20 described above.

In summary, the actual conformational change experienced by the membrane upon actuation will depend upon the configuration of the particular elastomeric structure. Specifically, the conformational change will depend upon the length, width, and thickness profile of the membrane, its attachment to the remainder of the structure, and the height, width, and shape of the flow and control channels and the material properties of the elastomer used. The conformational change may also depend upon the method of actuation, as actuation of the membrane in response to an applied pressure will vary somewhat from actuation in response to a magnetic or electrostatic force.

Moreover, the desired conformational change in the membrane will also vary depending upon the particular application for the elastomeric structure. In the simplest embodiments described above, the valve may either be open or closed, with metering to control the degree of closure of the valve. In other embodiments however, it may be desirable to alter the shape of the membrane and/or the flow channel in order to achieve more complex flow regulation. For instance, the flow channel could be provided with raised protrusions beneath the membrane portion, such that upon actuation the membrane shuts off only a percentage of the flow through the flow channel, with the percentage of flow blocked insensitive to the applied actuation force.

Many membrane thickness profiles and flow channel cross-sections are contemplated by the present invention, including rectangular, trapezoidal, circular, ellipsoidal, parabolic, hyperbolic, and polygonal, as well as sections of the above shapes. More complex cross-sectional shapes, such as the embodiment with protrusions discussed immediately above or an embodiment having concavities in the flow channel, are also contemplated by the present invention.

In addition, while the invention is described primarily above in conjunction with an embodiment wherein the walls and ceiling of the flow channel are formed from elastomer, and the floor of the channel is formed from an underlying substrate, the present invention is not limited to this particular orientation. Walls and floors of channels could also be formed in the underlying substrate, with only the ceiling of the flow channel constructed from elastomer. This elastomer flow channel ceiling would project downward into the channel in response to an applied actuation force, thereby controlling the flow of material through the flow channel. In general, monolithic elastomer structures as described elsewhere in the instant application are preferred for microfluidic applications. However, it may be useful to employ channels formed in the substrate where such an arrangement provides advantages. For instance, a substrate including optical waveguides could be constructed so that the optical waveguides direct light specifically to the side of a microfluidic channel.

7. Networked Systems

Figure 12A:
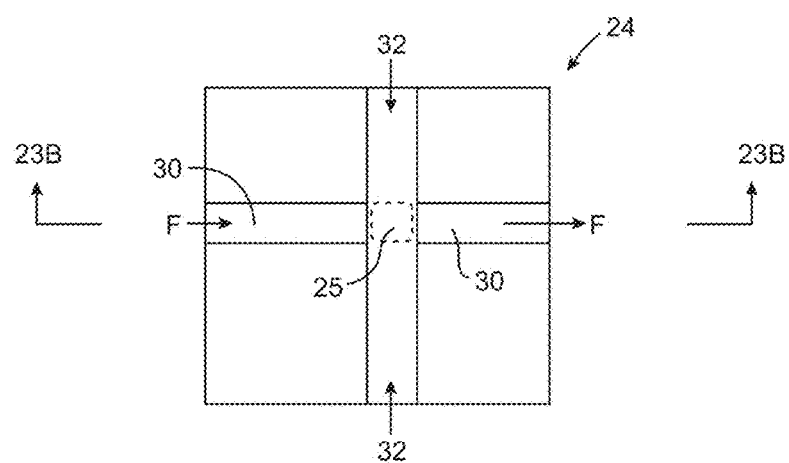
FIG. 12A is a top schematic view of an on/off valve.
Figure 13A:
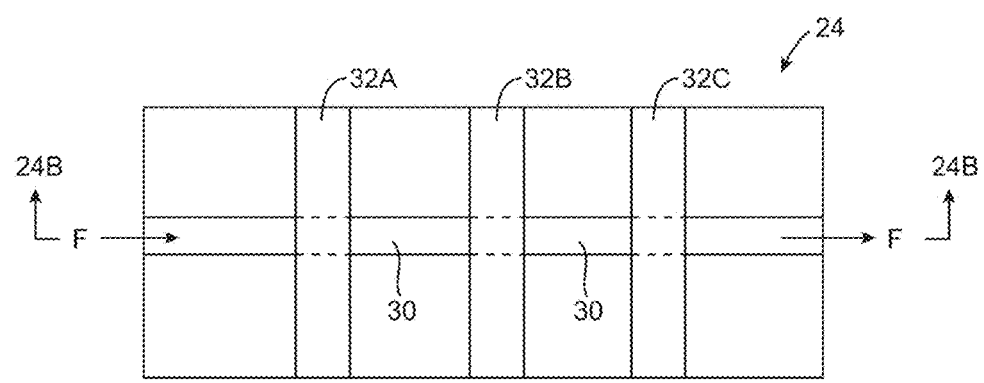
FIG. 13A is a top schematic view of a peristaltic pumping system.
Figure 12B:
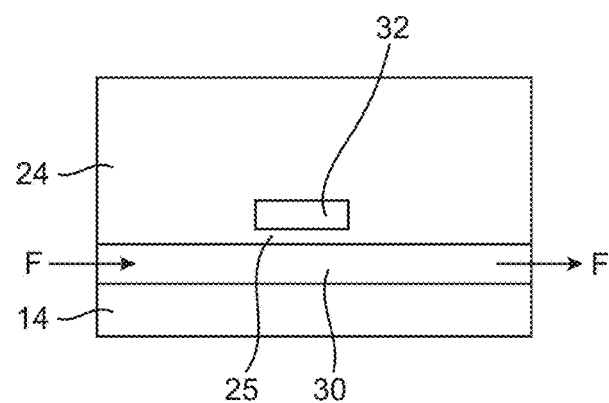
FIG. 12B is a sectional elevation view along line 23B-23B in FIG. 12A
Figure 13B:
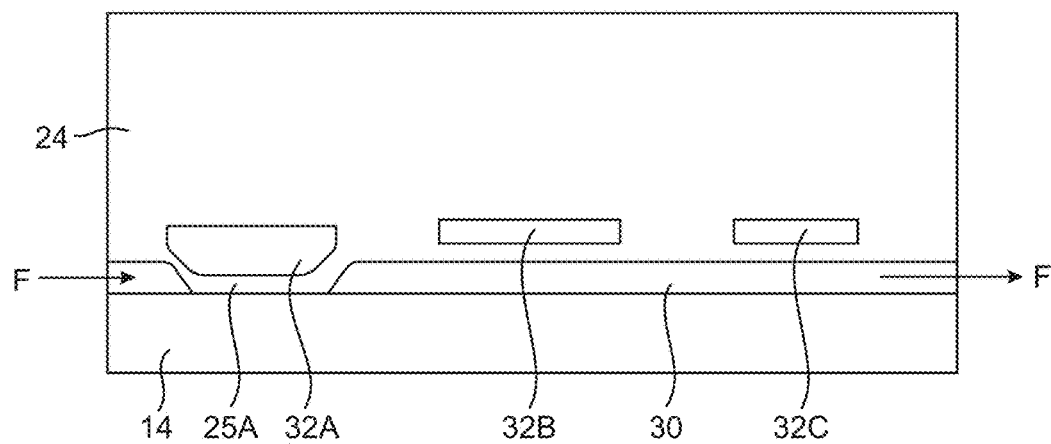
FIG. 13B is a sectional elevation view along line 24B-24B in FIG. 13A
Figure 14:
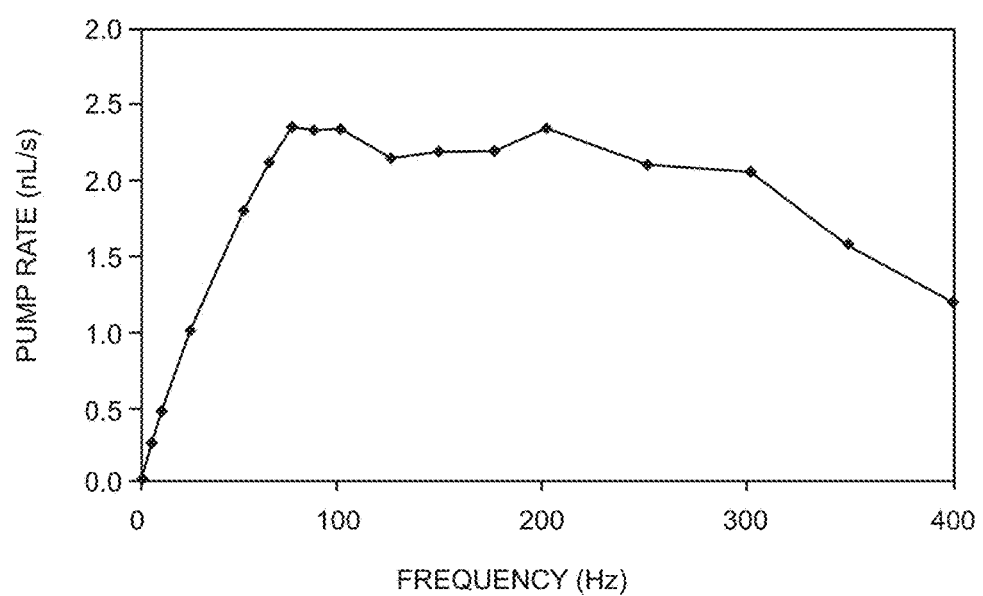
FIG. 14 is a graph showing experimentally achieved pumping rates vs. frequency for an embodiment of the peristaltic pumping system of FIG. 13.
Figure 15A:
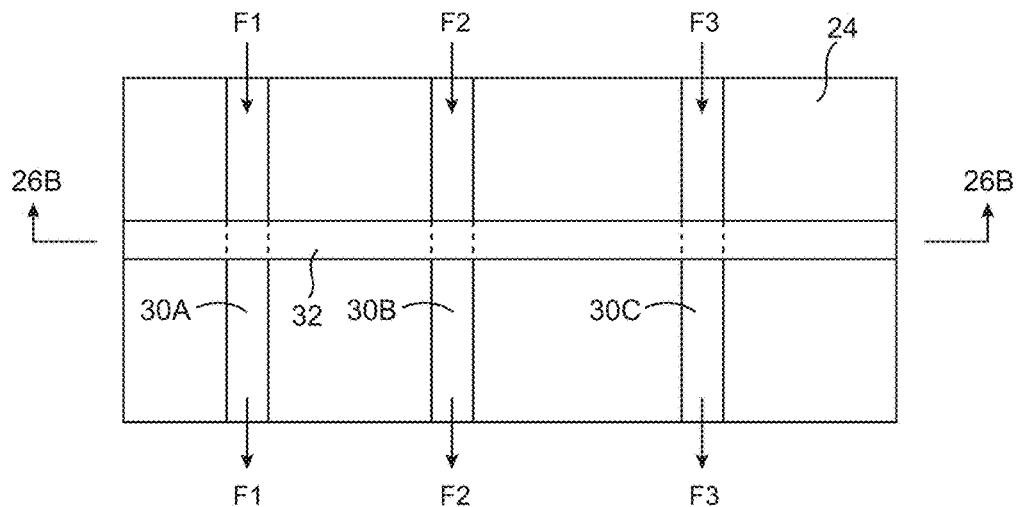
FIG. 15A is a top schematic view of one control line actuating multiple flow lines simultaneously.
Figure 15B:
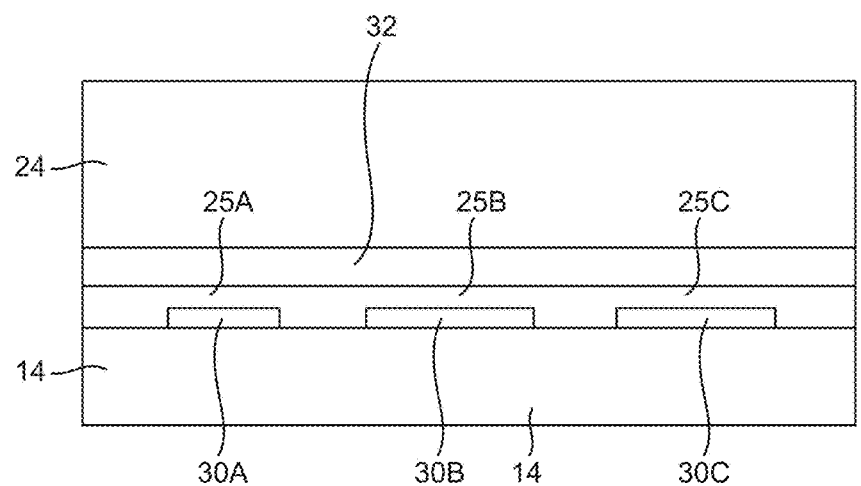
FIG. 15B is a sectional elevation view along line 26B-26B in FIG. 15A
Figure 16:
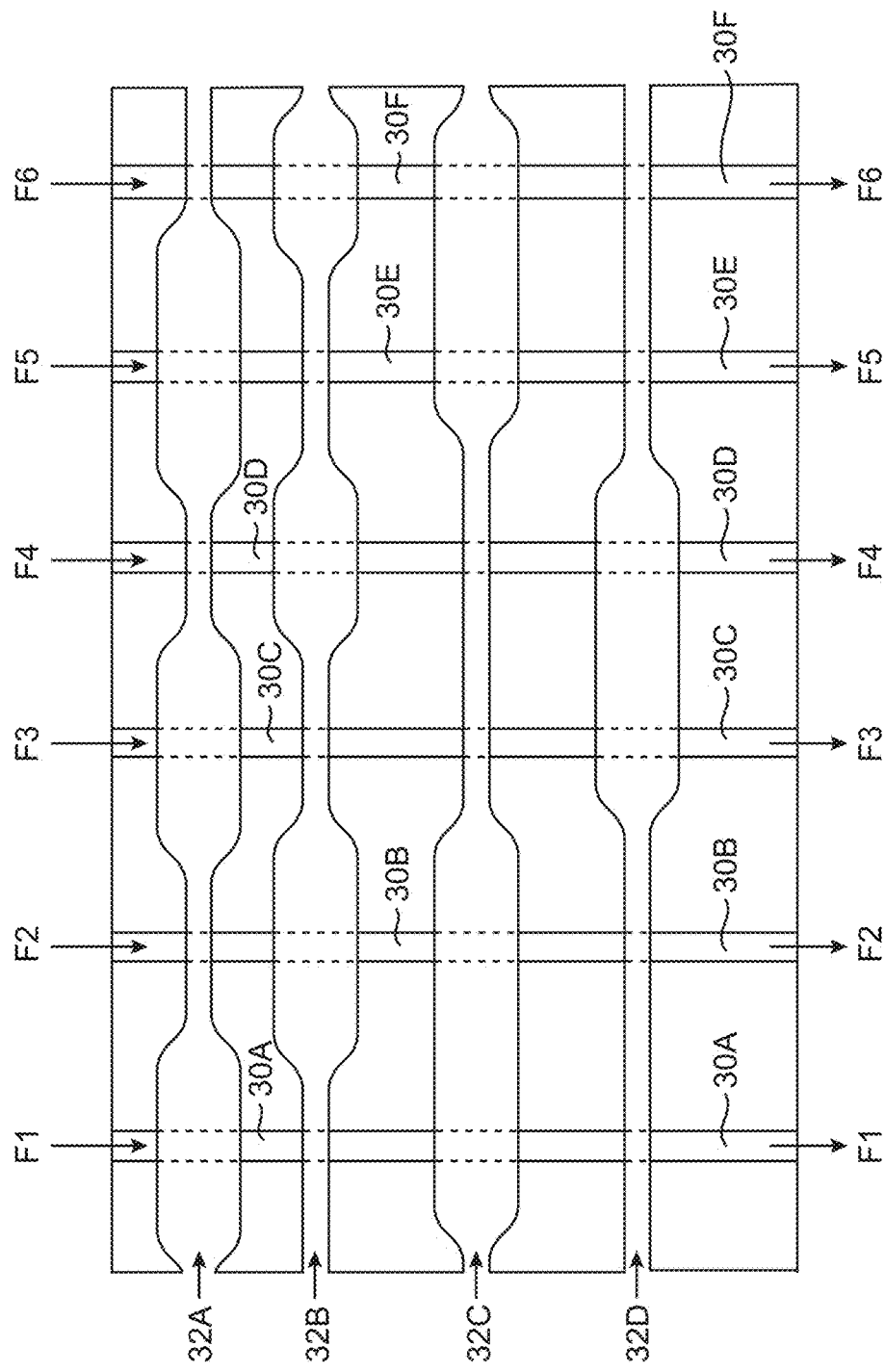
FIG. 16 is a schematic illustration of a multiplexed system adapted to permit flow through various channels.

FIGS. 12A and 12B show a views of a single on/off valve, identical to the systems set forth above, (for example in FIG. 7A). FIGS. 13A and 13B shows a peristaltic pumping system comprised of a plurality of the single addressable on/off valves as seen in FIG. 12, but networked together. FIG. 14 is a graph showing experimentally achieved pumping rates vs. frequency for the peristaltic pumping system of FIG. 13. FIGS. 15A and 15B show a schematic view of a plurality of flow channels which are controllable by a single control line. This system is also comprised of a plurality of the single addressable on/off valves of FIG. 12, multiplexed together, but in a different arrangement than that of FIG. 12. FIG. 16 is a schematic illustration of a multiplexing system adapted to permit fluid flow through selected channels, comprised of a plurality of the single on/off valves of FIG. 12, joined or networked together.

Referring first to FIGS. 12A and 12B, a schematic of flow channels 30 and 32 is shown. Flow channel 30 preferably has a fluid (or gas) flow F passing therethrough. Flow channel 32, (which crosses over flow channel 30, as was already explained herein), is pressurized such that membrane 25 separating the flow channels may be depressed into the path of flow channel 30, shutting off the passage of flow F therethrough, as has been explained. As such, "flow channel" 32 can also be referred to as a "control line" which actuates a single valve in flow channel 30. In FIGS. 12 to 15, a plurality of such addressable valves are joined or networked together in various arrangements to produce pumps, capable of peristaltic pumping, and other fluidic logic applications.

Referring to FIGS. 13A and 13B, a system for peristaltic pumping is provided, as follows. A flow channel 30 has a plurality of generally parallel flow channels (i.e.: control lines) 32A, 32B and 32C passing thereover. By pressurizing control line 32A, flow F through flow channel 30 is shut off under membrane 25A at the intersection of control line 32A and flow channel 30. Similarly, (but not shown), by pressurizing control line 32B, flow F through flow channel 30 is shut off under membrane 25B at the intersection of control line 32B and flow channel 30, etc.

Each of control lines 32A, 32B, and 32C is separately addressable. Therefore, peristalsis may be actuated by the pattern of actuating 32A and 32C together, followed by 32A, followed by 32A and 32B together, followed by 32B, followed by 32B and C together, etc. This corresponds to a successive "101, 100, 110, 010, 011, 001" pattern, where "0" indicates "valve open" and "1" indicates "valve closed." This peristaltic pattern is also known as a 120° pattern (referring to the phase angle of actuation between three valves). Other peristaltic patterns are equally possible, including 60° and 90° patterns.

In experiments performed by the inventors, a pumping rate of 2.35 nL/s was measured by measuring the distance traveled by a column of water in thin (0.5 mm i.d.) tubing; with 100×100×10 µm valves under an actuation pressure of 40 kPa. The pumping rate increased with actuation frequency until approximately 75 Hz, and then was nearly constant until above 200 Hz. The valves and pumps are also quite durable and the elastomer membrane, control channels, or bond have never been observed to fail. In experiments performed by the inventors, none of the valves in the peristaltic pump described herein show any sign of wear or fatigue after more than 4 million actuations. In addition to their durability, they are also gentle. A solution of E. Coli pumped through a channel and tested for viability showed a 94% survival rate.

FIG. 14 is a graph showing experimentally achieved pumping rates vs. frequency for the peristaltic pumping system of FIG. 13.

FIGS. 15A and 15B illustrates another way of assembling a plurality of the addressable valves of FIG. 12. Specifically, a plurality of parallel flow channels 30A, 30B, and 30C are provided. Flow channel (i.e.: control line) 32 passes thereover across flow channels 30A, 30B, and 30C. Pressurization of control line 32 simultaneously shuts off flows F1, F2 and F3 by depressing membranes 25A, 25B, and 25C located at the intersections of control line 32 and flow channels 30A, 30B, and 30C.

FIG. 16 is a schematic illustration of a multiplexing system adapted to selectively permit fluid to flow through selected channels, as follows. The downward deflection of membranes separating the respective flow channels from a control line passing thereabove (for example, membranes 25A, 25B, and 25C in FIGS. 15A and 15B) depends strongly upon the membrane dimensions. Accordingly, by varying the widths of flow channel control line 32 in FIGS. 15A and 15B, it is possible to have a control line pass over multiple flow channels, yet only actuate (i.e.: seal) desired flow channels. FIG. 16 illustrates a schematic of such a system, as follows.

A plurality of parallel flow channels 30A, 30B, 30C, 30D, 30E and 30F are positioned under a plurality of parallel control lines 32A, 32B, 32C, 32D, 32E and 32F. Control channels 32A, 32B, 32C, 32D, 32E and 32F are adapted to shut off fluid flows F1, F2, F3, F4, F5 and F6 passing through parallel flow channels 30A, 30B, 30C, 30D, 30E and 30F using any of the valving systems described above, with the following modification.

Each of control lines 32A, 32B, 32C, 32D, 32E and 32F have both wide and narrow portions. For example, control line 32A is wide in locations disposed over flow channels 30A, 30C and 30E. Similarly, control line 32B is wide in locations disposed over flow channels 30B, 30D and 30F, and control line 32C is wide in locations disposed over flow channels 30A, 30B, 30E and 30F.

At the locations where the respective control line is wide, its pressurization will cause the membrane (25) separating the flow channel and the control line to depress significantly into the flow channel, thereby blocking the flow passage therethrough. Conversely, in the locations where the respective control line is narrow, membrane (25) will also be narrow. Accordingly, the same degree of pressurization will not result in membrane (25) becoming depressed into the flow channel (30). Therefore, fluid passage thereunder will not be blocked.

For example, when control line 32A is pressurized, it will block flows F1, F3 and F5 in flow channels 30A, 30C and 30E. Similarly, when control line 32C is pressurized, it will block flows F1, F2, F5 and F6 in flow channels 30A, 30B, 30E and 30F. As can be appreciated, more than one control line can be actuated at the same time. For example, control lines 32A and 32C can be pressurized simultaneously to block all fluid flow except F4 (with 32A blocking F1, F3 and F5; and 32C blocking F1, F2, F5 and F6).

By selectively pressurizing different control lines (32) both together and in various sequences, a great degree of fluid flow control can be achieved. Moreover, by extending the present system to more than six parallel flow channels (30) and more than four parallel control lines (32), and by varying the positioning of the wide and narrow regions of the control lines, very complex fluid flow control systems may be fabricated. A property of such systems is that it is possible to turn on any one flow channel out of n flow channels with only 2(log 2n) control lines.

8. Switchable Flow Arrays

Figure 17A:
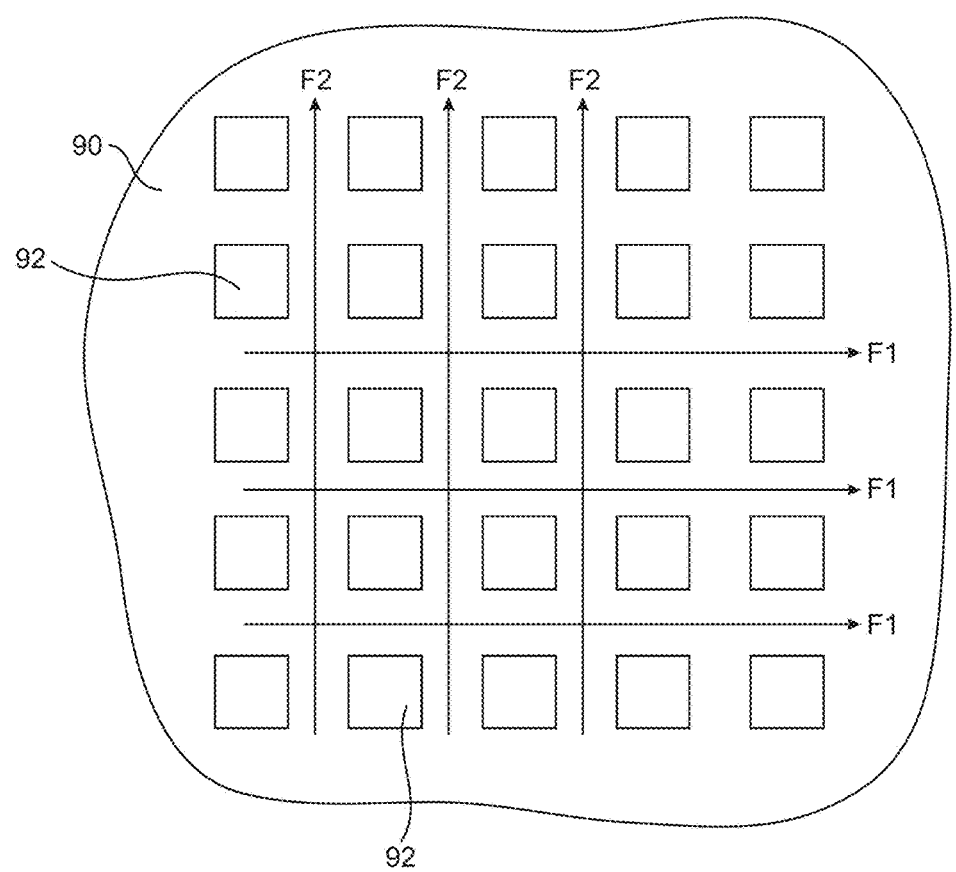
FIGS. 17A to 17D show plan views of one embodiment of a switchable flow array.

In yet another novel embodiment, fluid passage can be selectively directed to flow in either of two perpendicular directions. An example of such a "switchable flow array" system is provided in FIGS. 17A to 17D. FIG. 17A shows a bottom view of a first layer of elastomer 90, (or any other suitable substrate), having a bottom surface with a pattern of recesses forming a flow channel grid defined by an array of solid posts 92, each having flow channels passing therearound.

Figure 17B:
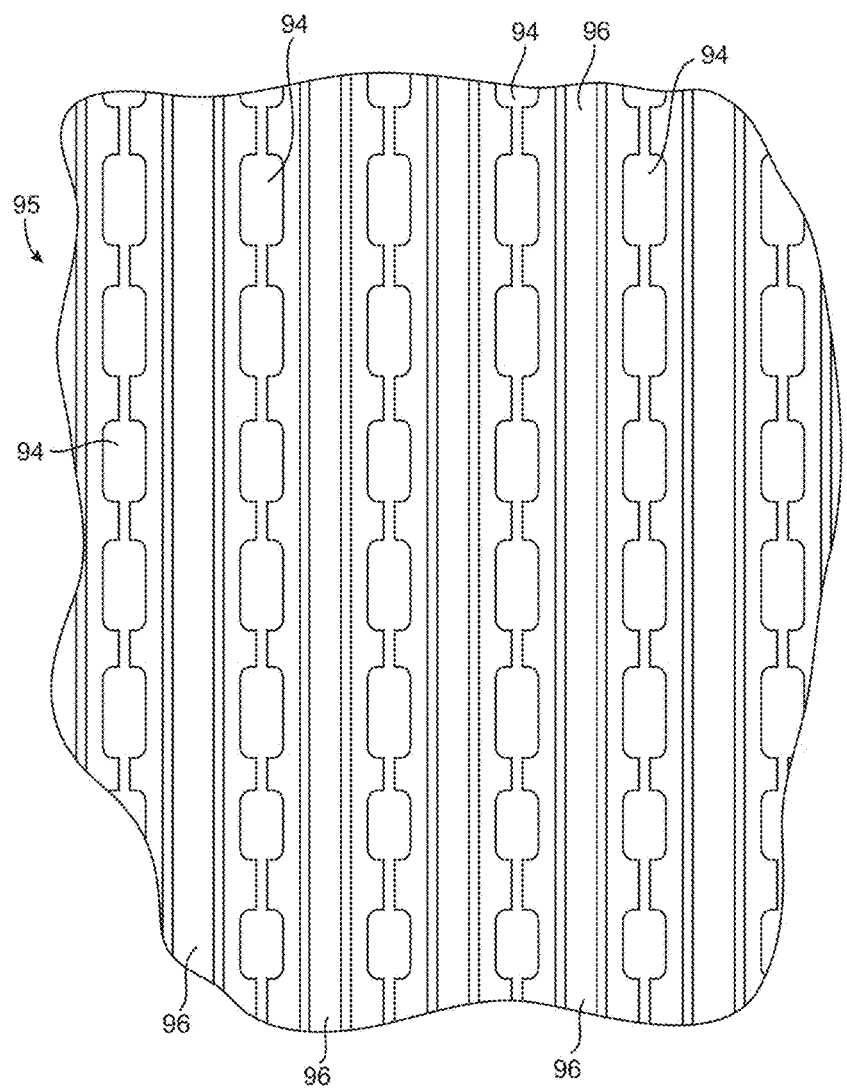

In preferred aspects, an additional layer of elastomer is bound to the top surface of layer 90 such that fluid flow can be selectively directed to move either in direction F1, or perpendicular direction F2. FIG. 17B is a bottom view of the bottom surface of the second layer of elastomer 95 showing recesses formed in the shape of alternating "vertical" control lines 96 and "horizontal" control lines 94. "Vertical" control lines 96 have the same width therealong, whereas "horizontal" control lines 94 have alternating wide and narrow portions, as shown.

Figure 17C:
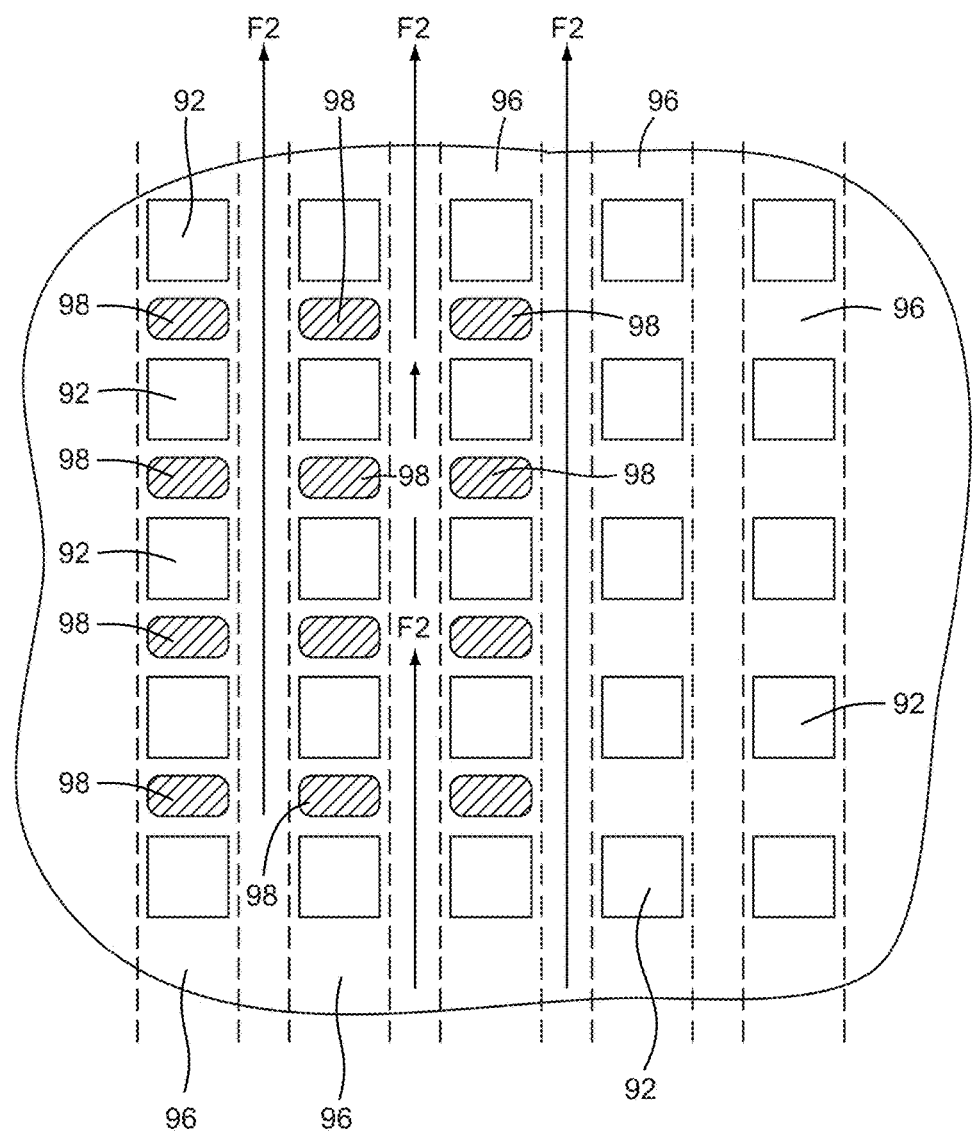
Figure 17D:
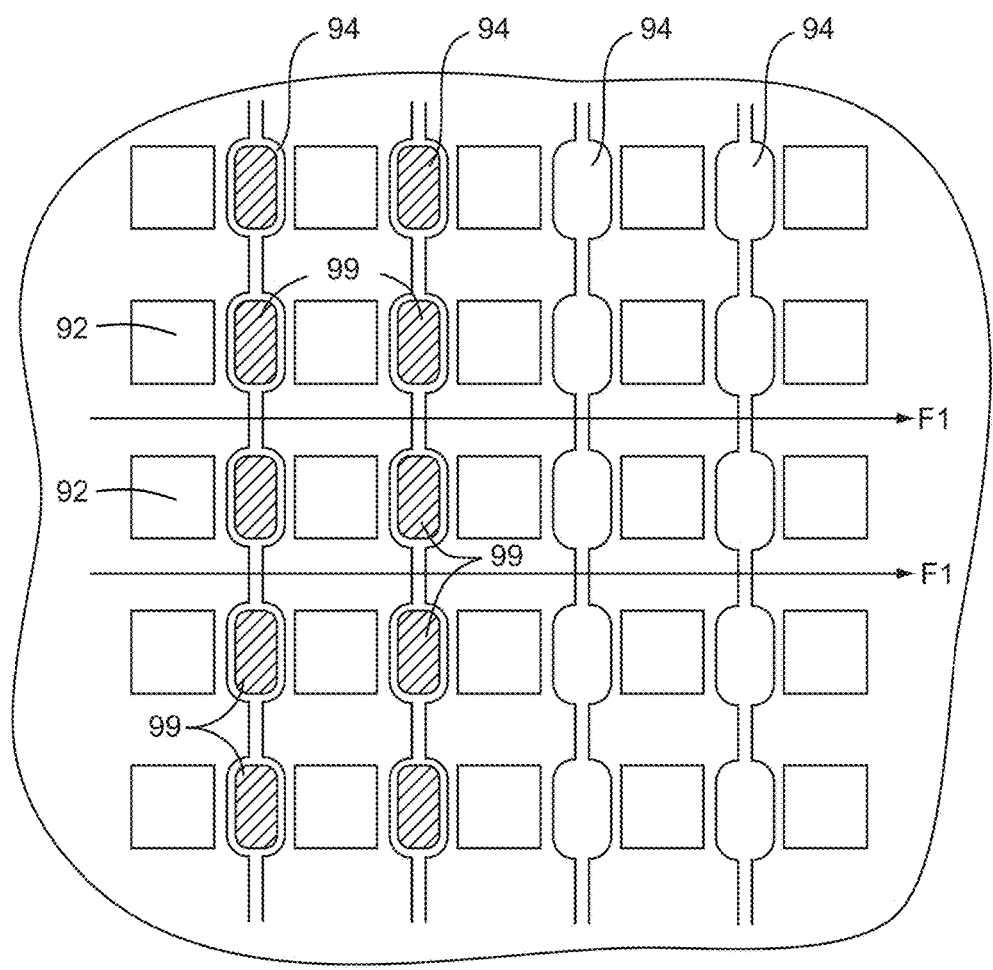

Elastomeric layer 95 is positioned over top of elastomeric layer 90 such that "vertical" control lines 96 are positioned over posts 92 as shown in FIG. 17C and "horizontal" control lines 94 are positioned with their wide portions between posts 92, as shown in FIG. 17D.

As can be seen in FIG. 17C, when "vertical" control lines 96 are pressurized, the membrane of the integrated structure formed by the elastomeric layer initially positioned between layers 90 and 95 in regions 98 will be deflected downwardly over the array of flow channels such that flow in only able to pass in flow direction F2 (i.e.: vertically), as shown.

As can be seen in FIG. 17D, when "horizontal" control lines 94 are pressurized, the membrane of the integrated structure formed by the elastomeric layer initially positioned between layers 90 and 95 in regions 99 will be deflected downwardly over the array of flow channels, (but only in the regions where they are widest), such that flow in only able to pass in flow direction F1 (i.e.: horizontally), as shown.

The design illustrated in FIGS. 17A-D allows a switchable flow array to be constructed from only two elastomeric layers, with no vertical vias passing between control lines in different elastomeric layers required. If all vertical flow control lines 94 are connected, they may be pressurized from one input. The same is true for all horizontal flow control lines 96.

9. Cell Pen

In yet a further application of the present invention, an elastomeric structure can be utilized to manipulate organisms or other biological material. FIGS. 18A-18D show plan views of one embodiment of a cell pen structure in accordance with the present invention.

Cell pen array 4400 features an array of orthogonally-oriented flow channels 4402, with an enlarged "pen" structure 4404 at the intersection of alternating flow channels. Valve 4406 is positioned at the entrance and exit of each pen structure 4404. Peristaltic pump structures 4408 are positioned on each horizontal flow channel and on the vertical flow channels lacking a cell pen structure.

Figure 18A:
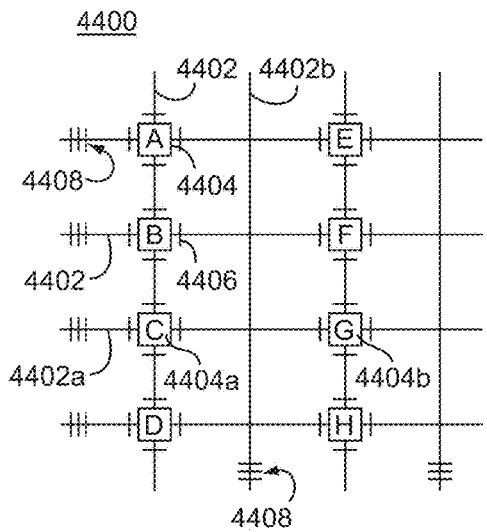
FIGS. 18A to 18D show plan views of one embodiment of a cell pen array structure.
Figure 18C:
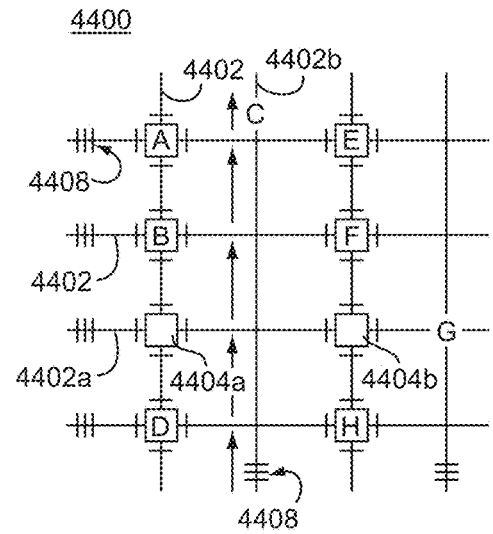
Figure 18B:
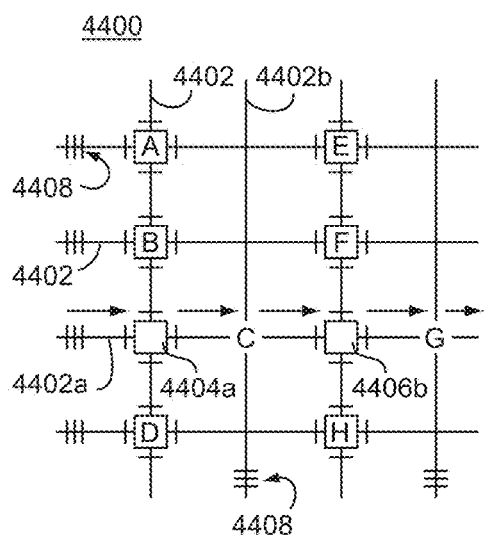
Figure 18D:
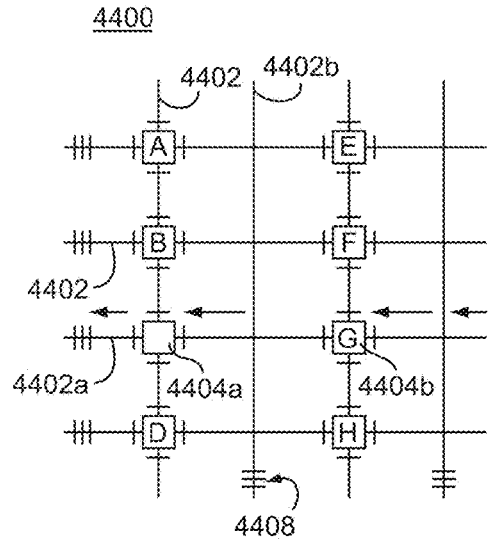

Cell pen array 4400 of FIG. 18A has been loaded with cells A-H that have been previously sorted. FIGS. 18B-18C show the accessing and removal of individually stored cell C by 1) opening valves 4406 on either side of adjacent pens 4404a and 4404b, 2) pumping horizontal flow channel 4402a to displace cells C and G, and then 3) pumping vertical flow channel 4402b to remove cell C. FIG. 18D shows that second cell G is moved back into its prior position in cell pen array 4400 by reversing the direction of liquid flow through horizontal flow channel 4402a. The cell pen array 4404 described above is capable of storing materials within a selected, addressable position for ready access.

While the embodiment shown and described above in connection with FIGS. 18A-18D utilizes linked valve pairs on opposite sides of the flow channel intersections, this is not required by the present invention. Other configurations, including linking of adjacent valves of an intersection, or independent actuation of each valve surrounding an intersection, are possible to provide the desired flow characteristics. With the independent valve actuation approach however, it should be recognized that separate control structures would be utilized for each valve, complicating device layout.

10. Cell Cage

The cell pen array 4404 described above is capable of storing materials within a selected, addressable position for ready access. However, living organisms such as cells may require a continuous intake of foods and expulsion of wastes in order to remain viable. Accordingly, FIGS. 19A and 19B show plan and cross-sectional views (along line 45B-45B') respectively, of one embodiment of a cell cage structure in accordance with the present invention.

Cell cage 4500 is formed as an enlarged portion 4500a of a flow channel 4501 in an elastomeric block 4503 in contact with substrate 4505. Cell cage 4500 is similar to an individual cell pen as described above in FIGS. 18A-18D, except that ends 4500b and 4500c of cell cage 4500 do not completely enclose interior region 4500a. Rather, ends 4500a and 4500b of cage 4500 are formed by a plurality of retractable pillars 4502.

Specifically, control channel 4504 overlies pillars 4502. When the pressure in control channel 4504 is reduced, elastomeric pillars 4502 are drawn upward into control channel 4504, thereby opening end 4500b of cell cage 4500 and permitting a cell to enter. Upon elevation of pressure in control channel 4504, pillars 4502 relax downward against substrate 4505 and prevent a cell from exiting cage 4500.

Elastomeric pillars 4502 are of a sufficient size and number to prevent movement of a cell out of cage 4500, but also include gaps 4508 which allow the flow of nutrients into cage interior 4500a in order to sustain cell(s) stored therein. Pillars 4502 on opposite end 4500c are similarly configured beneath second control channel 4506 to permit opening of the cage and removal of the cell as desired.

11. Cross-Channel Injector

The cross-flow channel architecture illustrated shown in FIGS. 18A-18D can be used to perform functions other than the cell pen just described. For example, the cross-flow channel architecture can be utilized in mixing applications.

This is shown in FIGS. 20A-D, which illustrate a plan view of mixing steps performed by a microfabricated structures in accordance another embodiment of the present invention. Specifically, portion 7400 of a microfabricated mixing structure comprises first flow channel 7402 orthogonal to and intersecting with second flow channel 7404. Control channels 7406 overlie flow channels 7402 and 7404 and form valve pairs 7408a-b and 7408c-d that surround each intersection 7412.

As shown in FIG. 20A, valve pair 7408c-d is initially opened while valve pair 7408a-b is closed, and fluid sample 7410 is flowed to intersection 7412 through flow channel 7404. Valve pair 7408a-b is then actuated, trapping fluid sample 7410 at intersection 7412.

Next, as shown in FIG. 20B, valve pairs 7408c-d are closed and 7408a-b are opened, such that fluid sample 7410 is injected from intersection 7412 into flow channel 7402 bearing a cross-flow of fluid. The process shown in FIGS. 20A-B can be repeated to accurately dispense any number of fluid samples down cross-flow channel 7402.

While the embodiment of a process-channel flow injector structure shown in FIGS. 20A-B feature channels intersecting at a single junction, this is not required by the present invention. Thus FIG. 20C shows a simplified plan view of another embodiment of an injection structure in accordance with the present invention, wherein junction 7450 between intersecting flow channels 7452 is extended to provide additional volume capacity. FIG. 20D shows a simplified plan view of yet another embodiment of an injection structure in accordance with the present invention, wherein elongated junction 7460 between intersecting flow channels 7462 includes branches 7464 to provide still more injection volume capacity.

12. Rotary Mixing Structure

Microfluidic control and flow channels in accordance with embodiments of the present invention may be oriented to rotary pump design which circulates fluid through a closed circuit flow channel. As used herein the term "closed circuit" has the meaning known in the art and refers to configurations that are circular and variations thereof such as ellipsoids and ovals, as well as flow circuit paths having corners as are created by triangular, rectangular, or more complex shapes.

Figure 21:
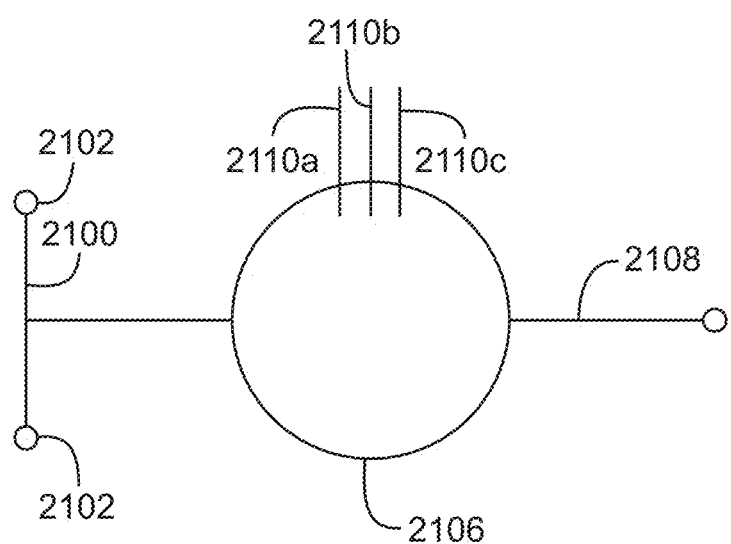
FIG. 21 shows a plan view of one embodiment of a rotary mixing structure in accordance with the present invention.

As illustrated in FIG. 21, a layer with flow channels 2100 has a plurality of sample inputs 2102, a mixing T-junction 2104, a central circulation loop 2106 (i.e., the substantially circular flow channel), and an output channel 2108. The overlay of control channels with a flow channel can form a microvalve. This is so because the control and flow channels are separated by a thin elastomeric membrane that can be deflected into the flow channel or retracted therefrom.

The substantially circular central loop and the control channels that intersect with it form the central part of the rotary pump. The pump(s) which cause solution to be flowed through the substantially circular flow channel consist of a set of at least three control channels 2110a-c that are adjacent to one another and which intersect the substantially circular branch flow channel 2106 (i.e., the central loop).

When a series of on/off actuation sequences, such a 001, 011, 010, 110, 100, 101, are applied to the control channels, the fluid in the central loop can be peristaltically pumped in a chosen direction, either clockwise or counterclockwise. The peristaltic pumping action results from the sequential deflection of the membranes separating the control channels and flow channel into or out of the flow channel.

In general, the higher the actuation frequency, the faster the fluid rotates through the central loop. However, a point of saturation may eventually be reached at which increased frequency does not result in faster fluid flow. This is primarily due to limitations in the rate at which the membrane can return to an unactuated position.

While the system shown in FIG. 21 shows each pump including three control channels, a different number of control channels can be utilized, for example, a single serpentine control channel having multiple cross-over points could be used.

A variety of different auxiliary flow channels which are in fluid communication with the central loop can be utilized to introduce and withdrawn sample and reactant solutions from the central loop. Similarly, one or more exit or outlet flow channels in fluid communication with the central loop can be utilized to remove solution from the central loop. For example, control valves can be utilized at the inlet(s) and the outlet(s) to prevent solution flow into or out from the central loop.

Flow channel sizes and shapes can vary. With certain devices, the diameter of the channel tends to range from about 1 mm to 2 cm, although the diameter can be considerably larger in certain devices (e.g., 4, 6, 8, or 10 cm). Limits on how small the diameter of the circular flow channel can be are primarily a function of the limits imposed by the multilayer soft lithography processes. Channel widths (either flow or control) usually vary between 30 μm and 250 μm. However, channel width in some devices is as narrow as 1 um. Channels of larger widths can also be utilized, but generally require some type of structural support within the flow channel. Channel height generally varies between 5 and 50 μm. In flow channels having a width of 100 μm or less, the channel height may be 1 μm or smaller. The flow channel is typically rounded to allow for complete blockage of the channel once the membrane is deflected into the channel. In some devices, the channels have shapes such as octagons or hexagons. In certain devices, the flow channels are rounded and 100 μm wide and 10 μm high and control channels are 100 μm wide and 10 μm high. One system that has been utilized in certain studies has utilized a central loop having a diameter of 2 cm, a flow channel width of 100 μm and a depth of 10 μm.

While the channels typically have the foregoing sizes and shapes, it should be recognized that the devices provided herein are not limited to these particular sizes and shapes. For example, branches present in a closed circuit flow channel may serve to control the dispersion and hence mixing of materials flowed therein.

13. Microfluidic Large-Scale Integration

The previous section has described monolithic microvalves that are substantially leakproof and scalable, and has also described methods for fabricating these microvalves. For the relatively simple assemblies of microfluidic valves previously described, each fluid flow channel may be controlled by its own individual valve control channel. However, such a non-integrated control strategy cannot be practicably implemented for more complex assemblies comprising thousands or even tens of thousands of individually addressable valves. Accordingly, a variety of techniques may be applied alone or in combination to allow for the fabrication of large scale integrated microfluidic devices having individually addressable valves.

Techniques useful for implementing large scale integrated microfluidic structures in accordance with embodiments of the present invention are discussed in detail in U.S. non-provisional patent application Ser. No. 10/670,997, now U.S. Pat. No. 7,143,785. One technique allowing for the fabrication of large scale integrated microfluidic devices is the use of multiplexor structures.

Figure 22A:
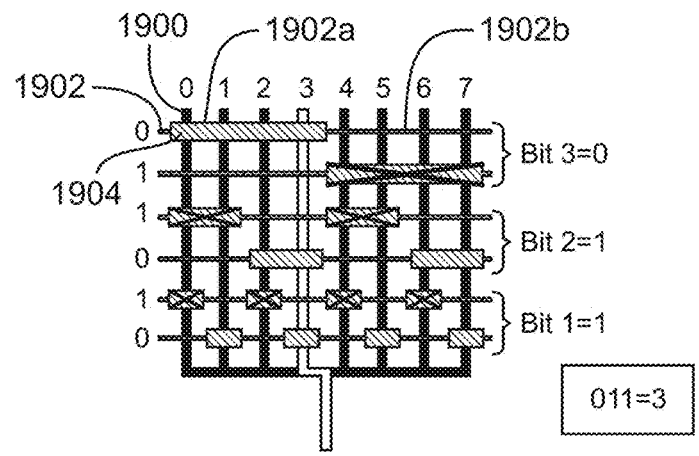
FIG. 22A shows a simplified plan view illustrating a binary tree microfluidic multiplexor operational diagram.

The use of multiplexor structures has previously been described in connection with a single set of control lines overlying a single set of flow channels. FIG. 22A shows a simplified plan view illustrating a microfluidic binary tree multiplexor operational diagram. Flow channels 1900 defined in a lower elastomer layer contain the fluid of interest, while control channels 1902 defined in an overlying elastomer layer represent control lines containing an actuation fluid such as air or water. Valves 1904 are defined by the membranes formed at the intersection of the wider portion 1902a of a control channel 1902 with a flow channel 1900. The actuation pressure is chosen so that only the wide membranes are fully deflected into the flow channel 1900. Specifically, the multiplexor structure is based on the sharp increase in pressure required to actuate a valve as the ratio of control channel width:flow channel width is decreased.

The multiplexor structure shown in FIG. 22A is in the form of a binary tree of valves where each stage selects one out of two total groups of flow channels. In the multiplexor embodiment shown in FIG. 22A, each combination of open/closed valves in the multiplexor selects for a single channel, so that n flow channels can be addressed with only 2 $\log_2 n$ control channels.

By using multiplexed valve systems, the power of the binary system becomes evident: only about 20 control channels are required to specifically address 1024 flow channels. This allows a large number of elastomeric microvalves to perform complex fluidic manipulations within these devices, while the interface between the device and the external environment is simple and robust.

Figure 22B:
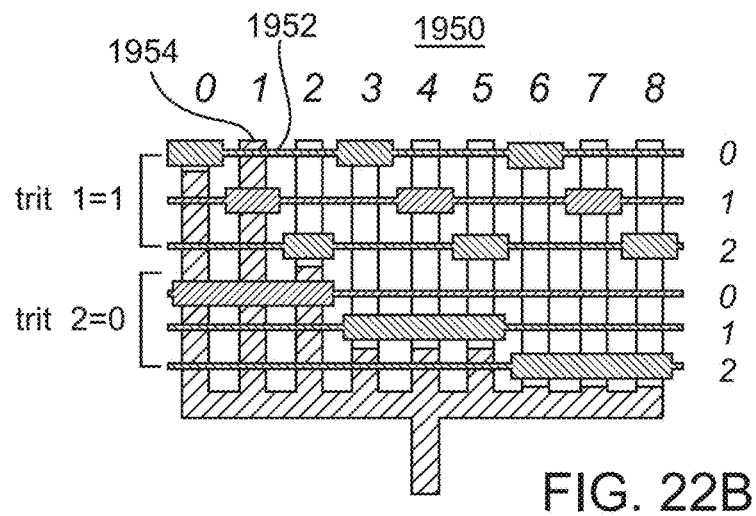
FIG. 22B shows a simplified plan view illustrating a tertiary tree microfluidic multiplexor operational diagram.

FIG. 22B shows a simplified plan view of an alternative embodiment of a multiplexor structure in accordance with the present invention. Multiplexor structure 1950 comprises control channels 1952 formed in an elastomer layer overlying flow channels 1954 of an underlying elastomer layer. Operating under the same physical principles of the multiplexor of FIG. 22A, multiplexor 1950 comprises a tertiary tree of valves, where each stage comprises three bits ("a trit") and selects one out of three total groups of flow channels. Each combination of open/closed valves in the multiplexor 1950 selects for a single channel, so that n flow channels can be addressed with only 3 $\log_3 n$ control channels.

Figure 22C:
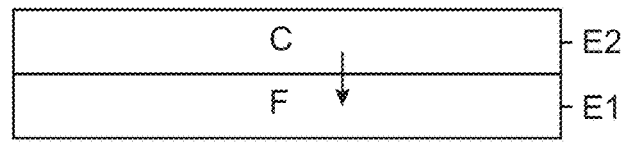
FIG. 22C shows a simplified cross-sectional view of the general microfluidic architecture of the devices of FIGS. 22A-B.

The general microfluidic flow architecture of either of the basic multiplexor devices shown in FIGS. 22A-B may be generically represented in the simplified cross-sectional view of FIG. 22C, wherein second elastomer layer E2 defining control channel network C overlies first elastomer layer E1 defining flow channel network F.

The base 3 multiplexor of FIG. 22B is the most efficient design that may be used to address large numbers of 'flow" channels. This is because the x $\log_x$ n valve is minimized where e is used for the base of the log. As fractions are not used for the base of an actual multiplexor, the most efficient multiplexor structure is achieved where the value of x=3, the integer closest to e (~2.71828).

To highlight this point, TABLE 2 compares the efficiency of the base 2 multiplexor with the base 3 multiplexor.

TABLE 2

| | Number of Flow Lines Controlled by Control Lines | | Enhanced Efficiency of Base 3 Multiplexor Structure |
|---|---|---|---|
| Number of Control Lines | Base 2 Multiplexor | Base 3 Multiplexor | |
| 6 | 8 | 9 | +1 |
| 9 | 23 | 27 | +4 |
| 12 | 64 | 81 | +17 |
| 15 | 181 | 243 | +62 |
| 18 | 512 | 729 | +217 |

While the above description has focused upon various multiplexor structures utilizing stages having the same base number, this is not required by the present invention. Alternative embodiments of multiplexor structures in accordance with the present invention may comprise stages of unlike base numbers. For example, a two-stage multiplexor consisting of a bit stage and a trit stage represents the most efficient way of addressing six flow channels. The order of the stages is arbitrary, and will always result in the same number of flow lines being controlled. The use of multiplexor structures comprising different binary and tertiary stages allows the efficient addressing of any number of "flow" channels that are the product of the numbers 2 and 3.

Figure 23:
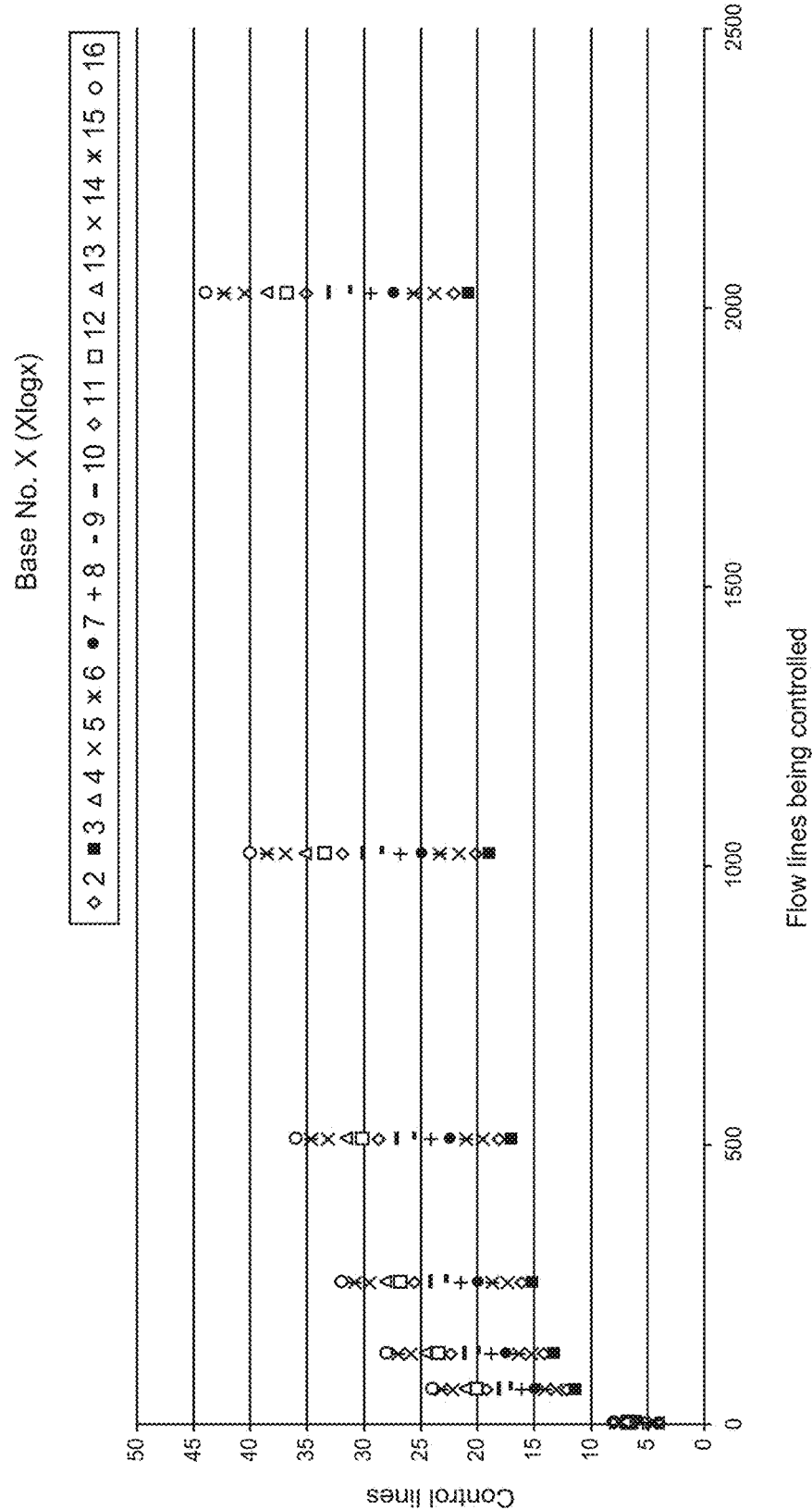
FIG. 23 plots the number of control lines versus the number of flow lines being controlled, for multiplexors of various base numbers.

A multiplexor may conceivably use any base number. For example, five may also be used as the base number, if necessary. However, efficiency in utilization of control lines diminishes as the number of control lines moves away from the value of e. This is shown in FIG. 23, which plots the number of control lines versus the number of flow lines being controlled, for multiplexor structures having different base numbers.

Figure 24:
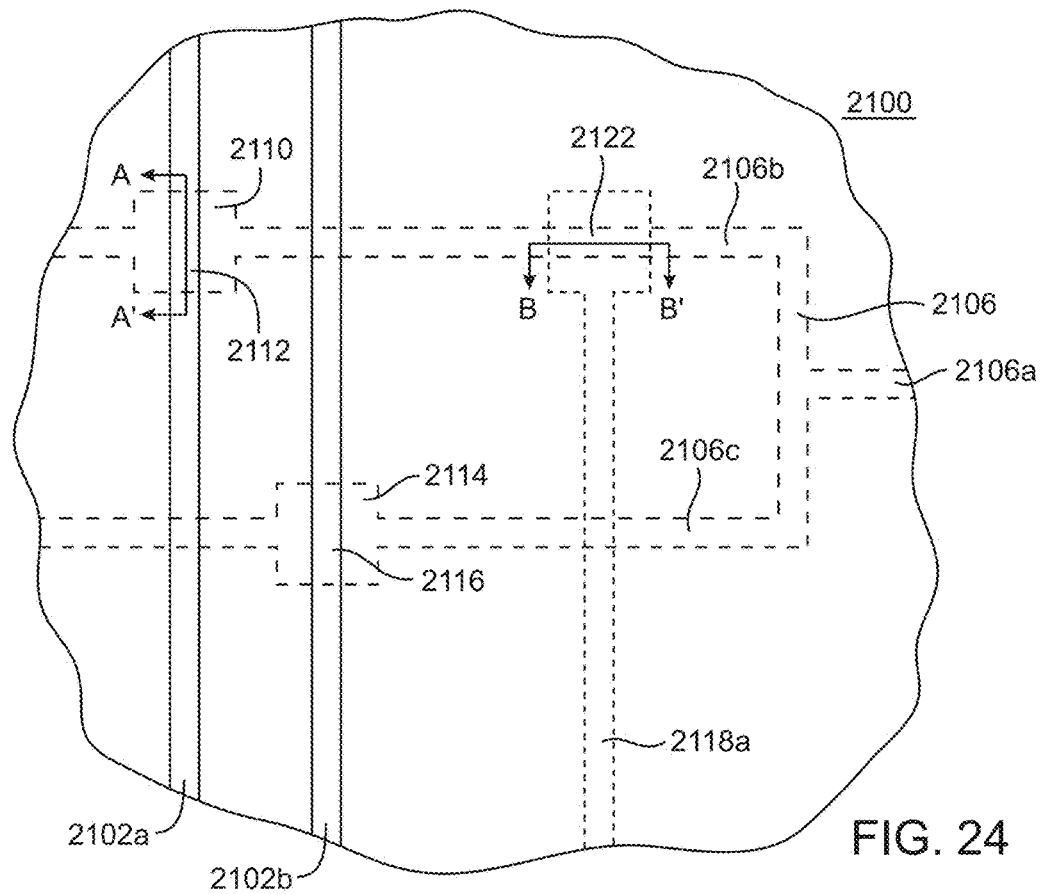
FIG. 24 shows a simplified plan view of an embodiment of a microfluidic structure utilizing control channels to control other control channels.
Figure 24A:
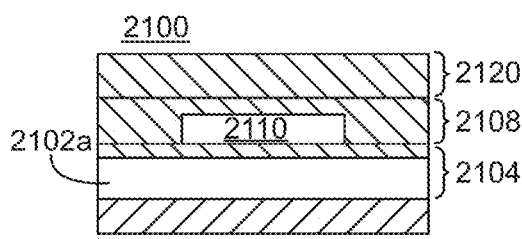
FIG. 24A shows a simplified cross-sectional view of the structure of FIG. 24 taken along the line A-A'
Figure 24B:
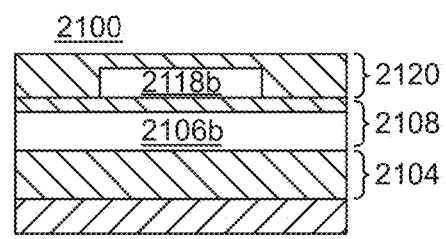
FIG. 24B shows a simplified cross-sectional view of the structure of FIG. 24 taken along the line B-B'.

Another technique allowing for the fabrication of large scale integrated (LSI) microfluidic devices is the use of multiple layers of control lines. FIGS. 24-24B illustrate this approach. FIG. 24 shows a plan view of one embodiment of a microfluidic device having a first control line controlled by a second control line. FIG. 24A shows a cross-sectional view of the microfluidic device of FIG. 24, taken along line A-A'. FIG. 24B shows a cross-sectional view of the microfluidic device of FIG. 24, taken along line B-B'.

Microfluidic structure 2100 comprises two flow channels 2102a-b formed in lowermost elastomer layer 2104. First control channel network 2106 including first inlet 2106a in fluid communication with first and second branches 2106b and 2106c, is formed in a second elastomer layer 2108 overlying first elastomer layer 2104. First branch 2106b of first control channel network 2106 includes widened portion 2110 overlying first flow channel 2102a to define first valve 2112. Second branch 2106c of first control channel network 2106 includes widened portion 2114 overlying second flow channel 2102b to define second valve 2116.

Second control channel network 2118 comprising third control channel 2118a is formed in third elastomer layer 2120 overlying second elastomer layer 2108. Third control channel 2118a includes widened portion 2118b overlying first branch 2106b of first control channel network 2106 to form valve 2122.

The microfluidic device illustrated in FIGS. 24-24B may be operated as follows. A fluid that is to be manipulated is present in flow channels 2102a and 2102b. Application of a pressure to the first control channel network 2106 causes the membranes of valves 2112 and 2116 to deflect downward into their respective flow channels 2102a and 2102b, thereby valving flow through the flow channels.

Application of a pressure to second control channel network 2118 causes the membrane of valve 2122 to deflect downward into underlying first branch 2106c only of first control channel network 2106. This fixes the valve 2112 in its deflected state, in turn allowing the pressure within the first control channel network 2106 to be varied without affecting the state of valve 2112.

Figure 25:
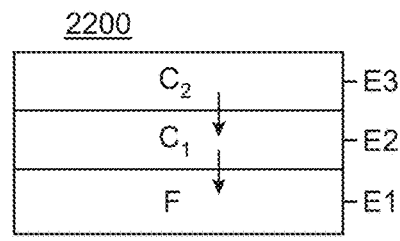
FIG. 25 shows a simplified cross-sectional view of the general microfluidic architecture of the device of FIGS. 24-24B.

The general architecture of the microfluidic device depicted in FIGS. 24-24B is summarized in the simplified cross-sectional view of FIG. 25. Specifically, elastomeric device 2200 comprises lowest elastomer layer E1 defining flow channel network F, underlying second elastomer layer E2 defining first control channel network C1. First control channel network C1 in turn underlies second control channel network C2 that is defined within third elastomer layer E3.

While the embodiment of the microfluidic device of FIGS. 24-24B is described as being fabricated from three separate elastomer layers, this is not required by the present invention. Large scale integrated microfluidic structures in accordance with embodiments of the present invention featuring multiplexed control lines may be fabricated utilizing only two elastomer layers. This approach is shown and illustrated in connection with FIGS. 26-26B.

Figure 26:
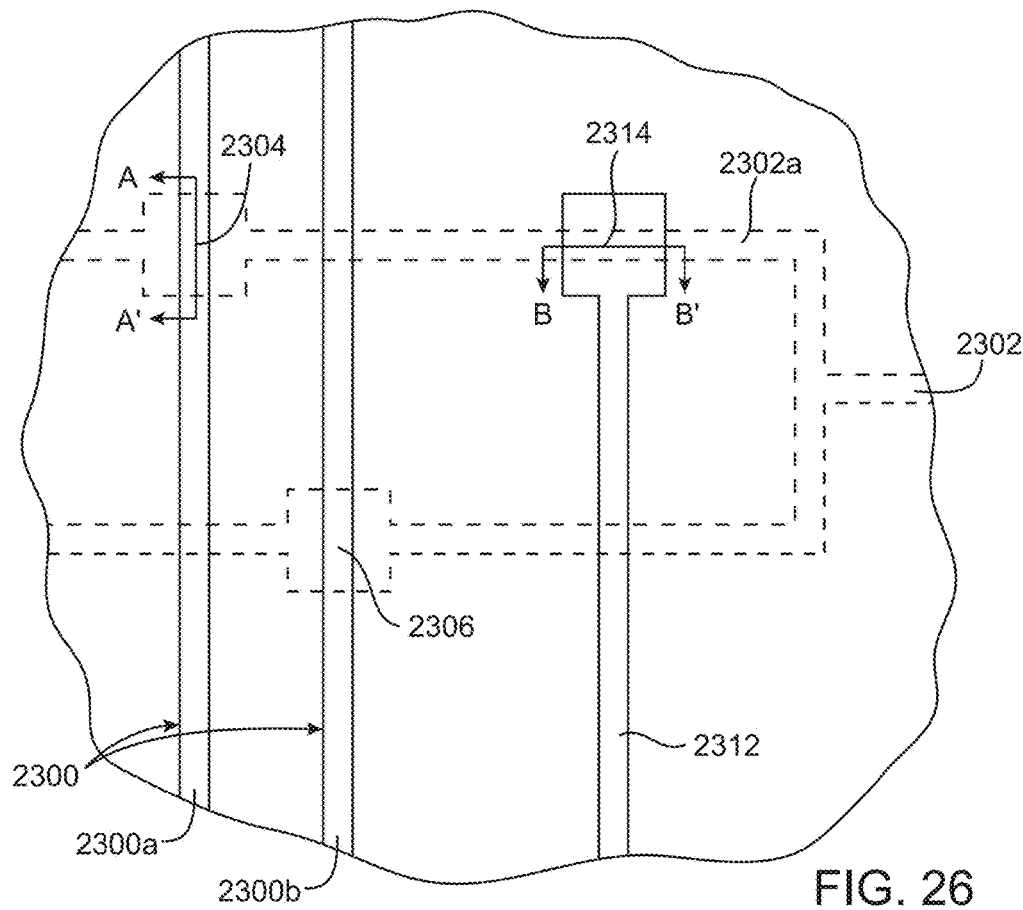
FIG. 26 shows a simplified plan view of an alternative embodiment of a microfluidic structure utilizing control channels to control other control channels.
Figure 26A:
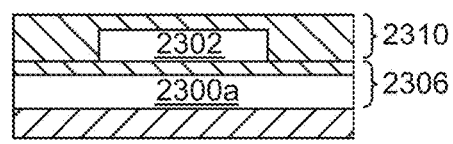
FIG. 26A shows a simplified cross-sectional view of the structure of FIG. 26 taken along the line A-A'.

FIG. 26 shows a simplified plan view of a microfabricated elastomer device including first and second flow channels 2300a and 2300b, and first branched control channel network 2302 overlying flow channels 2300a and 2300b to define valves 2304 and 2306 respectively. FIG. 26A shows a cross-sectional view of the microfabricated elastomer device of FIG. 26, taken along line A-A', with flow channel 2300a defined in lower elastomer layer 2306, and first control channel 2302 defined in upper elastomer layer 2310.

Figure 26B:
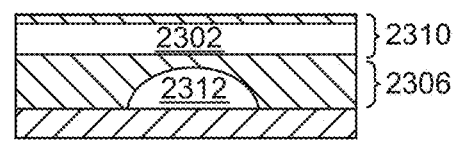
FIG. 26B shows a simplified cross-sectional view of the structure of FIG. 26 taken along the line B-B'.

Lower elastomer layer 2308 further comprises a second control channel network 2312 running underneath first control channel 2302 to define valve 2314. Accordingly, FIG. 26B shows a cross-sectional view of the microfabricated elastomer device of FIG. 26, taken along line B-B'. While present in the same (lower) elastomer layer 2308, flow channel network 2300 and second control channel network 2312 are separate and do not intersect one another.

As represented in the simplified cross-sectional view of FIG. 27, separate flow channel network F and control channel network C2 may thus be present on a single (lower) elastomer layer E1 that is overlaid by another elastomer layer E2 defining only a control channel network C1.

The microfluidic device illustrated in FIGS. 26-26B may be operated as follows. A fluid that is to be manipulated is present in flow channels 2300a and 2300b. Application of a pressure to the first control channel network 2302 causes the membranes of valves 2304 to deflect downward into their respective flow channels 2300a and 2300b, thereby valving flow through the flow channels.

Application of a pressure to second control channel network 2312 causes the membrane of valve 2314 to deflect upward into the overlying branch of first control channel network 2302. This fixes the valve 2314 in its deflected state, in turn allowing the pressure within the first control network 2302 to be varied without affecting the state of valve 2314. In contrast with the embodiment shown in FIG. 24, the microfluidic device of FIGS. 26-26B features a valve that operates by deflecting upward into an adjacent control channel in response to an elevated pressure.

Figure 27A:
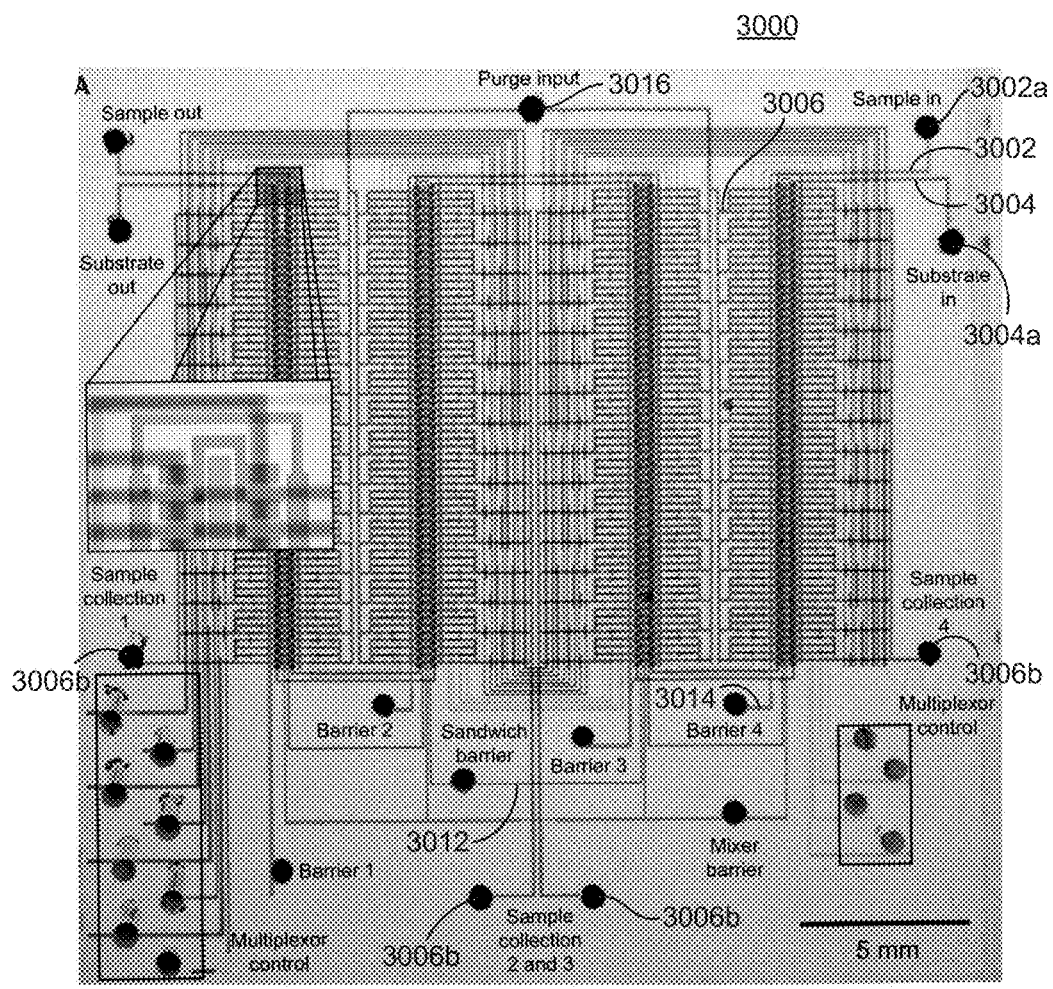
FIG. 27A shows an optical micrograph of a microfluidic comparator chip.
Figure 27B:
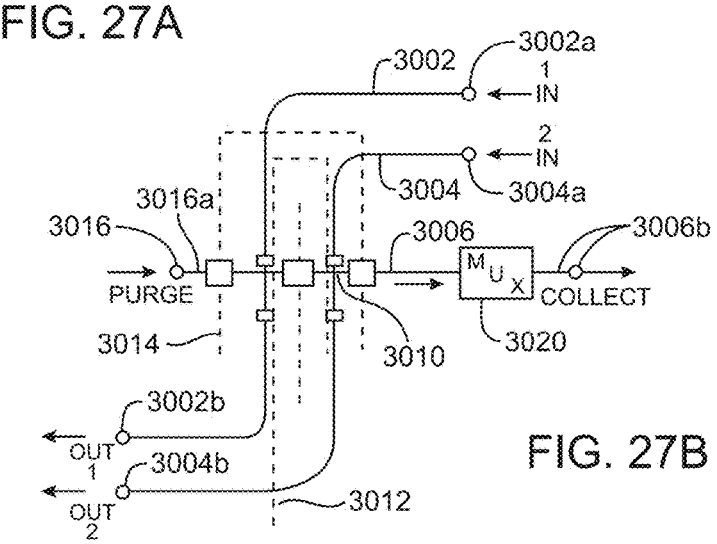
FIG. 27B is a simplified schematic view of the microfluidic comparator chip of FIG. 27A.

FIG. 27A shows an optical micrograph of a microfluidic comparator chip 3000 microfabricated with large scale integration technology which is analogous to an array of 256 comparators. Specifically, a second device containing 2056 microvalves was designed which is capable of performing more complex fluidic manipulations. The various inputs have been loaded with colored food dyes to visualize the channels and sub-elements of the fluidic logic. FIG. 27B shows a simplified schematic plan view of one portion of the chip of FIG. 27A.

Comparator chip 3000 is formed from a pair of parallel, serpentine flow channels 3002 and 3004 having inlets 3002a and 3004a respectively, and having outlets 3002b and 3004b respectively, that are intersected at various points by branched horizontal rows of flow channels 3006. Portions of the horizontal flow channels located between the serpentine flow channels define mixing locations 3010.

A first barrier control line 3012 overlying the center of the connecting channels is actuable to create adjacent chambers, and is deactivable to allow the contents of the adjacent chambers to mix. A second barrier control line 3014 doubles back over either end of the adjacent chambers to isolate them from the rest of the horizontal flow channels.

One end 3006a of the connecting horizontal flow channel 3006 is in fluid communication with pressure source 3016, and the other end 3006b of the connecting horizontal flow channel 3006 is in fluid communication with a sample collection output 3018 through multiplexor 3020.

Figure 27C:
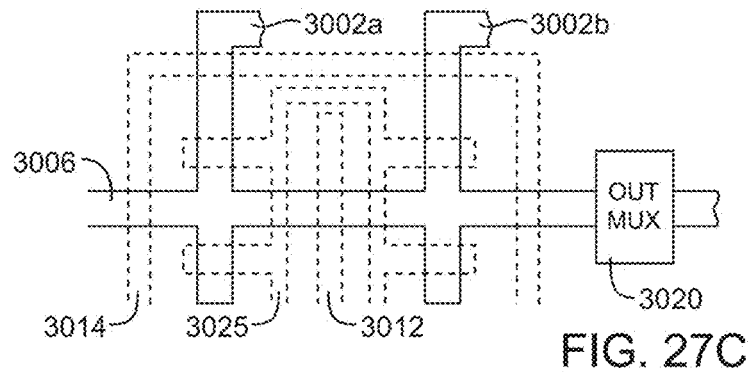
FIGS. 27C to 27H are enlarged simplified plan views showing loading of the chamber of the microfluidic structure of FIG. 27A.
Figure 27D:
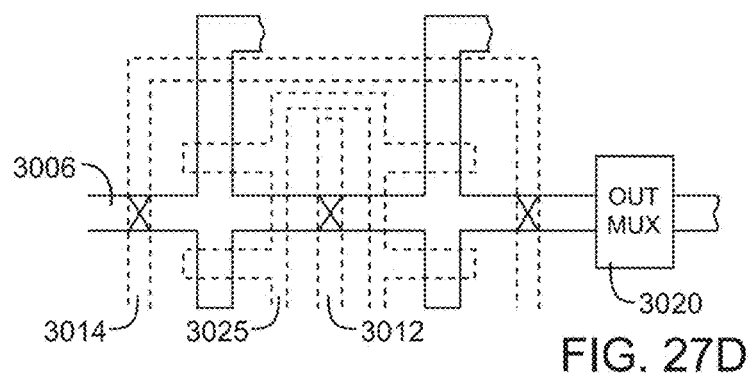
Figure 27E:
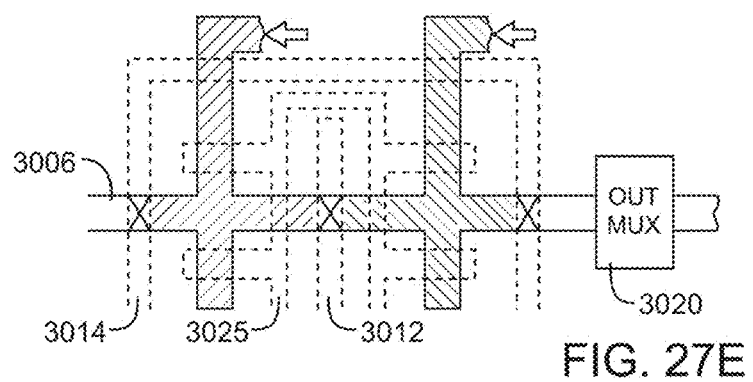
Figure 27F:
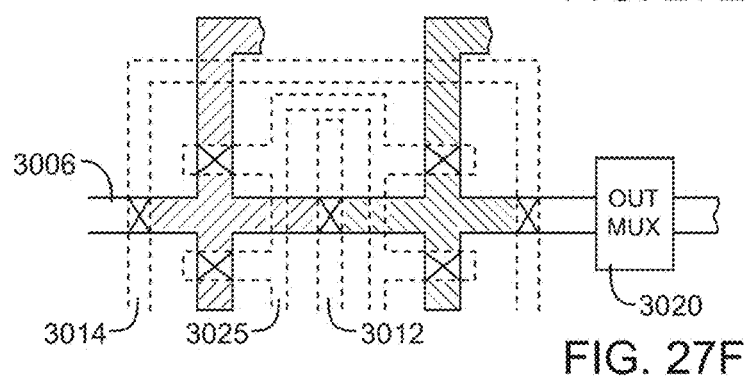

FIGS. 27C-H show simplified enlarged plan views of operation of one mixing element of the structure of FIGS. 27A-B. FIG. 27C shows the mixing element prior to loading, with the mixer barrier control line and wrap-around barrier control line unpressurized. FIG. 27D shows pressurization of the wrap-around barrier control line and barrier mixer line to activate isolation valves and separation valve to define adjacent chambers 3050 and 3052. FIG. 27E shows loading of the chambers with a first component and a second component by flowing these materials down the respective flow channels. FIG. 27F shows pressurization of the vertical compartmentalization control line 3025 and the isolation to define the adjacent chambers.

Figure 27G:
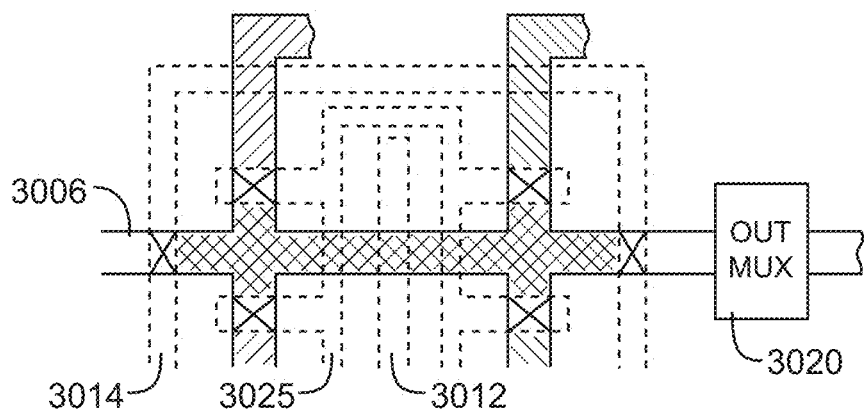

FIG. 27G shows depressurization of the mixing barrier control channel to deactivate the separation barrier valve, thereby allowing the different components present in the adjacent chambers to mix freely.

Figure 27H:
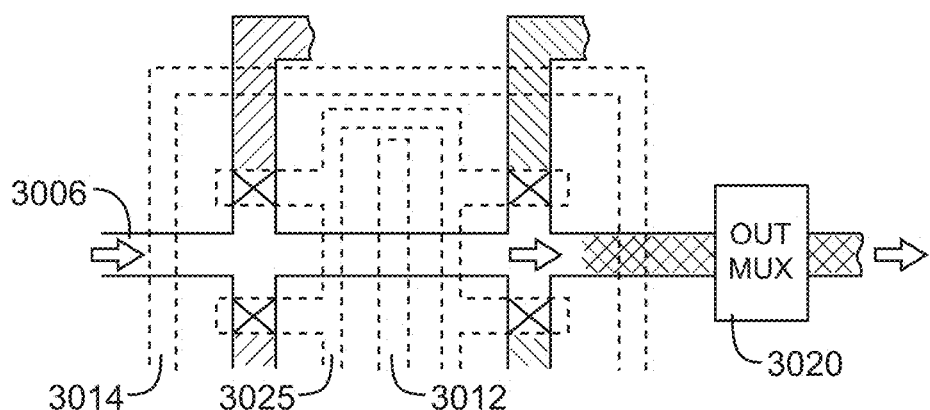

FIG. 27H shows the deactivation of barrier the isolation control line, causing deactivation of the isolation valves, followed by application of pressure to the control line and deactivation of the multiplexor to allow the combined mixture to be recovered.

In the case of the device shown in FIGS. 27A-H, two different reagents can be separately loaded, mixed pair wise, and selectively recovered, making it possible to perform distinct assays in 256 sub-nanoliter reaction chambers and then recover a particularly interesting reagent. The microchannel layout consists of four central columns in the flow layer consisting of 64 chambers per column, with each chamber containing ~750 pL of liquid after compartmentalization and mixing. Liquid is loaded into these columns through two separate inputs under low external pressure (~20 kPa), filling up the array in a serpentine fashion. Barrier valves on the control layer function to isolate the sample fluids from each other and from channel networks on the flow layer used to recover the contents of each individual chamber. These networks function under the control of a multiplexor and several other control valves.

The storage array and comparator microfluidic devices shown in FIGS. 27A-H was fabricated with multilayer soft lithography techniques using two distinct layers. The "control" layer, which harbors all channels required to actuate the valves, is situated on top of the "flow" layer, which contains the network of channels being controlled. A valve is created where a control channel crosses a flow channel. The resulting thin membrane in the junction between the two channels can be deflected by hydraulic or pneumatic actuation. All biological assays and fluid manipulations are performed on the "flow" layer.

Master molds for the microfluidic channels were made by spin-coating positive photoresist (Shipley SJR 5740) on silicon 9 µm high and patterning them with high resolution (3386 dpi) transparency masks. The channels on the photoresist molds were rounded at 120° C. for 20 minutes to create a geometry that allows full valve closure.

The devices were fabricated by bonding together two layers of two-part cure silicone (Dow Corning Sylgard 184) cast from the photoresist molds. The bottom layer of the device, containing the "flow" channels, is spin-coated with 20:1 part A:B Sylgard at 2500 rpm for 1 minute. The resulting silicone layer is ~30 µm thick. The top layer of the device, containing the "control" channels, is cast as a thick layer (~0.5 cm thick) using 5:1 part A:B Sylgard using a separate mold. The two layers are initially cured for 30 minutes at 80° C.

Control channel interconnect holes are then punched through the thick layer (released from the mold), after which it is sealed, channel side down, on the thin layer, aligning the respective channel networks. Bonding between the assembled layers is accomplished by curing the devices for an additional 45-60 minutes at 80° C. The resulting multilayer devices are cut to size and mounted on RCA cleaned No. 1, 25 mm square glass coverslips, or onto coverslips spin coated with 5:1 part A:B Sylgard at 5000 rpm and cured at 80° C. for 30 minutes, followed by incubation at 80° C. overnight.

Simultaneous addressing of multiple non-contiguous flow channels is accomplished by fabricating control channels of varying width while keeping the dimension of the flow channel fixed (100 µm wide and 9 µm high). The pneumatic pressure in the control channels required to close the flow channels scales with the width of the control channel, making it simple to actuate 100 µm×100 µm valves at relatively low pressures (~40 kPa) without closing off the 50 µm×100 µm crossover regions, which have a higher actuation threshold.

Introduction of fluid into these devices is accomplished through steel pins inserted into holes punched through the silicone. Unlike micromachined devices made out of hard materials with a high Young's modulus, silicone is soft and forms a tight seal around the input pins, readily accepting pressures of up to 300 kPa without leakage. Computer-controlled external solenoid valves allow actuation of multiplexors, which in turn allow complex addressing of a large number of microvalves.

II. Characterization and Analysis of Bacteria and Viruses

The microbial ecology of the human gut and other previously inaccessible environments may be characterized and analyzed utilizing microfluidic chips to make genomic DNA (gDNA) libraries from individual bacteria in a highly parallel fashion. The gDNA libraries can be analyzed using high throughput screening or hybridization assays. The ability of microfluidic structures to generate reagents from individual bacteria enables the application of functional genomics to address previously insoluble problems.

Figure 28:
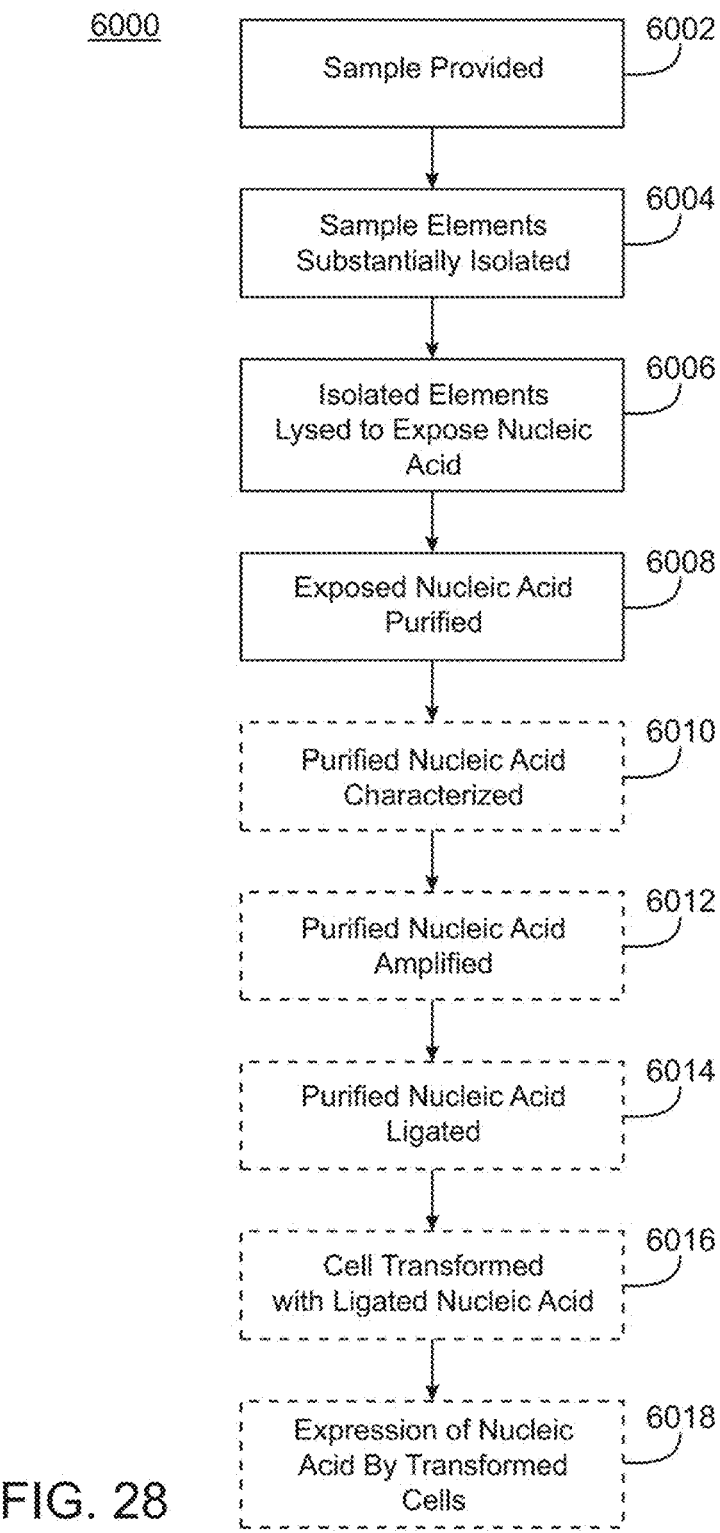
FIG. 28 is a simplified flow chart illustrating steps of manipulating nucleic acids in accordance with embodiments of the present invention.

FIG. 28 shows a simplified flow chart of a generic process 6000 for characterization and analysis in accordance with one embodiment of the present invention. In step 6002, a sample containing bacteria and/or viruses is collected from the environment of interest. In step 6004, the bacteria or virus of interest is substantially physically isolated from other components of the collected sample.

In step 6006, the isolated bacteria or virus is lysed to provide access to the nucleic acid contents thereof. In step 6008, the nucleic acid exposed by cell/virus lysis is purified.

In optimal steps 6010 and 6012, the purified nucleic acid may be characterized and amplified, respectively. Although FIG. 28 shows the step of nucleic acid characterization occurring before amplification, this order of steps is not required by the present invention. In accordance with alternative embodiments, the purified nucleic acid may be amplified prior to characterization.

In still other optional steps, nucleic acid that has been purified in accordance with embodiments of the present invention, may be expressed. Specifically, step 6014 shows the ligation of the purified nucleic acid into a plasmid or vector. Step 6016 shows the transformation of a host cell with the ligated nucleic acid. Step 6018 shows expression of the nucleic acid by the transformed cell.

As described above, one or all of the steps of process 6000 may be performed utilizing microfluidic architectures in accordance with embodiments of the present invention. The following sections summarize particular functions for isolation and characterizing bacteria and viruses, illustrating particular examples of microfluidic structures suitable for performing these functions.

1. Bacterial/Viral Isolation

Figure 29A:
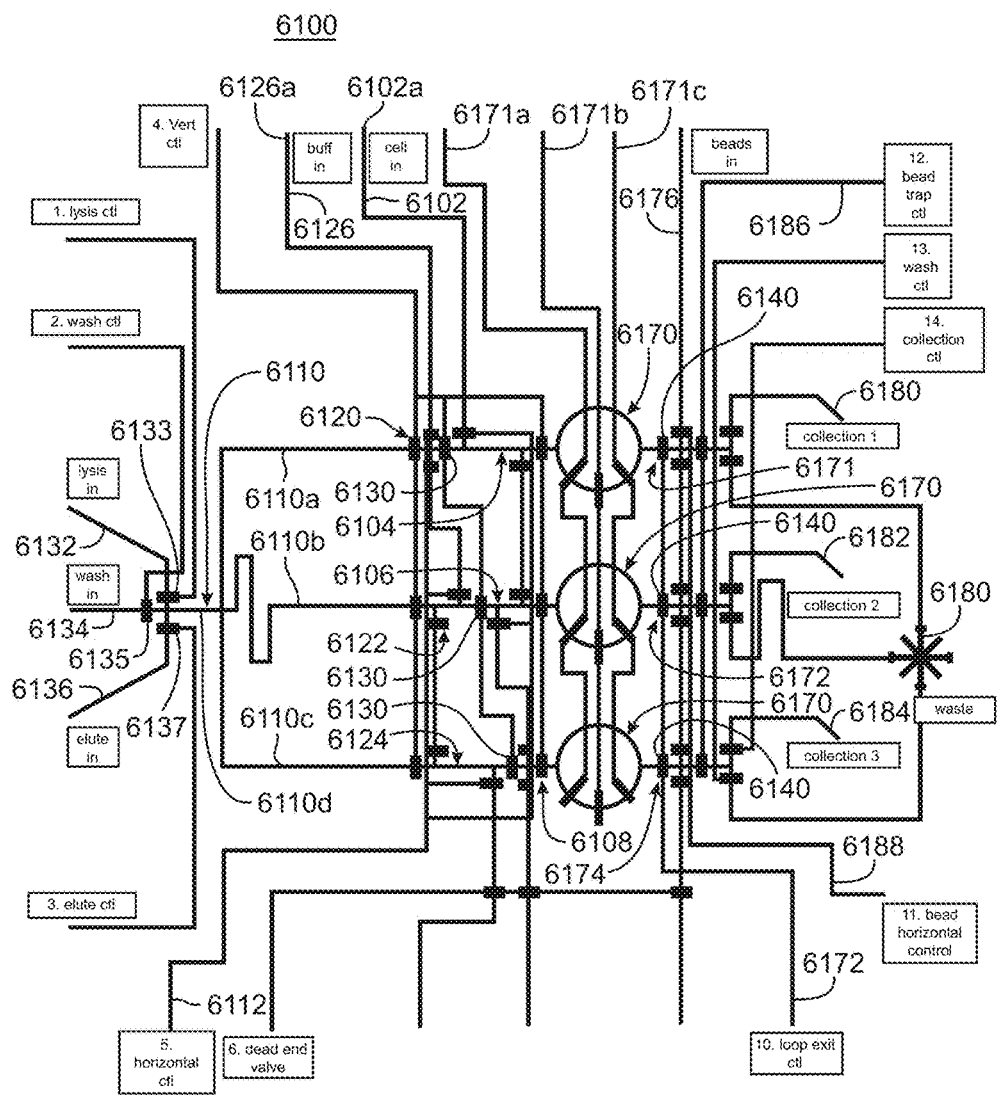
FIG. 29A shows a plan view of one embodiment of a microfluidic architecture in accordance with the present invention allowing cell lysis and purification of DNA present therein.
Figure 29D:
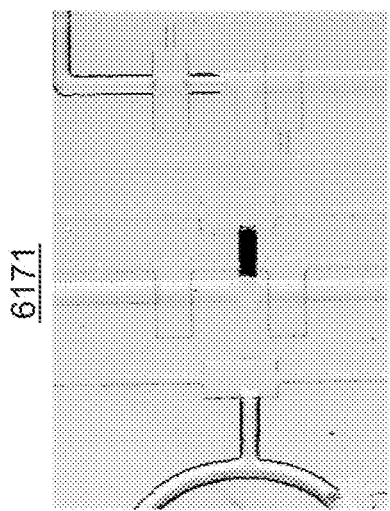
FIGS. 29B to 29D show photographs of enlarged regions of the microfluidic architecture of FIG. 22A.
Figure 29C:
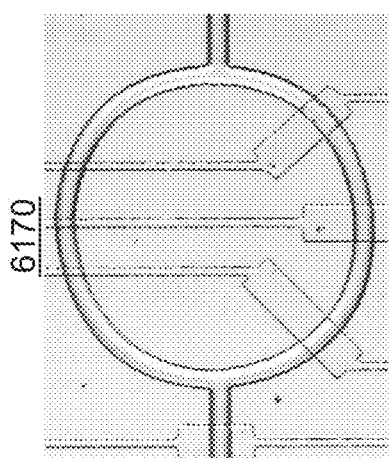
Figure 29B:
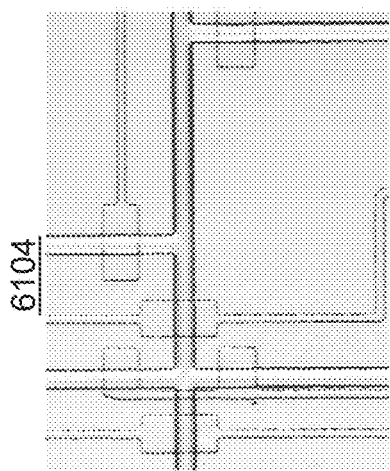

FIG. 29A shows a plan view of one embodiment of a microfluidic architecture in accordance with the present invention. Microfluidic chip 6100 comprises first flow channel 6102 leading successively into first, second, and third gated cross-flow injector structures 6104, 6106, and 6108. Gated cross-flow injectors 6104, 6106, and 6108 are defined by the intersection of first flow channel 6102 and second flow channel network 6110 comprising branches 6110a, 6110b, and 6110c. Three parallel isolations are available with different sample volumes of 1.6 nl, 1.0 nl, and 0.4 nl, for cross-flow injection structures 6104, 6106, and 6108, respectively. FIG. 29B shows an enlarged view of cross-flow injection structure 6104.

Horizontal flow control line 6112 overlaps flow channels 6102 and 6110 at the inlets and outlets to cross-flow injector structures 6104, 6106, and 6108, thereby controlling the flow of liquid into and out of these structures.

Prior to operation of the embodiment of the fluidic device shown in FIG. 29, a sample has been obtained from the environment of interest. Samples obtained from the environment may have bacterial/viral concentrations of $1 \times 10^{8-9}$ entity/ml or even higher. Such a concentration corresponds to about 1 bacterial or viral entity per picoliter (pL), with one picoliter=1000 nanoliters. If necessary, the concentration of the sample may be diluted to ensure that the maximum number of desired bacterial or viral entities are captured within a microfluidic chamber having a particular volume. Dilution may also be helpful in order to obtain desired sample properties such as viscosity or pH.

In the initial, isolation step, the sample is flowed through inlet 6102a of first flow channel 6102. Because of the previous dilution step, a limited number of viruses/cells from the sample are present in each of gated cross-flow injector structures 6104, 6106, and 6108. Horizontal control line 6112 is then actuated to trap the diluted samples within cross-flow injector structures 6104, 6106, and 6108.

In one experiment, a culture of eGFP-expressing *E. coli* was verified to reach a final cell concentration of $5.3 \pm 3.5 \times 10^8$ cells/mL. It was then diluted 1:10 in nuclease-free water and loaded into the chip. The average number of bacteria in the 0.4 nL, 1.0 nL, and 1.6 nL compartments were 27, 61, and 139, respectively, in fair agreement with the expected results of 21, 53, and 85.

While some dilution of the sample for isolation purposes may take place off-chip, a certain degree of sample dilution may also be accomplished utilizing the microfluidic structure of FIG. 29 itself. Specifically, located immediately upstream of cross-flow injector structures 6104, 6106, and 6108, are second cross-flow injector structures 6120, 6122, and 6124, respectively. Second cross-flow injector structures 6120, 122, and 6124 are defined by the intersection of third flow channel 6126 with branches 6110a-c of second flow channel network 6110.

A buffer may be located through inlet 6126a of third flow channel 6126 into cross-flow injector structures 6120, 6122, and 6124. The horizontal valve 6130 separating the pairs of cross-flow injection structures 6104/6120, 6106/6122, and 6106/6124, may then be deactivated to allow the contents of these adjacent injection structures to mix, thereby further diluting the sample.

While the above description has focused upon isolation of a particular bacterium or virus through physical containment of a diluted sample in a microfluidic chamber, other approaches could initially isolate bacteria or viruses utilizing a sorting approach. One example of a microfluidic structure useful for such sorting application is described by Fu et al, S. R. Anal. Chem. Vol. 74, pp. 2451-2457 (2002), hereby incorporated by reference for all purposes.

2. Lysis and Purification of Viral/Bacterial Nucleic Acid

In order to purify and recover nucleic acid from a particular cell or virus, the cell or virus must first be lysed to expose the contents thereof. Returning to FIG. 29A, inlet 6110d to second flow channel network 6110 is in fluid communication with three inlet flow channels.

Inlet 6110a of second flow channel network 6110 is in fluid communication with lysis chemical inlet 6132 through valve 6133. Inlet 6110a of second flow channel network 6110 is in fluid communication with wash inlet 6134 through valve 6135. Inlet 6110a of second flow channel network 6110 is in fluid communication with elution inlet 6136 through valve 6137.

During the lysis stage of operation of the microfluidic structure of FIG. 29, lysis chemistry is flowed into flow channel network 6110. The horizontal valve isolating the cross-flow injection structures are opened, and the entire sample, buffer, and lysis solution mixture is flowed into mixing structures 6170.

The combined sample/buffer/lysis solution mixture is flowed into mixer 6170 by a process of dead-ended loading, as loop exit control line 6172 remains actuated. Mixing control lines 6171a-c are then actuated to flow the mixture around the circular flow channel to accomplish mixing. FIG. 29C shows a photograph of an enlarged view of the rotary mixing structure having a volume of 5 nL.

In the experiment described above wherein an average number of bacteria of 27, 61, and 139 were loaded into the 0.4 nL, 1.0 nL, and 1.6 nL compartments, subsequent transfer of the loaded bacteria into the rotary mixer ranged from about 70% to 92%.

Figure 30B:
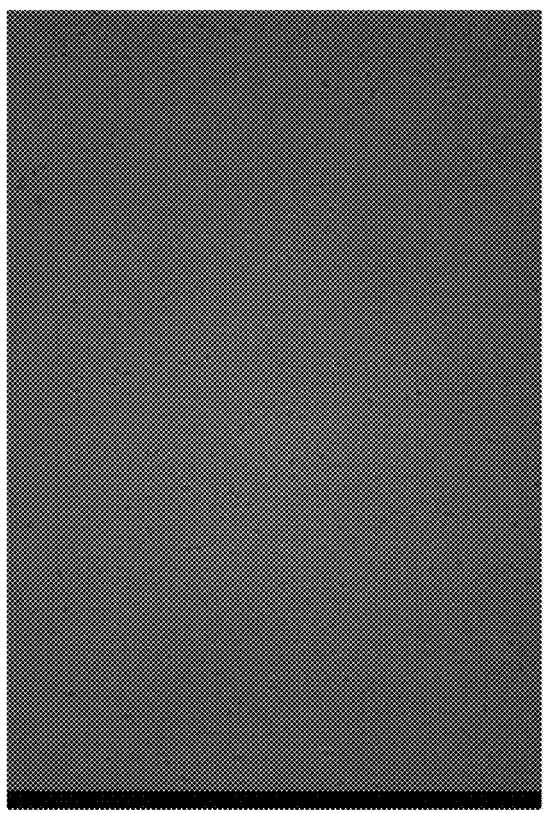
FIGS. 30A and 30B show photographs of enlarged regions of the microfluidic architecture of FIG. 29A before and after cell lysis.
Figure 30A:
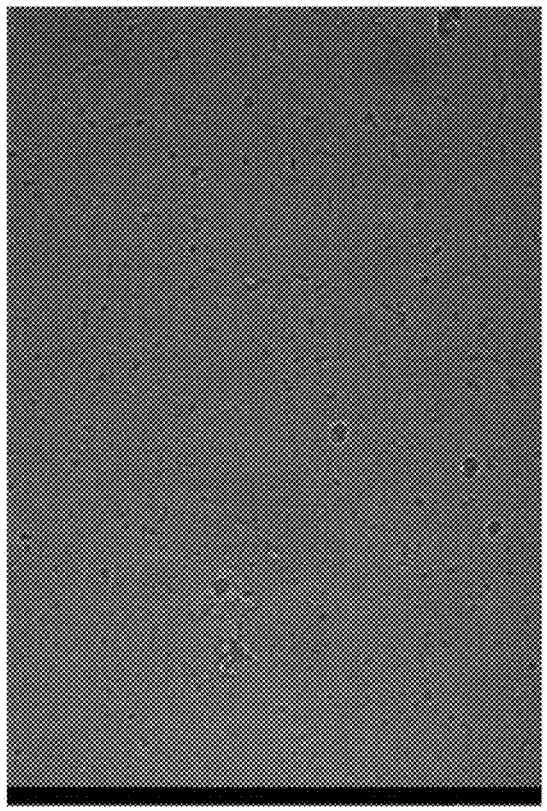

FIGS. 30A-B show photographs of a sample of *E. coli* bacteria prior to, and subsequent to, lysing, respectively. Lysing was accomplished by mixing with a lysis buffer comprising sodium hydroxide and urea. After lysis, the bacterial cells ceased active movement and fluorescent signal was lost.

After bacteria or viruses have been isolated and lysed on the chip, the next step is to purify the nucleic acids of interest. It is possible to purify genomic DNA from bacterial cells lysed on chip.

Returning again to FIG. 29A, once the combination of the sample, buffer, and lysis solution have been thoroughly mixed, wash inlet valve 6133 exit valves 6140 of mixers 6171 are opened. Wash is flowed through flow channel network 6110 and the contents thereof, including mixers 6170, the contents of which are in turn flowed through a third set of cross-flow injection structures 6171, 6172, and 6174, respectively, into waste 6180. FIG. 29D shows an enlarged view of one bead-centers cross-flow injection structure.

Cross-flow injection structures 6171, 6172 and 6174 have been loaded through fourth flow channel 6176 and reactuated valves from bead trap control line 6186 with beads coated with a substance exhibiting affinity to particular nucleic acids. Examples of such beads are DYNABEADS® available from Dynal Biotech of Oslo Norway.

Deactivation of the bead horizontal control valves defined by control line 6188 allows the fluid from the mixer to be exposed to the beads. As the lysed sample flows from the mixer through the third set of cross-flow injection structures containing the coated beads, nucleic acids in the sample adhere to the coated beads, while the remainder of the sample and wash is discarded.

Next, an elution solvent is flowed from inlet 6136 through flow channel network 6110 and through third cross-flow injection structures 6171 and 6172 and 6174 containing the beads. As a result of the presence of the flowing elution solvent, nucleic acid formerly bound to the beads is released. This eluted nucleic acid is collected in one of collection ports 6180, 6182 and 6184, and may then be amplified and/or analyzed.

Based upon the manufacturer's specified minimum capacity for each bead, each column formed by the third cross-flow injection structures of FIG. 29A was calculated to have a total capacity of 100 pg of DNA, enough to purify genomic DNA from some 20,000 bacteria.

Since elution liquid is flowed from single input 6136 to each of the third cross-flow injection structures to simultaneously elute the purified nucleic acid, it is important that each processor exhibit the same fluidic resistance. Specifically, if the channel lengths vary, then the corresponding resistance will cause unequal fluid flow in the separate processors, thus affecting the elution rates. Therefore, the overall microfluidic channel lengths for each processor were identical, with the central flow channel including a serpentine portion to add compensating flow channel length.

Figure 32A:
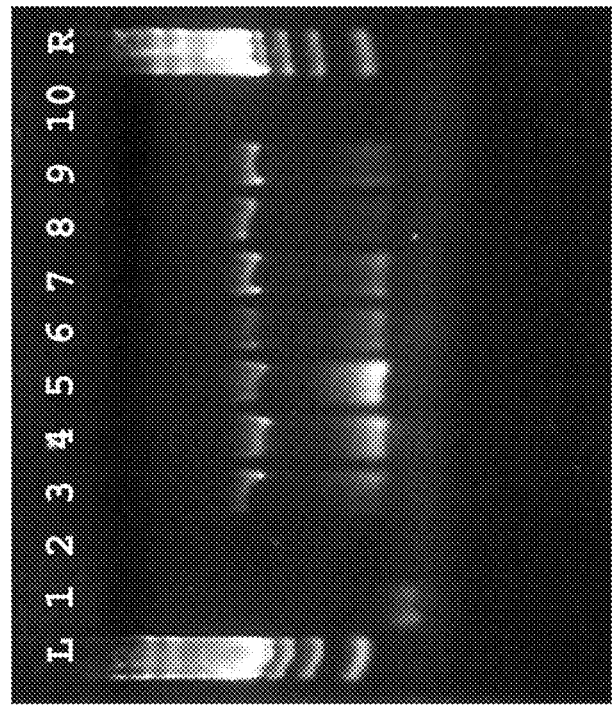
FIGS. 32A and 32B show the results of analyzing different samples of purified nucleic material utilizing the microfluidic architecture of FIG. 29A.

FIG. 32A shows the results of electrophoresis of genomic DNA purified from a chamber containing less than about 280 individual *E. coli* bacterial cells. Bacterial genomic DNA was recovered out of the chip by using elution buffer. The DNA in the elution buffer was amplified with ppdD primer sets by using conventional PCR method with 50 ul working volume.

The target nucleic acid purified was a 461 bp ppdD (prepilin peptidase dependent protein D precursor) gene from *E. coli* genome DNA. Genomic DNA captured on the surface of polystyrene magnetic beads were recovered by using elution buffer and amplified by PCR reaction. The samples were run on 1.2% agarose gel in TBE (Tris-Borate-EDTA) buffer.

Gel lanes were as follows: L, R-100 bp DNA ladder; lanes 1, 4 and 7—isolation of genomic DNA from 1.6 nL *E. coli* culture broth corresponding cell number less than 1120; lanes 2, 5 and 8—isolation of genomic DNA from 1.0 nL of *E. coli* culture broth corresponding cell number less than 700; lanes 3, 5 and 9—isolation of genomic DNA from 0.4 nL of *E. coli* culture broth with cell numbers less than 280. Lane 10; is a negative control.

Figure 32B:
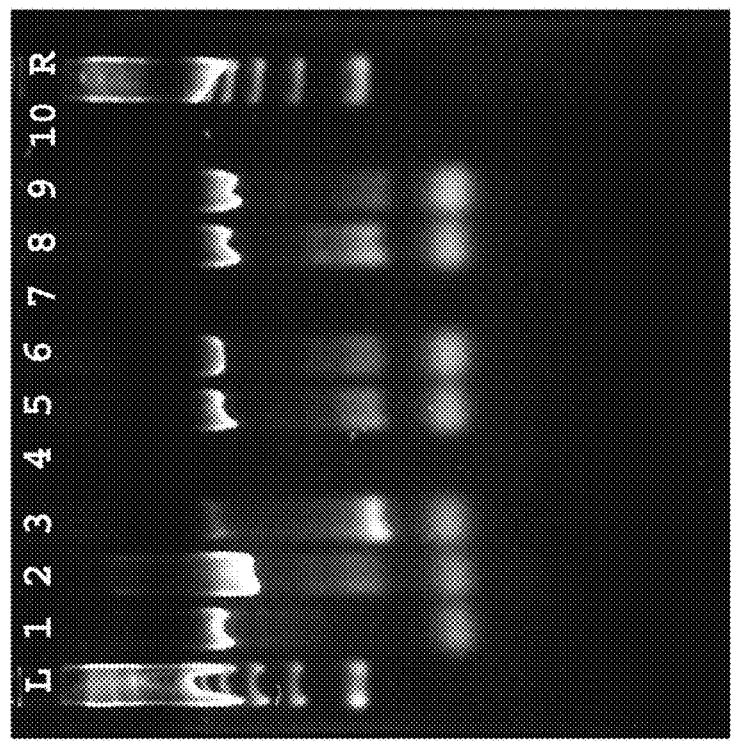

FIG. 32B shows the results of electrophoresis analysis of genomic DNA purified from a chamber containing less than 28 individual *E. coli* bacterial cells. Bacterial genomic DNA was recovered out of the chip by using elution buffer.

The DNA in the elution buffer was amplified with ppdD gene primer sets by using a conventional PCR machine with 50 ul working volume. Again, the target purified nucleic acid is 461 bp ppdD (prepilin peptidase dependent protein D precursor) gene from *E. coli* genome DNA.

Gel lanes as follows: L, R-100 bp DNA ladder; lanes 1, 4 and 7—isolation of genomic DNA from 1.6 nL of 10-fold diluted *E. coli* culture broth corresponding cell number less than 112; lanes 2, 5 and 8—isolation of genomic DNA from 1.0 nL of ten-fold diluted *E. coli* culture broth corresponding cell number less than 70; lanes 3, 5 and 9-isolation of genomic DNA from 0.4 nL of ten-fold diluted *E. coli* culture broth corresponding cell number less than 28. Lane 10 is a negative control.

Figure 31A:
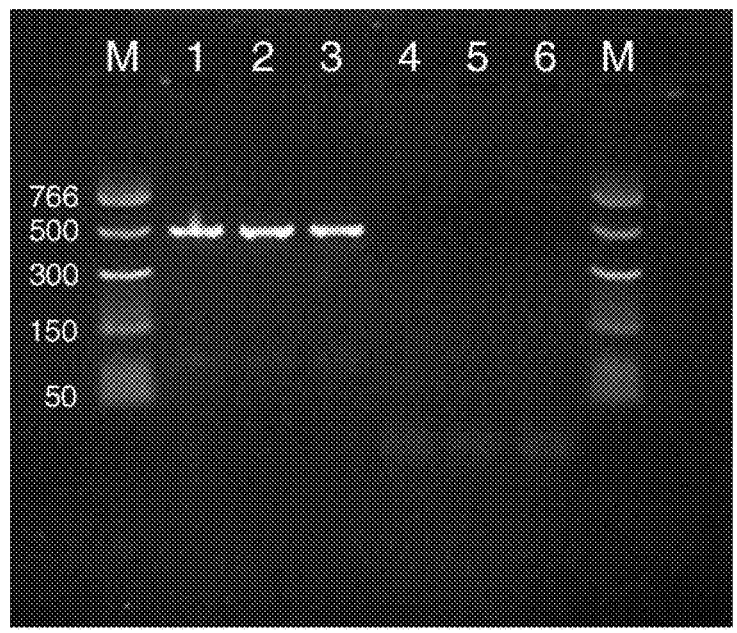
FIGS. 31A and 31B show electrophoresis of nucleic acid samples purified in accordance with embodiments of the present invention.
Figure 31B:
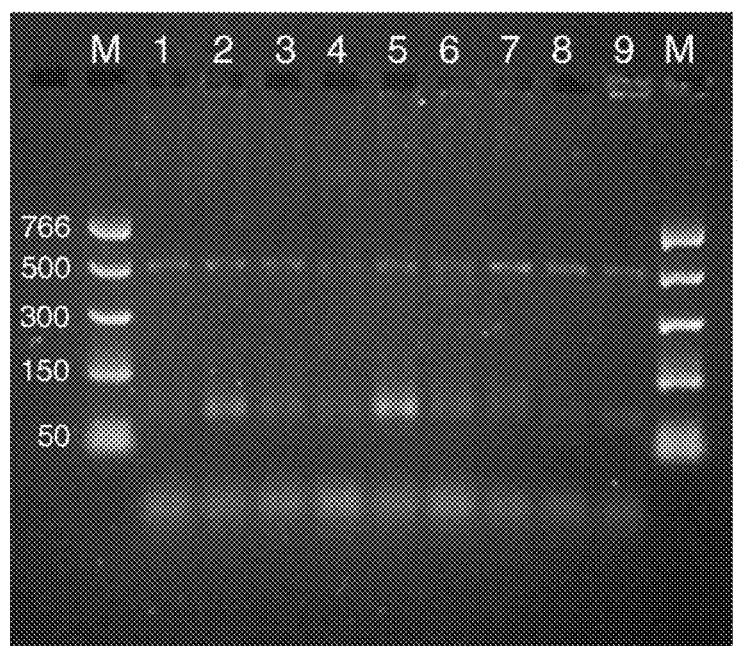

FIGS. 31A-B show other electrophoresis results for nucleic acids purified in accordance with embodiments of the present invention. Specifically, FIGS. 31A-B verify successful recovery of purified *E. coli* genomic DNA from the microfluidic architecture of FIG. 29A The eluted samples were removed from the chip and amplified with PCR. The amplicons were run on a 2.0% agarose gel in 0.5% TBE (Tris-Borate-EDTA) buffer. The target DNA is a 461 bp fragment of the *E. coli* ppdD (prepilin peptidase dependent protein D precursor) gene.

FIG. 31A shows isolation of genomic DNA with undiluted *E. coli* culture, with the following gel lanes: M-PCR marker; lane 1—isolation of genomic DNA from 1.6 nL of culture with a corresponding cell number of approximately 1,120; lane 2—a 1.0 nL sample with a corresponding cell number of approximately 700; and lane 3—a 0.4 nL sample with cell numbers of approximately 280. Lanes 1-3 of FIG. 31A show strong isolated bands approximately 500 base pairs in length, revealing purification of the genomic DNA.

Lanes 4, 5, and 6 are negative controls for genomic DNA isolation in which purified water was used instead of cell culture sample and all the other conditions were the same as lanes 1, 2, and 3. No amplified signal was present in any of these control cases.

FIG. 31B shows isolation of genomic DNA from a 1:10 dilution of cell culture. Lanes 1, 2, 3, lanes 4, 5, 6, and lanes 7, 8, 9 are the results from three different chips, respectively. Gel lanes as follows: M-PCR marker; Lanes 1, 4, and 7—isolation of genomic DNA from an average of 112 bacterial cells; Lanes 2, 5, and 8—isolation of genomic DNA from an average of 70 bacterial cells; Lanes 3, 6 and 9—isolation of genomic DNA from an average of 28 bacterial cells.

Since the amounts of purified DNA were too small to measure by conventional means, PCR amplification of the prelipin peptidase dependent protein (ppdD) gene was used for verification of successful recovery. The results of FIGS. 31A-B show that it is possible to reduce the number of cells needed for DNA isolation, and thereby increase the sensitivity of this process by 2,000-20,000 times over conventional methods.

The nucleic acid purification microfluidic architecture shown in FIGS. 29A-D demonstrates the parallelization strategy employed. Process steps take place along a roughly linear channel, allowing parallelization of the process in the orthogonal direction. This geometry allows a single reagent fill line to dispense reagents simultaneously to all of the parallel processes.

The microfluidic architecture shown in FIGS. 29A-D was fabricated by multilayer soft lithography. Mask designs were created with the CAD program FluidArchitect (Fluidigm, South San Francisco, Calif.) and transferred to high-resolution transparency masks (3,389 dpi). The dimensions of the fluidic channels are 100 µm in width and 10 µm in depth, while the valve actuation channels are typically 200 µm in width and 15 µm in depth. The chip included within 20×20 mm space, 13 fluidic access vias, 54 valves and 14 actuation vias that allow microfluidic flow and control.

Mask molds for the fluidic channels were made by spin-coating positive photoresist (Shipley SJR 5740) on a silicon wafer with 2,000 rpm for 1 min, followed by mask exposure and development. These mold channels are rounded at 135° C. for 15 min to create a geometry that allows full valve closure.

Another mold for the actuation layer is made by spinning photoresist on a separate wafer at 1,600 rpm for 1 min with a resulting height is 13 µm, followed by mask exposure and development. The devices were fabricated by bonding together two layers of two-part cure silicone (GE Silicone RTV615) cast from the photoresist molds.

The bottom layer of the device, containing the flow channels, is spin coated with 20:1 part A:B RTV615 at 2,400 rpm for 1 min and the resulting silicone layer is an 11 µm thick film. The top layer of the device, containing the actuation channels, is cast as a thick layer (5 mm thick) with 5:1 part A:B RTV615 using a separate mold.

The two layers are initially cured for 30 min at 80° C. Actuation channel interconnect holes are then punched through the thick layer with a 20 gauge luer stub, after which it is sealed, channel side down, on the thin layer, after aligning the respective channel networks with an optical microscope.

Bonding between the assembled layers is accomplished by curing the assembled devices for at 80° C. for more than 90 min, followed by punching the fluidic channel interconnects. The resulting devices are cut to size and mounted on RCA cleaned cover slips (No. 1, 24 mm×50 mm), followed by incubation at 80° C. overnight to promote adhesion.

The chip containing the microfluidic architecture is mounted on an inverted microscope (Nikon Eclipse TE2000-S). Fluorescence excitation was provided by a mercury lamp (100W). A FITC filter set (Ex465-495, DM 505, BA 515-555) was used and the image was recorded by using a PC controlled color digital camera (Sony DFW-V500).

Each actuation line on the chip was connected with a stainless steel pin (New England Small Tube, Litchfield, N.H.) and polyethylene tubing to an external solenoid valve controlled by a digital data I/O card (CCA, PPC1-DIO32HS; National Instruments, Austin, Tex.). Regulated external pressure was provided to the normally closed port, allowing the control channel to be pressurized or vented to atmosphere by switching the miniature valve.

The fluidic vias for the introduction and collection of sample and buffer were connected to an external pressure source through polypropylene tips (Multiplex tips, Sorenson BioScience, Inc., West Salt Lake City, Utah). The typical pressure for driving liquid inside the chip is 0.5 to 2.0 psi (1 psi=6.89 kPa).

After the microfluidic chip was mounted on an optical microscope stage and the control channels are connected to external pneumatic control systems, microbeads (Dynabeads® DNA DIRECT™ universal, Dynal ASA, Oslo, Norway) with DNA binding capacity are loaded through the 'bead in' port in the upper right part of FIG. 29A. For this operation, valve 10 'loop exit control' and valve 12 'bead trap control' are closed. The beads are positioned just before valve 12 by controlling the valves 6 and 12. The pressure control for valve 12 is lower than the pressure for the other valve controls, resulting in a partially closed valve that allows buffer to pass through while the beads accumulate into a column.

One µL of each of the buffer solutions (lysis buffer (Xtra Amp®, lysis buffer series 1, Xtrana, Inc., Ventura, Calif.), wash buffer (Xtra Amp®, wash buffer series 1) and elution buffer (Tris-EDTA buffer, pH 7.8)) are loaded through the 'lysis in', 'wash in' and 'elute in' ports, respectively.

*E. coli* (BL21-2$^+$) expressing eGFP were grown at 37° C. for 12 h in Luria-Bertani (LB) liquid medium containing ampicillin with 40 µg/ml of concentration. After the DNA purification and recovery from the chip, we attempted to amplify a gene, ppdD (prepilin peptidase dependent protein D precursor, 461 bp), DNA contained in *E. coli* bacterial cells with a conventional PCR method.

Thermal cycling conditions were as follows: Initial denaturing: 2 min at 95°; DNA denaturing: 30 sec at 95°; Primer annealing: 30 sec at 60°; dNTP polymerizing: 2 min and 30 sec at 72°; Repeat steps from denaturing to polymerizing 30 times; Final extension: 10 min at 72°.

The primer set for ppdD gene is 5'-GGTGGTTATTG-GCATCATTGC-3'(SEQ ID NO:1) for forward and 5'-GT-TATCCCAACCCGGTGTCA-3' (SEQ ID NO:2) for reverse. The PCR cocktail is 5 µL of 10× reaction buffer, 1 µL of dNTP mix with the final concentration of 10 mM, each 1 µt of forward and reverse primers, 0.5 µt of Taq Polymerase 5 U/µL, and template and water to make 50 µL of total reaction volume.

3. Lysis/Purification of Non-Bacterial Nucleic Acid

The above-referenced discussion relates to purification of nucleic acids obtained from the lysis of bacterial cells. However, embodiments in accordance with the present invention are not limited to purification of this type of nucleic acid. Other types of nucleic acid, including but not limited to messenger RNA (mRNA) from eukaryotic cells, may be isolated and purified in accordance with embodiments of the present invention.

Isolation of mRNA, either to measure gene expression or to construct a cDNA library, is a cornerstone of modern day molecular biology. There are numerous techniques for mRNA isolation, but nearly all require hundreds to thousands of cells as a starting material. Yet there are many situations where it would be useful to know the gene expression profile, or to develop a cDNA library, from a single cell.

Some primary cell types are very rare, like stem cells, and expansion in culture to acquire more cells changes the expression profile of the cell. Attempting to isolate a number of primary cells from an animal or patient invariably results in a mixture of cell types because it is not possible to precisely identify, and therefore isolate in a pure form, any single cell type. Furthermore, there has recently been a renewed interest in epigenetic variations in gene expression between cells that are nominally identical genotypes, to understand how these variations might play a role in development and other phenotypic differentiation processes.

There are well established methods for measuring expression of a few genes from a single cell, but these require a priori choice of a small number of targets. This limitation has been somewhat alleviated by recent progress in amplifying mRNA from a single cell for use in more highly parallel microarrays. These methods allow parallel analysis of a larger number of targets, but the mRNA amplification process inevitably introduces some degree of distortion, and the microarrays themselves require choice of a finite set of possible transcripts.

Construction of a cDNA library from a single cell has not yet been demonstrated, but could provide a powerful tool to probe expression without a priori assumptions about which genes are being probed. Thus far, the minimum number of cells needed for cDNA library construction is 1,000, with 10,000 being more usual, and the virtues of using microfluidics to construct such a library have been recognized.

Figure 37A:
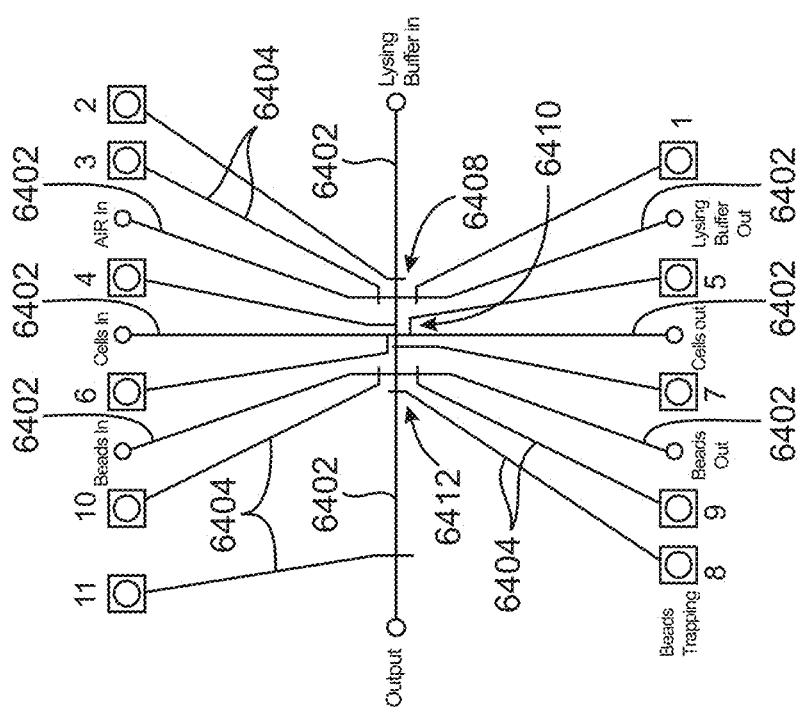
FIG. 37A is a plan view of an alternative microfluidic architecture in accordance with the present invention

Accordingly, FIG. 37A shows an embodiment of a microfluidic architecture 6400 in accordance with the present invention that is useful for isolation and purification of nucleic acid from other than bacteria or viruses. Lines 6402 represent the 100 µm wide fluidic channels, and lines 6404 are the 100 µm wide valve actuation channels. The fluidic ports are named; the actuation ports are numbered 1 to 11.

Lysing buffer chamber 6408 comprises the channel space delineated by valves 1, 2, 3 and 4. Cell chamber 6410 comprises the channel space delineated by valves 4, 5, 6 and 7. Beads chamber 6412 comprises the channel space delineated by valves 7, 8, 9, and 10.

Nucleic acid purification chip 6400 comprises different functional units integrated into a single structure. The processing architecture of the chip is horizontal, with reagents loaded vertically, a scheme which can be generalized to implement a large class of sequential, batch processed reactions.

The first functional unit of architecture 6400 comprises chamber 6410 that can be loaded with a variable number of cells. The precise number of such loaded cells can be controlled by the concentration of cells in the loaded solution. In this study, samples were diluted to trap between 1 and 100 cells.

Adjoining the cell chamber 6410 is the lysis buffer chamber 6408, which can be loaded with a fixed amount of a solution of chaotropic salt. Valve 4 separating chambers 6408 and 6410 can be opened to allow diffusion of the lysis buffer into the cells. The total volume in which the cells are lysed (between valves 1, 2, 3, 5, 6 and 7) is about 20 nL.

Figure 37B:
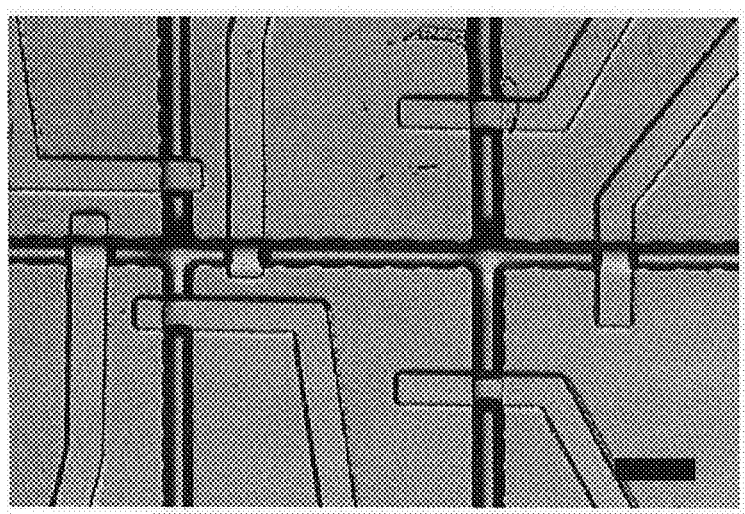
FIG. 37B is a photograph showing an enlargement of the adjacent lysis and cell chambers of FIG. 37A.

FIG. 37B is a photograph showing enlargement of the adjacent lysing buffer and cell chambers of FIG. 37A. The actuation channels forming valves 1 to 7 are filled with an aqueous solution of a food dye, orange G. The scale bar is 200 microns.

The next functional unit of the chip is designed to create a packed column of oligo dT derivatized paramagnetic beads (Dynabeads Oligo(dT)25) through which the cell lysate can be flushed. In order to trap a precise amount of beads, a microfluidic valve whose opening could be controlled precisely by a pressure regulator, was used.

Valve 8 is left slightly open so that a regulated fluid flow can pass through, but the large (2.8 gm) beads are trapped. All the other valves are on off valves, controlled by individual pressure sources. Those pressure sources are actuated by an NI DAQ card (National Instrument) and a graphic interface developed under Labview 6.0 (Fluidigm Corp). At the end of each run, beads are collected from the chip and assayed for the presence of mRNA with benchtop RT PCR.

Figure 37C:
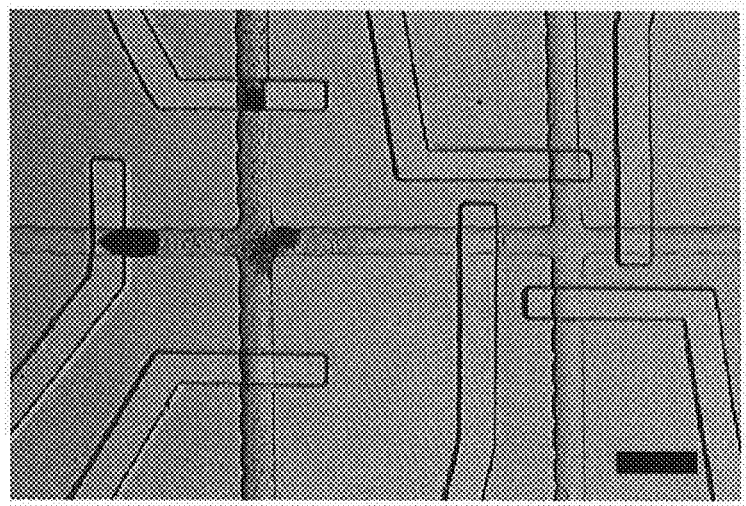
FIG. 37C is a photograph showing an enlargement of the adjacent bead and cell chambers of FIG. 37A.

FIG. 37C is a photograph showing an enlargement of the adjacent bead and cell chambers of FIG. 37A. A column of 2.1 μm diameter paramagnetic beads covered with oligo dT is being built against a partially closed microfluidic valve 8. The scale bar is again 200 microns.

Specific operation of the microfluidic chip 6400 may be summarized as follows. All the valve actuation lines were filled with fluid (a concentrated aqueous solution of Orange G) in order to avoid bubble formation in the fluidic channels. The membrane separating the fluidic channel and the control line is very thin (less than 5 microns) and permeable to air. Each control line is connected to its pressure source.

The working pressure at which all pressure sources were set was 2 psi above the actuation pressure of the valves, thus allowing a 1 psi pressure on the fluidic channels. The working pressure was different from one chip to another due to small variations in the membrane thickness, but typically between 8 and 15 psi. All the valves were closed before loading the reagents.

The reagents were delivered through polyethylene tubing, which was connected to the chip using 23 gauge stainless steel pins (New England Small Tubes, Litchfield, N.H.). The other end of the tubing was connected to a common pressure source for all the fluidic channel inputs (1 psi). The chip was loaded with 10 of cell solution, 20 μL of al Lysis buffer, and 5 μL of beads solution. The original Dynal beads were resuspended in Dynal Lysis buffer and reconcentrated to 5× concentration.

The lysis buffer was first loaded on the chip by opening valves 1 and 2. Once the lysis buffer flowed through the Lysing Buffer Out channel, valve 1 was closed. The lysis buffer chamber was dead end filled by pushing the air into the gas permeable chip. Valve 2 was then closed.

Cells of the sample were prepared as follows. Freshly harvested NIH 3T3 cells were used for each experiment. NIH 3T3 cells were grown to near confluency on 100 mm tissue culture plates. The cells were rinsed with 1×PBS and then trypsinized. The trypsinized cells were resuspended in 1×PBS in order to adjust the final cell concentration to between 106/mL and 107/mL.

The cells were loaded by opening valves 5 and 6. The cell suspension flowed through the cell chamber, and valve 5 was closed. Valve 5 could be opened and closed repeatedly until a suitable number of cells were trapped in the cell chamber. The number of cells trapped in the chamber could also be influenced by changing the cell suspension concentration. Typically, 1 to 100 cells could be trapped and lysed on the chip.

Valve 6 was kept open until the remaining air in the cell chamber was pushed out. Valve 6 was then closed.

The bead suspension was loaded by opening valves 9 and 10. Once the bead suspension flowed through the beads chamber, valve 9 was closed and the chamber was dead end-filled by pushing the remaining air into the gas permeable chip. Valves 8 and 11 were then opened and pressure on valve 8 was slowly increased using the pressure regulator until the 2.1 pm diameter beads began to stack up against the partially closed valve. Once the stack was sufficiently long to reach the Beads In channel, valve 10 was closed.

Figure 37D:
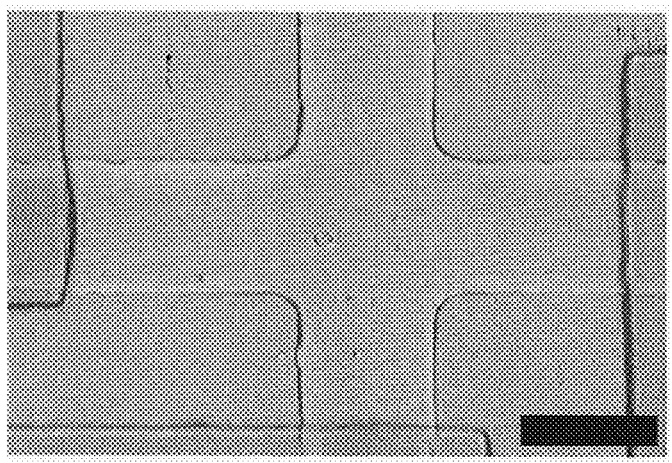
FIGS. 37D to 37F show photographs of an enlarged portion of the cell chamber before, during, and after diffusive mixing of lysis chemistry, respectively.
Figure 37E:
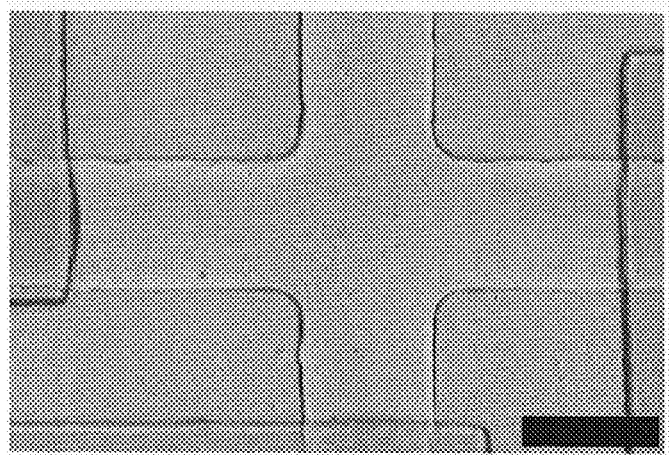
Figure 37F:
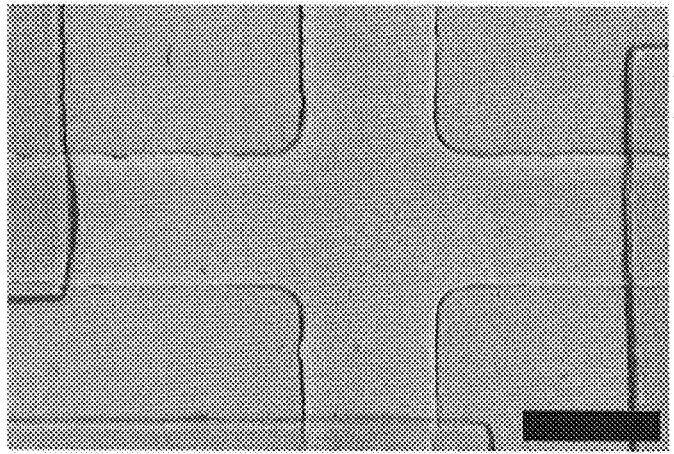

Valve 4 was opened, thereby allowing the lysis buffer to diffuse into the cell chamber. As lysis buffer reached an individual cell, the cell would immediately lyse, and then gradually disintegrate. FIG. 37D shows a photograph of an enlarged portion of the cell chamber after initial loading. FIG. 37E shows a photograph of an enlarged portion of the cell chamber after five minutes of diffusion of lysis chemical, as the membrane begins to disintegrate as the cell is lysed. FIG. 37F shows a photograph of an enlarged portion of the cell chamber after ten minutes of diffusion, as the cell has completely disintegrated. The scale bars in FIGS. 37D-F are 100 microns.

The cell lysate was flushed out of the "cell chamber" by opening valves 3, 4, 7 and 11. The lysate was allowed to flow through the stack of beads at a controlled speed (typically 100 μm/s) that could be adjusted by changing the pressure on the Air In channel. The poly A containing mRNA hybridized to the oligo dT on the beads and remained on the beads while the majority of the cell debris washed on out of the chip. The air/fluid interface stops at the stack of beads due to surface tension.

Valve 3 was then closed, valve 2 was opened, and lysis buffer was flushed through the beads to wash them free of as much cellular debris as possible. Valve 2 was then closed A short tubing was connected to the output port of the chip and placed in a 0.1 mL PCR tube. Valves 2 and 8 were opened and the beads were flushed with lysis buffer into the PCR tube. A magnet was used to draw out any beads remaining in the outflow channel. The beads were centrifuged, and then resuspended in 100 μL of fresh lysis buffer. RNase Inhibitor (1 μL) was added. The tube was vortexed and the mRNA was either analyzed immediately, or the tube was stored frozen at 80° C.

In a typical experiment, several chips were used to obtain beads carrying mRNA from one or more cells. Reverse transcription and amplification was carried out directly on the beads using the Qiagen OneStep RT PCR kit, followed by gel electrophoresis of the products. Primers were used to identify two types of mRNA: the high abundance β actin transcript and the moderate abundance zinc finger ozf transcript.

Figure 38:
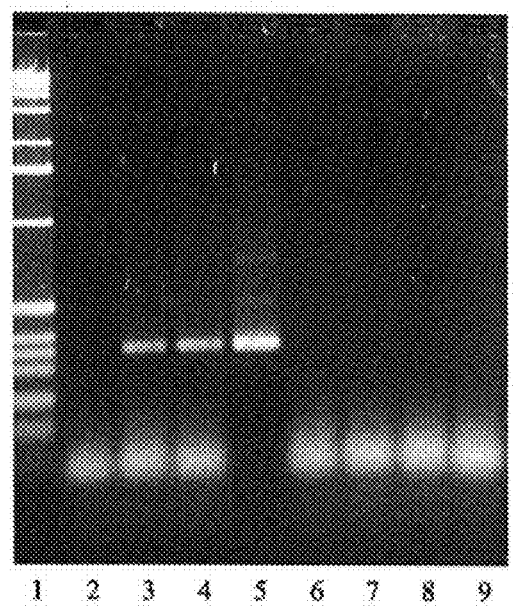
FIG. 38 shows electrophoresis results for a series of experiments performed in order to demonstrate single cell sensitivity together with negative controls.

FIG. 38 shows electrophoresis results for a series of experiments performed in order to demonstrate single cell sensitivity together with negative controls. The RT PCR products were analyzed on a 2% agarose gel loaded with 5% of the reaction; the amplified gene is β actin.

Gel lanes are as follows: lane 1: lkb ladder; lane 2: PBS, no cells (on the chip); lane 3: 1 cell (on the chip); lane 4: 9 cells (on the chip); lane 5: 200 uL supernatant from 1 day old cells +5 μL of beads (in a test tube); lane 6: 200 μL lysing buffer+5 μL of beads (in a test tube); lane 7: cells loaded on the chip but none trapped in the chamber (on the chip); lane 8: 200 μL, DI water+5 μL beads (in a test tube); lane 9: PCR reagents only.

FIG. 38 shows successful mRNA isolation from a single NIH 3T3 cell in lane 3. A positive control, supernatant from lysed NIH 3T3 cells, is shown in lane 5, and various negative controls are shown: All the negative controls show no band in the (3 actin DNA region, while the positive control demonstrates a strong band.

When the intensity of a band is normalized by the number of beads in the column, a monotonically increasing relationship is found between intensity and cell number for the highly abundant O actin mRNA, down to the single cell level. Specifically, a second series of experiments was performed in order to test the chips with variable numbers of cells and both high and medium copy number transcripts.

Figure 39:
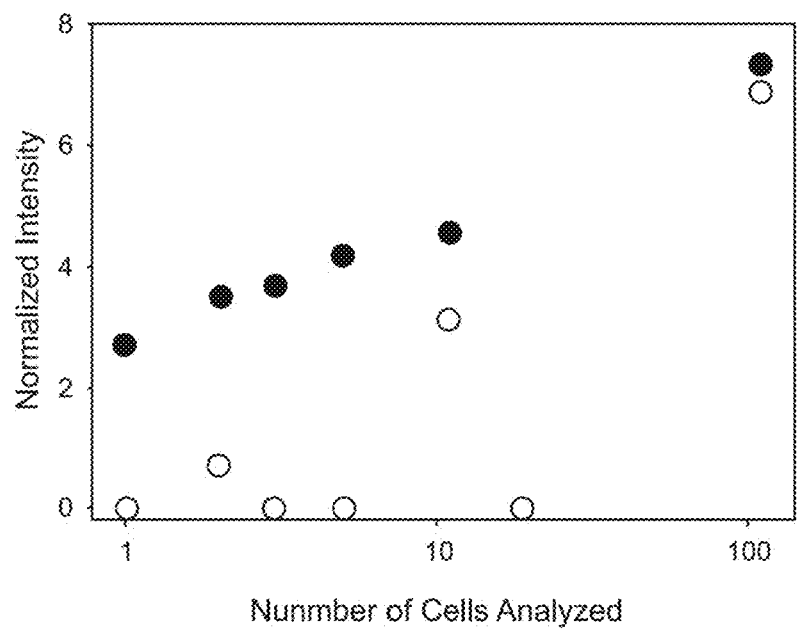
FIG. 39 plots RT PCR products for both β-actin and ozf analyzed on a 2% agarose gel.

The RT PCR products for both (β-actin and ozf were analyzed on a 2% agarose gel, whose bands were quantitated, normalized, and plotted in FIG. 39. Zero values indicate the absence of a detectable band in the gel; the experiment with 19 cells failed for both transcripts, possibly because of RNAase contamination or chip failure.

For high abundance actin mRNA, detection is down to the single cell level. For the moderately abundant zinc finger ozf mRNA, signal could be detected from as little as two cells, but the typical sensitivity is somewhere between 2 and 10 cells. Thus, the sensitivity of this first generation chip is established Despite the fact that the RT PCR is not a linear amplification process, these results are semi quantitative in the sense that they are consistent with the cell number. If the band intensities are not normalized by the size of the column, then the results are not monotonic and do not obey any obvious functional relationship.

This result is interpreted as an indication that the kinetics of mRNA binding to the beads were not fully equilibrated, and that the sensitivity of future devices can be improved by increasing the interaction time of the lysate with the column.

An intriguing possible future application for microfluidic mRNA preparation is as a tool to generate subtractive libraries from single cells (or more accurately, pairs of single cells). Such a procedure would be valuable in eliminating commonly expressed transcripts while enriching for differentially expressed transcripts, and is not feasible for small numbers of cells using conventional tools.

In a standard preparation, mRNA isolated from roughly $1 \times 10^6$ cells is processed in a volume of order 10 μL. The same mRNA concentration would be attained (assuming no adhering of mRNA to vessel walls) if the mRNA from 1 cell were contained in a 10 pL volume. While such volumes are larger than those used in the present study, they are readily attainable with current microfluidic technology, and valves with an order of magnitude smaller displacement volume have already been demonstrated.

One difference between the microfluidic architecture of FIG. 29A utilized for isolation and purification of bacterial nucleic acid, and the microfluidic architecture of FIG. 37A utilized for isolation and purification of non-bacterial nucleic acid, is the presence of an active mixing structure to enhance mixing of the lysing chemical and the sample. In the case of viruses or bacteria, such active mixing is useful to rapidly disrupt the resilient viral sheath or cell wall structures protecting the virus or bacteria. However, entities other than bacteria or viruses (such as mammalian cells), lack these protective structures, and may therefore experience lysis under less stringent conditions, for example mere diffusion across a microfluidic free interface.

Another difference between the microfluidic architecture of FIG. 29A utilized for isolation and purification of bacterial nucleic acid, and the microfluidic architecture of FIG. 37A utilized for isolation and characterization of non-bacterial nucleic acid, is the use of parallel flow structures controlled by common control lines. However, this technique can also be employed in the isolation and purification non-bacterial nucleic acid, as illustrated in connection with FIG. 40.

Figure 40:
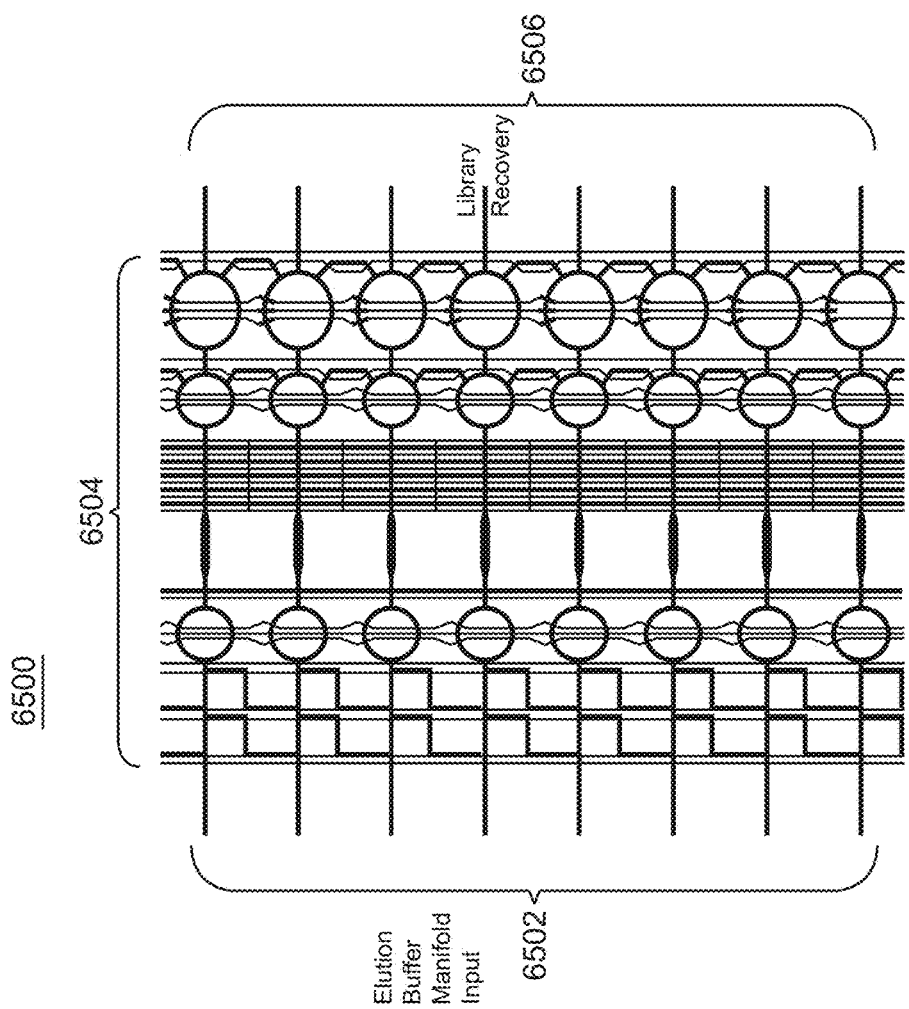
FIG. 40 shows a plan view of an alternative embodiment of a microfluidic architecture in accordance with the present invention.

FIG. 40 shows a plan view of an alternative embodiment of a microfluidic architecture in accordance with the present invention. Microfluidic architecture 6500 allows eight simultaneous cDNA libraries to be created by implementing the SMART cDNA library kit in chip format.

Left column 6502 of inputs can be connected to an elution buffer manifold. Top row 6504 contains control lines and reagent inputs; with the ten reagent inputs comprising, in order, stem cells, lysis buffer, oligo dT beads, primers, reverse transcriptase, PCR reagents, proteinase K, Swi I, plasmids, and competent bacteria. The top row flow and control inlets would fan out to allow access to space for macroscopic connections.

The parallel cDNA microfluidic architecture of FIG. 40 uses both diffusive and active rotary mixing, depending on the time sensitivity of the step. The eight separate libraries may be recovered from outputs 6506.

Chip design 6500 combines cell lysis, mRNA purification, and a chip based implementation of a commercial cDNA library kit. Temperature may be controlled with a thermo electric stage mounted to the microscope, and reagents will be flushed into the vertical channels as needed, thus preventing aging, denaturation or inappropriate temperatures during earlier stages of the experiment.

Chip 6500 is designed to make a library of cDNA clones from a small number (from 1 to 1,000) of cells. It uses the basic microfluidic techniques already described to isolate, lyse, and purify mRNA from cells, which will then be cloned into competent *E. coli* cells using the Creator SMART cDNA Library Construction kit from Clontech. This kit can readily be translated to chip format since it is a one tube, one step reaction.

The bacteria will be recovered from the chip using the methods developed for the cell sorter and MHTSC chips. Since the bacteria grow exponentially, one can easily grow enough material to interrogate the library using conventional genomic techniques: DNA microarrays and high throughput EST sequencing being two examples. The chip may be validated using a cell line and comparing clone frequency to frequencies measured by high throughput EST sequencing.

To evaluate the cDNA library constructed from a small number of cells on the chip, the following steps may be followed. First, one large aliquot of cells ($1 \times 10^8$) will be used to isolate mRNA and check the integrity on a gel. A small aliquot (1 to 1000 cells) of the same cells will be trapped in the chip and the mRNA isolated and checked on a gel.

Conventional cDNA library construction will then be performed with the minimum of 1 ug mRNA; at the same time, a cDNA library will be constructed on a chip. Initially, conventionally isolated mRNA will be used to verify that a cDNA library can be made on a chip. Later, the first stage chip (cells to mRNA) will be combined with the second part (mRNA to cDNA library).

Next, random clones (12) from each library will be characterized for the average insertion size. One hundred individual clones from each library will then be selected for sequence analysis and to establish a profile for each cDNA library.

The redundant cDNA will be mixed and used to make a probe, and hybridization will be performed to the other 9900 colonies. The negative colonies will next be sequenced. This procedure should greatly reduce the number of colonies that need to be sequenced, since the redundant colonies will be eliminated.

Bioinformatic analysis will then be performed to compare the gene expression profile between the conventional cDNA library construction and the chip based cDNA library construction.

Library insert sizes will also be characterized. Obtaining full length transcripts will not be crucial for the initial version of the chip, as bioinformatic tools for the analysis of the human genome will be at a mature enough state that most gaps will be able to be filled in by computer. However, later versions of the chip for other applications can be optimized for full length transcripts.

Isolation and purification of mRNA utilizing microfluidic techniques in accordance with embodiments of the present invention may find use in any number of applications. One such application is the construction of cDNA libraries. Another application is mRNA isolation for gene expression analysis, for example utilizing a microarray chip as is well known to one of ordinary skill in the art.

While the microfluidic architectures described above are employed in the ligation and transformation of purified nucleic acids, the mixing and flow schemes may be generalized to encompass other useful functionalities. For example, the mixing structures utilized in ligation or transformation can in turn be in fluid communication with other mixing structures used to prepare specific materials from chemical kits. Examples of materials prepared by such chemical kits include but are not limited to specific plasmids for ligation, and specific enzymes utilized in constructing cDNA libraries, as well known to one of ordinary skill in the art.

The above sections have described the isolation within a microfluidic chamber, of individual or subsets of elements of a heterogeneous sample. Embodiments in accordance with the present invention are not limited to isolation of any particular number of relevant biological entities within a particular microfluidic chamber. Embodiments of microfluidic architectures and methods in accordance with the present invention could be designed to isolate 1, 2, 3, 4, 5, 6, 7, 8, 9, 10, 15, 20, 25, 30, 35, 40, 45, 50, 60, 70, 80, 90, 100, 200, 300, 400, 500, 1000, 5,000, 10000, 50,000, 100,000 or an even greater number of biological entities within a single microfluidic chamber.

4. Amplification of Nucleic Acid

Polymerase chain reaction (PCR) has become one of the most ubiquitous tools in molecular biology, and thus one of the most important biochemical reactions to be implemented in a microfluidic device is the ability to amplify nucleic acids. Liu et al., "A Nanoliter Rotary Device for PCR", Electrophoresis, Vol. 23, p. 1531 (2002), incorporated by reference herein for all purposes, have previously created a microfluidic architecture for performing PCR.

Figure 34:
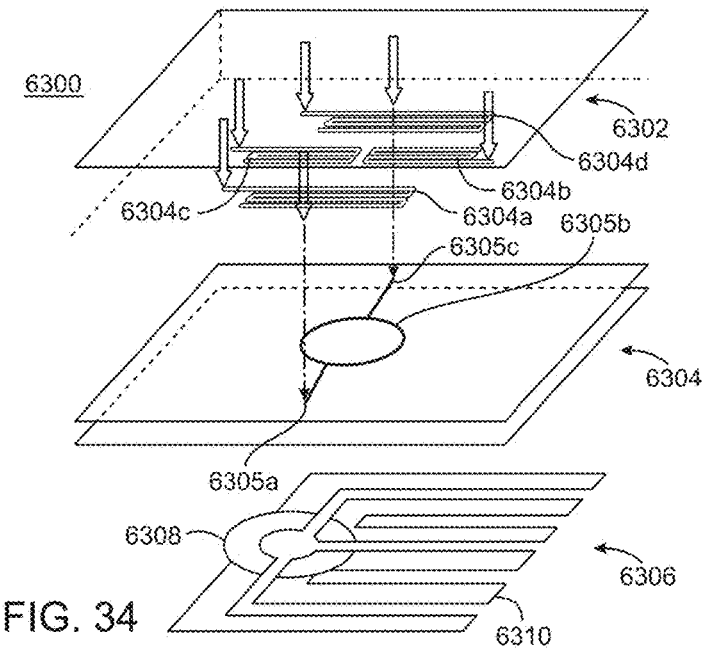
FIG. 34 shows an exploded view of a microfluidic structure for performing PCR.

FIG. 34 shows a schematic diagram of one embodiment of a microfluidic structure 6300 in accordance with the present invention for performing PCR. Top layer 6302 includes control channels 6304a-d for controlling the pumps and valves. Middle layer 6304 defines the inlet 6305a, rotary 6305b, and outlet 6305c fluid flow channels. Bottom layer 6306 includes integrated heater structures 6308 and electrical leads 6310 in electrical communication therewith.

The loop in the fluid layer forms a rotary pump, by which the PCR reagents can be transported over regions of different temperatures. The temperatures are set by tungsten heaters evaporated onto glass, which become the bottom substrate of the nanofluidic chip. The total volume of the PCR reaction was 12 nL.

Figure 35:
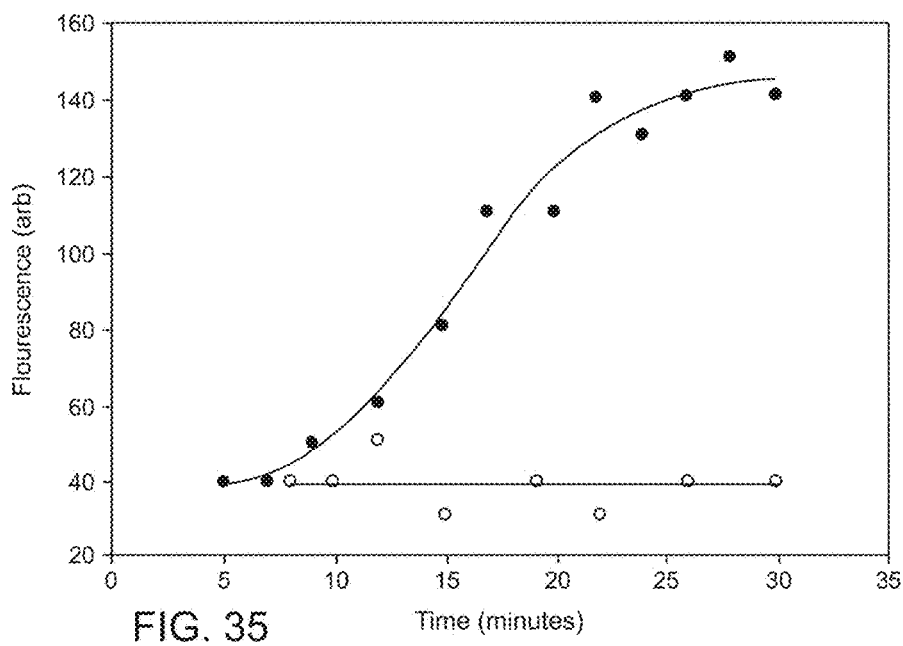
FIG. 35 plots fluorescence versus time for nucleic acids amplified by PCR utilizing the microfluidic structure shown in FIG. 34.

FIG. 35 shows results of Taqman PCR assay performed in the rotary pump chip. Fluorescence was measured in situ at various time points as the PCR reaction mixture was pumped through different temperature regions. A fragment of the ft-actin gene was amplified from human male genomic DNA. The closed circles represent data from an experiment which contained the human template DNA. The open circles represent data from a negative control experiment in which template DNA was withheld.

Amplification of purified nucleic acid samples in accordance with embodiments of the present invention is not limited to the specific microfluidic structure shown in FIG. 34. Alternative, more complex microfluidic geometries are possible. In accordance with one alternative embodiment, a microfluidic architecture comprising a matrix of reaction chambers would allow n DNA samples to react with m primer pairs, thereby allowing m×n reactions to be performed simultaneously.

Figure 36A:
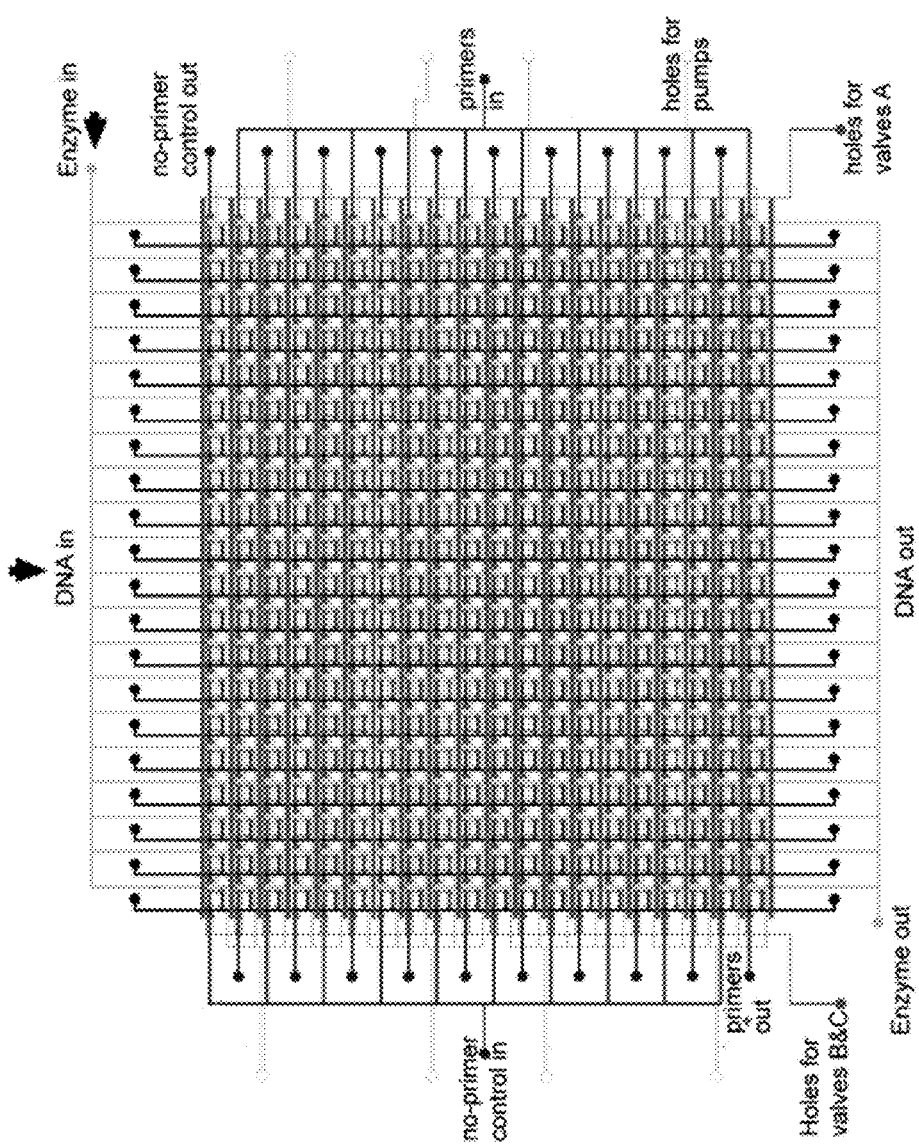
FIG. 36A shows a plan view of a matrix PCR architecture.
Figure 36B:
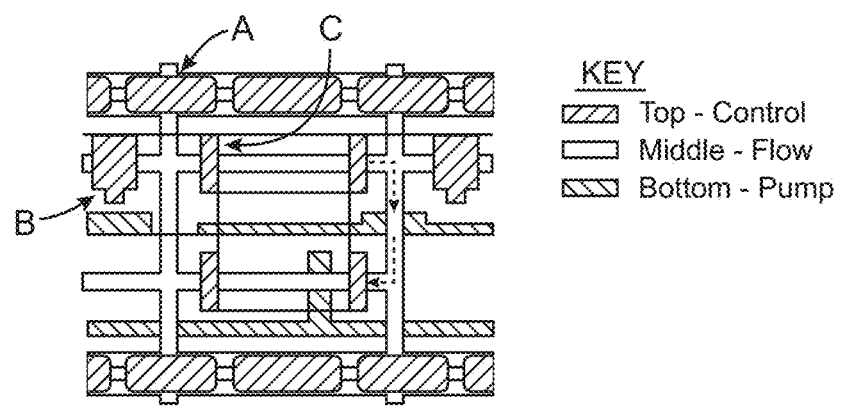
FIG. 36B shows an enlarged view of one cell of the matrix PCR architecture of FIG. 36A.

FIG. 36A shows a plan view of a matrix PCR architecture. FIG. 36B shows an enlarged view of one cell of the matrix PCR architecture of FIG. 36A. A complete description of the matrix PCR microfluidic architecture shown in FIGS. 36A-B is described in U.S. provisional patent application No. 60/494,432, incorporated by reference herein for all purposes.

As shown in the schematic layout of FIGS. 36A-B, the device comprises three layers having distinct functions. A middle matrix flow channel structure is sandwiched between a top layer comprising integrated hydraulic valves, and a lower layer comprising and pneumatic pumps. In the middle layer, the microfluidic flow channels are 106 µm wide and 12 14 µm high. Each vertex of the matrix contains a rectangular-shaped channel comprising a reactor, having a volume of ~3 nL.

Each row of reactors is connected to a separate input port (~625 µm in diameter) through which unique primers may be loaded. Each column can similarly load the reactors with different DNA templates. A single input for the addition of polymerase is connected to all the reactors in the matrix.

In the upper control layer, the valve system is designed to load each reactor with the three separate reagents while preventing cross contamination. In total, 2860 valves displayed horizontally or vertically are controlled by only 2 independent pressure supply through holes. Furthermore, the large valves (B in the inset of FIG. 36, 270 µm wide) or the small valves (C, 96 µm wide) can be selectively actuated because they have a different threshold of hydraulic pressure necessary for actuation.

Reagent loading is not blocked by the narrow control channels (42 µm wide) connecting the valve system because their tiny membrane does not deflect at the actuation pressure used. The second, bottom control layer comprises a 20×20 array of rotary pumps in order to facilitate mixing the reagents.

Active valves in the upper control layer facilitate the loading and isolation of reagents. With valves A actuated, primer sets are loaded along each row of the matrix. Actuation of valves B and C isolates a well defined volume of primers in each reactor.

Valves A are then opened to allow for the loading of DNA templates down each column, while polymerase is simultaneously introduced to all reactors from a single inlet. Valves A are once again actuated, defining the desired volumes of polymerase and templates and isolating each reactor.

The different membrane areas of valves B and C allow for the selective opening of valve C by reducing the actuation pressure from 260 to 110 kPa, thus bringing all three components into fluidic contact within each reactor. Peristaltic pumps in the bottom layer allow for the rapid rotary mixing of all reagents within the reactors.

A matrix PCR microfluidic device design as shown in FIGS. 36A-B represents an advance in addressing issues relating to interfacing nanofluidic chips to the macro world, because the DNA template and primer samples are partitioned m and n fold, respectively on the chip. Furthermore, the polymerase, which is often the most expensive part of the sample, is partitioned by a factor of m×n. The design scales in a straightforward way, allowing fabrication of microfluidic devices where n=20 and m=20, yielding 400 simultaneous reactions.

5. Ligation of Nucleic Acid

Figure 33:
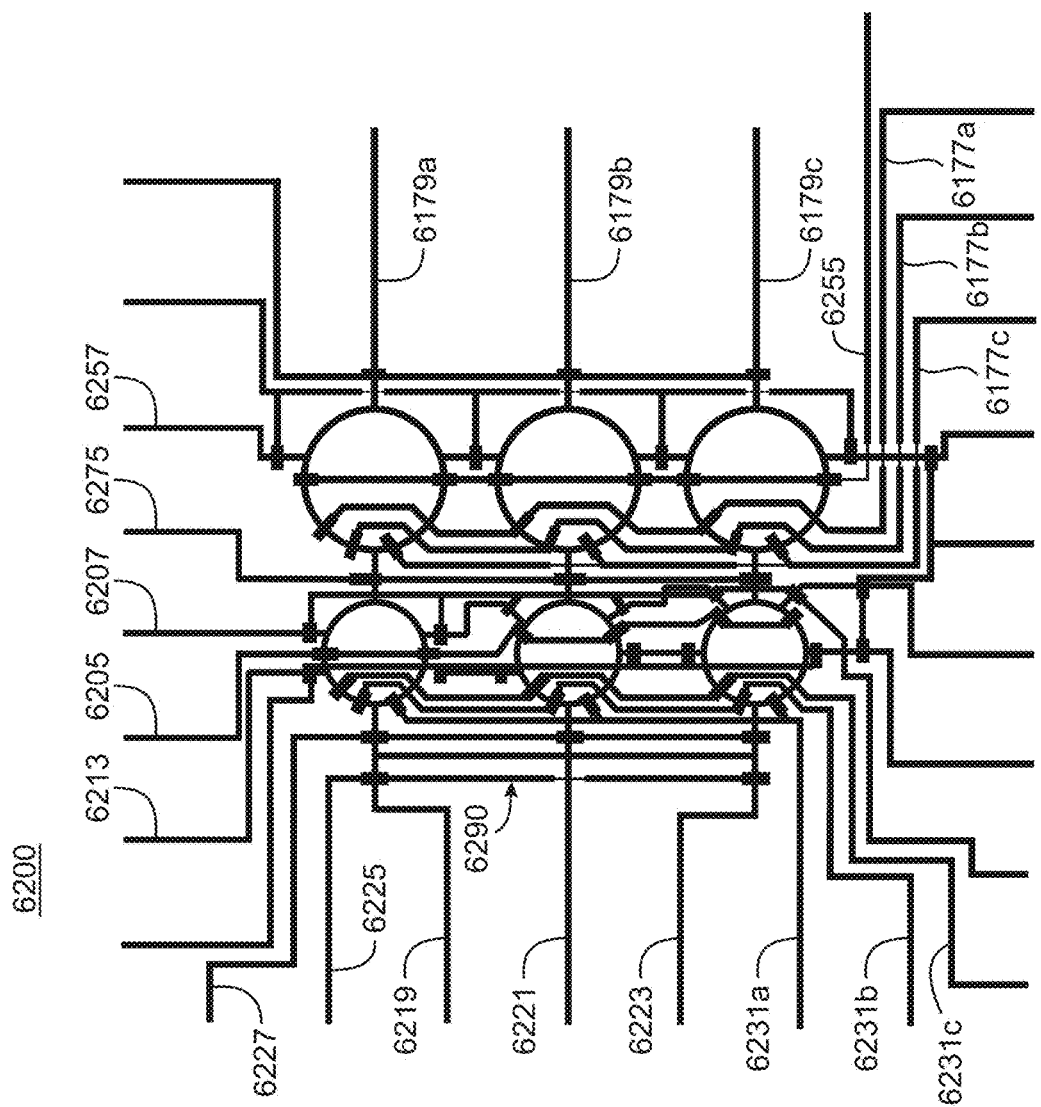
FIG. 33 shows a plan view of one embodiment of a microfluidic architecture in accordance with the present invention allowing ligation of purified nucleic acid, and transformation of cells with the ligated nucleic acid.

Once nucleic acid has been purified, it may be incorporated within a cell and then expressed. The first step of such an expression process is to ligate the nucleic acid within a host vector such as a plasmid. FIG. 33 shows a plan view of one embodiment of a microfluidic architecture suitable for such ligation and expression of purified nucleic acid. The microfluidic structure 6200 of FIG. 33 comprises a first set of parallel mixing structures used for ligation of nucleic acid, and a second set of parallel mixing structures used for transformation of cells with the ligated, purified nucleic acid.

Figure 33A:
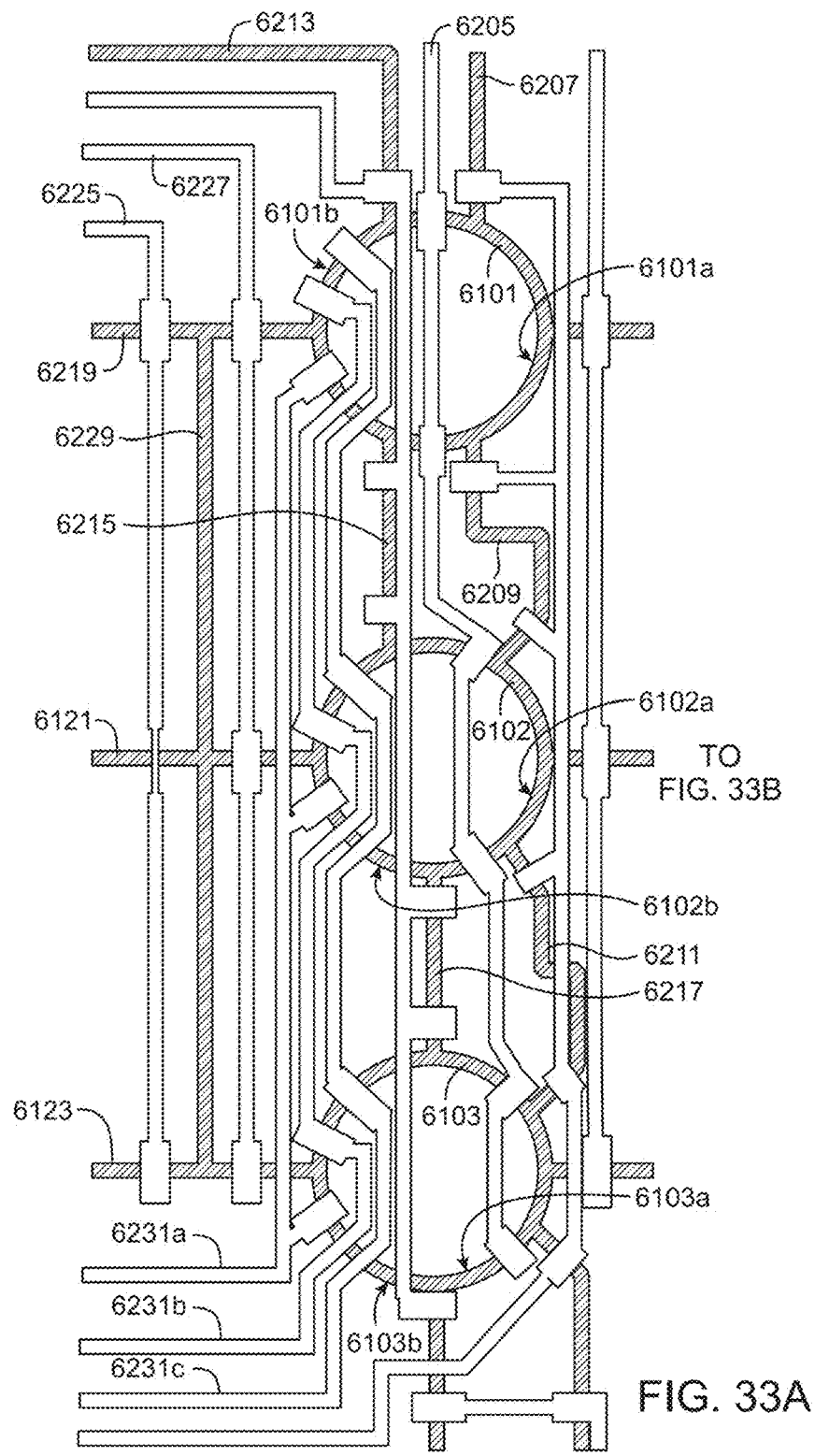
FIG. 33A shows an enlarged view of the region of the microfluidic architecture of FIG. 33 allowing ligation of purified nucleic acid.

FIG. 33A shows an enlarged view of the region of the microfluidic architecture of FIG. 33 allowing ligation of purified nucleic acid. Control line 6205 bisects each of mixing structures 6201, 6202, 6203, creating fluidly isolated hemispheres. First hemisphere 6201a of mixing structure 6201 is in fluid communication with inlet flow channel 6207. First hemisphere 6202a of second mixing structure 6202 is in fluid communication with first hemisphere 6201a of first mixing structure 6201 through linking flow channel 6209. First hemisphere 6203a of third mixing structure 6203 is in fluid communication with first hemisphere 6202a of second mixing structure 6202 through linking flow channel 6211. Actuation of control line 6205 allows the host vector/plasmid to be flowed through inlet 6207 and links 6209 and 6211 into the first hemispheres of all three mixing structures.

Second hemisphere 6201b of mixing structure 6201 is in fluid communication with inlet flow channel 6213. Second hemisphere 6202b of second mixing structure 6202 is in fluid communication with first hemisphere 6201 through linking flow channel 6215. Second hemisphere 6203b of third mixing structure 6203 is in fluid communication with second hemisphere 6202b of second mixing structure 6202 through linking flow channel 6217. Actuation of control line 6205 allows purified nucleic acid mixed with ligation enzyme to be flowed through inlet 6213 and branches 6215 and 6217 into the second hemispheres of all three mixing structures.

Each of second hemispheres 6201b, 6202b, and 6203b of mixing structures 6201, 6202, and 6203 are also in fluid communication with inlet flow channels 6221 through loading structure 6290. Specifically, while control line 6227 is actuated, fluid is flowed through flow channel 6221. As a result of the closed state of the valves defined by control line 6227, the fluid flowed down channel 6221 is diverted into utilizing cross-connector flow channel 6229 and flow channels 6219 and 6223. Because flow channels 6219 and 6223 are open-ended, loading structure 6290 may thus be rapidly filled with wash or other fluid, avoiding the delay that would otherwise be necessary to dead-end load flow channel 6221.

Next, control line 6227 is deactuated, and control line 6225 actuated, such that application of pressure to flow channel 6221 results in the contents of loading structure 6290 being flowed into second hemispheres 6201b, 6202b, and 6203b of mixing structures 6201, 6202, and 6203, respectively. In the manner just indicated, inlet 6221 may be utilized to load the mixing structures with washing fluid and/or SOC media later useful during gene transformation.

Once the first and second hemispheres of mixing structures 6201, 6202, and 6203 have been loaded with the vector and ligation enzyme/purified nucleic acid respectively, control channels 6231a-c may be actuated in a systematic fashion to accomplish circulation within the mixing structures. This circulation results in the enzyme causing ligation of the purified nucleic acid within the host vector/plasmid.

6. Transformation of Cells with Nucleic Acid

The microfluidic structure 6200 of FIG. 33 also comprises a second set of parallel mixing structures 6251, 6252, and 6253 used for transformation of a cell with the ligated purified nucleic acid. FIG. 33B shows an enlarged view of the region of the microfluidic architecture of FIG. 33 allowing cell transformation with the ligated purified nucleic acid.

The microfluidic architecture employed for cell transformation is similar to that used for nucleic acid ligation. Specifically, the three parallel mixing structures 6251, 6252, and 6253, are bisected by a control line 6255, creating fluidly isolated hemispheres. First hemisphere 6251a of mixing structure 6251 is in fluid communication with inlet flow channel 6257. First hemisphere 6252a of second mixing structure 6252 is in fluid communication with first hemisphere 6251a of first mixing structure 6251 through linking flow channel 6259. First hemisphere 6253a of third mixing structure 6253 is in fluid communication with first hemisphere 6252a of second mixing structure 6252 through linking flow channel 6261. Actuation of control line 6255 allows the host cells to be flowed through inlet 6257 and links 6259 and 6261 into the first hemispheres of all three parallel mixing structures 6151-6153.

Second hemisphere 6251b of mixing structure 6251 is in fluid communication with mixing structure 6201 through connecting flow channel 6271. Second hemisphere 6252b of mixing structure 6252 is in fluid communication with mixing structure 6202 through connecting flow channel 6272. Second hemisphere 6253b of mixing structure 6253 is in fluid communication with mixing structure 6203 through connecting flow channel 6273. Control line 6275 overlies each of the connecting flow channels 6171-6173 to define valves isolating the nucleic acid ligation region of the architecture from the cell transformation region of the architecture.

Once the first hemisphere of the mixing structures have been loaded with the cells that are to be transformed, control line 6255 is deactuated and the host vectors incorporating the ligated purified nucleic acids are flowed from first mixing structures 6201, 6202, and 6203 into second mixing structures 6251, 6252, and 6253, respectively. Control channels 6177*a-c* are actuated in a systematic fashion to accomplish circulation of the cells and host vectors within the mixing structures.

Upon application of a heat shock to the contents of the second mixing structures, the cells incorporate the vector and the purified nucleic acid present therein. Such a heat shock may be applied across the entire fluidic chip, or alternatively may be applied only locally to the second mixing structures utilizing small temperature control structures fabricated for that purpose.

7. Culturing Transformed Cells

Once cells within the second mixing structures have been exposed to heat shock and thereby incorporated the host vector containing the purified nucleic acid, they may be flowed from outlet flow channels 6179*a-c* for culturing. In accordance with one embodiment, the transformed cells could be removed from the chip for culturing. Alternatively, culturing of the transformed cells could take place directly on-chip in cell pen or cage structures described above.

The cultured and transformed cells would be expected to express the purified nucleic acid present in the incorporated vector. As described above in connection with an alternative approach to cell isolation, the cultured transformed cells could be sorted by an additional microfluidic structure. This sorting could be based upon the physical characteristics of the transformed cells resulting from their expression of the purified nucleic acid.

8. Applications for Bacterial/Viral Nucleic Acid

Evolutionary Variation: cells->gDNA->PCR->recover DNA

One application for nucleic acid purification in accordance with the present invention is to study evolutionary variation in a restricted set of genes. Evolutionary relationships are currently deduced mainly on the basis of either ribosomal RNA or whole genome comparisons, when available. In accordance with embodiments of the present invention, a microfluidic manipulation of a sample may allow proportional measurement of the distribution of mutations for selected genes in bacteria not able to be cultured. The microfluidic architecture may isolate a single bacterium from a sample, lyse that bacterium, and then purify the genomic DNA from the bacterium. The microfluidic architecture may then amplify a selected gene (or set of genes) using PCR. The amplified material can be recovered from the chip, re-amplified, and sequenced.

gDNA cloned library: cells->gDNA->digestion->gDNA library

In accordance with another embodiment in accordance with the present invention, a cloned library of genomic DNA may be created from a single or small number of bacteria. Individual bacteria from a diluted sample can be distributed into microfluidic chambers. The bacteria are then lysed, the genomic DNA purified, digested, and then ligated into cloning vectors. These vectors will then be transformed into *E. coli* using heat shock and mixing as described in connection with FIG. 33.

A vector allowing an average insert size in the range 1-2 kbp may be used. The gDNA libraries can be recovered and analyzed using conventional genomic methods. The gDNA library can be characterized by hybridization to a microarray, or representative sequencing. Cloning efficiency can be measured and evaluated.

Cloned BAC Library: cells->gDNA->digestion->BAC library

In accordance with still other embodiments of the present invention, microfluidic architectures can be used to make a cloned bacterial artificial chromosome (BAC) library of genomic DNA from a single or small number of bacteria. These BAC libraries offer the advantage of having much larger average insert sizes, on the order of ~200 kbp.

Individual bacteria can be distributed into chambers on the chip. The isolated bacteria can then be lysed, and the resulting genomic DNA purified, digested, and then ligated into cloning vectors. These vectors will then be transformed into *E. coli*. Vectors and reagents to construct the BACs can be supplied from known sources. The resulting BAC libraries can be recovered from the chip and analyzed using conventional genomic methods. The recovered BAC library can be characterized by end sequencing. The cloning efficiency will be measured and evaluated.

Using a BAC library offers the advantage of preserving gene order, making reassembly easier. As in prior whole genome sequencing efforts, having both long and short insert libraries may be useful in achieving the most complete possible genome assemblies.

Characterization of Microbial Diversity

For over a century termite gut contents had been cited as being excellent sources for the microscope-viewing of abundant and morphologically diverse spirochetes. Spirochetes are an ultrastructurally distinct and genetically coherent, phylum-level assemblage of prokaryotes. Although prevalent in the guts of many termites (sometimes accounting for as much as 50% of the direct counts), they also had the reputation for "not being cultivable". However, Leadbetter et al. have amassed a 9 strain collection from the hindgut contents of the California Dampwood Termite, *Zootermopsis angusticollis*, The first 2 isolates obtained, ZAS-1 and ZAS-2, have been shown capable of $H_2+CO_2$ acetogenesis. In addition to being the first representative termite gut isolates, these were the first in the phylum Spirochetes shown to be capable of chemolithotrophic metabolism. Additionally, this was the first demonstration of $H_2+CO_2$-acetogenic catabolism by any microbe not belonging to the phylum Firmicutes, class Clostridia.

Much can be learned about the function of the uncultivated microbial diversity of the *Zootermopsis* hindgut. Leadbetter et al. obtained a molecular inventory of the bacterial community diversity of the hindgut. Different species of bacteria in a sample may have differences in their cell masses, surface areas, and rates of activity. Further complicating matters, different bacterial species may have anywhere from a single to over a dozen rRNA genes encoded on their genome. This makes it difficult to correlate gene abundance in a sample (as assessed by amplifying from the DNA) with that of the active biomass (which manifests itself as total rRNA content) of those organisms encoding them.

In order to gain a better understanding of the active microbiota in the gut, cell volume, activity, and 16 s gene copy number were "normalized" by deriving a molecular inventory from the rRNA itself. RNA purification (from total gut nucleic acids) and RT-PCR were used to construct a cDNA template, from which an inventory was subsequently amplified and cloned.

This inventory focused on the recovery of bacterial sequences using all-Bacteria primers, and thus does not yet include protozoal or archaeal representatives. About 200 full 16s rRNA sequences were cloned and RFLP-sorted, identifying approximately 50 unique ribotypes. Over 20% of the clones recovered corresponded to an unknown microbe belonging to a deeply divergent bacterial lineage, "Leptospirillum and relatives". The only studied microbes belonging to this phylum are 1) extreme acidophiles that live by oxidizing iron, 2) aerobes that live by oxidizing nitrite, or 3) thermophiles that respire sulfate to sulfide.

However, knowing the phylogeny of this microbe reveals little of its physiology or function. No niche in any animal gut for any microbe with any of such catabolism is known, and yet potentially a fifth of the active microbial biomass in the termite hindgut, as deduced from the results of the inventory, is from a microbe related to these with such catabolism. Because of the deduced abundance of these bacteria, they become excellent candidates for exploring the efficacy and impact of cell sorting and further in depth analysis vis a vis nanofluidic devices.

Microbial diversity in the human gut can also be characterized using the gDNA chips previously discussed. The following model can be used to estimate the quality of data expected from such experiments. Suppose libraries are created from a population of 1,000 individual bacteria, and that this population is made up of roughly 100 species, each of which occurs 10 times. Further assume that each bacterial genome is 1 mega base pair and that the average insert size is 1 kilo base pair. If the gDNA chip were to clone with 100% efficiency, the resulting libraries would have 10× coverage of each of the 100 bacterial species. Assuming a more realistic figure of 10% efficiency, then each species would have on average 1× coverage.

For any given species this coverage is spread over 10 different libraries, without any a priori knowledge which 10 out of the 1,000 libraries this is. This leads to the natural question of, if when the libraries are completely sequenced, whether there will be enough overlap between the libraries to link them together as belonging to the same species.

A simple calculation using the above figures shows that the probability of not being able to link any pair of libraries is roughly $e^{-20}$. Thus, after completely sequencing each library, any given library should be able to be associated with another originating from the same species. This allows complete deconvolving of the library data and reconstruction of the microbial diversity of the sample.

Thus in the hypothetical example given above, if the average sequencing read length was 500 base pairs, and all the bacterial genomes were unknown, then 200,000 sequencing lanes per experiment would be required (i.e. per 1,000 bacteria). In practice, resequencing of known genomes would be halted as soon as they are identified, which should be after a small number of sequencing lanes.

An alternative set of experiments would explore incorporation of a cell sorting component into the front end of the gDNA chip just described. Antibody markers and FACS would be used to enrich the population for unknown bacteria, thereby allowing sorting of known species into the waste channel, and collecting the unknown bacteria.

Many of the gut microbes have distinct and differing morphologies. This will make it reasonably straight forward to identify and collect a significant sample of the genetic diversity that underlies the morphological. BAC libraries of genomic DNA of collected individuals will be constructed. After this, clones from each BAC library will be screened with primers designed to specifically amplify only the rRNA encoding gene of the not-yet-cultivated leptospirillum-relative identified earlier during our 16S rRNA molecular inventory.

Once identified, not only the BAC clones containing single genomic DNA fragments encoding the rDNA will be retrieved, but also libraries of the entire or near entire genome of the cells with that ribotype.

Microbial Ecology

Microbial ecology is an emerging field of study that explores the relationship between specific environments and the biological entities existing therein. Investigation of the properties and genetic makeup of such environmental biological entities can offer tremendous benefits, as exemplified by the discovery of antibiotic properties of the penicillin mold existing in the environment.

Fortuitously, penicillin proved amenable to laboratory cultivation, and its antibiotic properties were able to be investigated and harnessed. However, a relatively large percentage of bacterial cells and other biological entities from the environment have so far resisted laboratory cultivation. The continuing inability to reproduce these environmental biological entities under controlled conditions has so far precluded access to their genetic information and metabolic potential, limiting investigations of microbial ecology.

In an attempt to glean information regarding not-yet-cultivated biological entities present in specific ecological or clinical environments, many researchers have turned to metagenomics. In metagenomics, samples comprising highly complex heterogeneous mixtures of biological entities are collected from an environment. Biological entities present within the samples are disrupted en masse, and the resulting nucleic acid and genetic information contained therein is processed first as a single unit—a "meta" genome corresponding to an entire environment rather than to a specific organism. Examples of recent metagenomic investigations include Lorenz et al., "Screening for novel enzymes for biocatalytic processes: accessing the metagenome as a resource of novel functional sequence space", J. Curr Opin Biotechnol. 2002 December; 13(6):572-7, and Rondon et al., "Cloning the soil metagenome: a strategy for accessing the genetic and functional diversity of uncultured microorganisms.", Appl Environ Microbiol. 2000 June; 66(6):2541-7, both of which are incorporated by reference herein for all purposes.

While metagenomics shows some promise for microbial ecology investigations, it offers some serious drawbacks. One drawback of metagenomics approaches is dissolution of the link between the genetic information obtained (i.e. the nucleic acid), and the origin of that information (i.e. the biological entity containing the nucleic acid). This link between information and source can be reconstructed from the morass of community biocomplexity only at great effort, if at all. Thus using such metagenome approaches, it has only been straightforward to identify the genes as being from the same biological entity if they co-locate on the same BAC genome fragment. The remainder of the genomic library for that species is lost into a vast, unsortable BAC mixture produced by en masse disruption of all biological entities or components present in the highly heterogeneous environmental or clinical sample.

By contrast, microfluidic techniques in accordance with embodiments of the present invention offer a promising alternative to metagenomic approaches. Specifically, microfluidic methods and structures enable physical isolation of individual or small numbers of biological entities within a larger sample. Subsequent purification of nucleic acid present within the individual or subset of biological entities can readily be linked to morphotypic, ribotypic, and genotypic information obtained from the physically isolated biological entity or entities. This contrasts with the metagenome approach to cloning, in which total community environmental DNA is restricted and cloned into a BAC library. A net sequencing of a microbial community is achieved utilizing both metagenomic and microfluidic techniques, but only in the latter approach is informational coherence of individual genomes maintained.

9. Applications for Non-Bacterial Nucleic Acid

The foregoing description has so far focused upon applications for purification of nucleic acid from bacteria or viruses. However, the present invention is not limited to this particular application, and in accordance with alternative embodiments, nucleic acids from mammalian or other non-bacterial cell types may be purified utilizing microfluidic approaches, as discussed in detail in U.S. provisional patent application No. 60/494,388, filed Aug. 11, 2003 and incorporated by reference herein for all purposes.

cells->mRNA->cDNA->Taqman PCR in Matrix

In accordance with one embodiment, a microfluidic chip can be designed to take a small number of cells (from 1 to 1,000), lyse them, purify mRNA, create cDNA, and detect the presence of specific transcripts using Taqman PCR in a matrix geometry. Such a microfluidic architecture can be used to optimize the parameters of mRNA purification and cDNA synthesis.

Components for cell lysis, bead trapping, affinity purification, and Taqman PCR may be combined in order to purify and detect expression of selected genes. The number of cells used to produce cDNA may be systematically varied, and the results compared from large numbers used in conventional macroscopic techniques to chip-based results using 1,000 cells, 100 cells, 10 cells, and 1 cell. Such a comparison would allow understanding of the effects of cell number stochasticity, and determination of the number of cells needed to make reliable measurements of medium and low copy number mRNA.

An advantage of such a microfluidic design is that it will allow direct measurement of cDNA production efficiency without introducing further losses in the cloning process. A well characterized cell line, such as NIH MGC 53 or NIH MGC 93, for which there is extensive EST and microarray data, could be used for these experiments. Using a cell line instead of tissue will control for possible bias in the results from unidentified sub-populations in a heterogeneous sample. Validation may be done by comparing chip results to both conventional results obtained manually, and to results listed in the NIH EST database (10,000 clones sequenced).

cells->mRNA->cDNA->RNA->Microarray

In another application, a microfluidic chip could be designed to take a small number of cells (from 1 to 1,000), lyse them, purify mRNA, create cDNA with a T7 promoter, and then use T7 RNA polymerase to make linearly amplified, fluorescent RNA which can then be hybridized to a microarray. The microarray may be fabricated in situ onto the chip using methods similar to the surface derivatization previously demonstrated for surface biotinylation.

Such a chip architecture would provide a more stringent test of cDNA quality than the first variation since the amplification stage is linear. Validation can be performed by comparing to DNA microarray data obtained by conventional methods. Again, use of a cell line will control for unidentified subpopulations. Possible applications for such a microfluidic architecture include tumor typing, clinical diagnosis, prediction of treatment outcome, and developmental biology.

cells->mRNA->cDNA->Differential Cloned Library

In still another application, a microfluidic chip may be designed to construct a library of cDNA clones from a small number (from 1 to 1,000) of cells. Such a chip may use the methods of the original cDNA chip in order to construct the library.

In this application, however, two cell populations will be processed in parallel, and before cloning the libraries will be normalized against each other. Such a chip architecture can be validated using two cell lines for which conventional techniques can be used. The resulting library elements can be sequenced.

Hematopoietic Stem Cell Studies

The pluripotent hematopoietic stem cells (PHSC) are a rare population of cells that reside in the bone marrow and that maintain the dynamics of the blood system. Following intrinsic characteristics and environmental influences, these cells will move into one of the following pathways: self renewal as primitive stem cells, maturation into differentiated hematopoietic cells, or apoptosis. In adult bone marrow, a balance among these three pathways is maintained in order to provide normal hematopoiesis.

Based on the limited dilution competitive repopulation assay, the frequency of PHSC in bone marrow is approximately 1 in 100,000 nucleated cells. Isolation of PHSC is a necessary step in studying their function.

The most reliable method in the field to isolate PHSC is to use FACS sorting using a variety of cell membrane surface proteins as markers. Purified mouse PHSC has been obtained by developing a 5 color FACS sorting system using a 3 laser MoFlo Cytometer with Summit data analysis software (other investigators use 3 color sorting based on a three surface protein expression profile; several groups can do 4 color sorting).

With this 5 color system, bone marrow cells were labeled with 5 different antibodies (lineage markers cocktail, anti Sca 1, anti c kit, antiCD38 and anti CD34) conjugated with different fluorochromes. The most primitive hematopoietic stem cells are characterized by the surface expression profile: LinSca 1+ kit+ CD38+ CD34 (abbreviated as +++− cells). These cells (called long term repopulating cells, LTRC) were shown to provide long term repopulation of the blood system in lethally irradiated mice.

FIGS. 41A-B show flow cytometric analysis of the surface marker expression profile of murine bone marrow cells. Lineage-positive cells were removed by CS column before flow cytometry. FIG. 41A shows expression of Sca 1 and c kit on the cell surface was gated as shown; Lin−Sca+kit+ cells were gated as shown in the box A.

FIG. 41B shows expression of CD38 and CD34 on the cell surface of the Lin−Sca+kit+cells was used to separate the subpopulation shown in box A of the left figure into the following 4 subsets: Sca+kit+CD38+CD34, Sca+kit+CD38+CD34+, Sca+kit+CD38−CD34+, and Sca+kit+CD38−CD34−. Cells in each population were sorted and collected for analysis in a repopulation assay. Based on FIGS. 41A-B, the frequency in bone marrow nucleated cells was shown to be 2 in 100,000 nucleated cells.

Further analysis indicated that the physiological pathway appears to be: +++− cells differentiate next into ++++ cells (Lin Sca 1+ kit+ CD38+ CD34+) and then into ++−+ cells (Lin Sca 1+ kit+ CD38−CD34+). Both ++++ and ++−+ cells belong to the category of short term repopulating cells (STRC), since they can only repopulate a lethally irradiated mouse for a number of weeks, not for the normal lifetime of the animal. However, both LTRC and STRC are needed to rescue a lethally irradiated recipient effectively.

From the above observations, the hypothesis of PHSC regulation is modeled as following. FIG. 42 illustrates a proposed regulatory network for murine pluripotent hematopoietic stem cells. As illustrated, signals (positive and/or negative) between these three bone marrow subsets regulates the balance of cells within the stem cell compartment in the bone marrow, thereby controlling hematopoiesis. Preliminary evidence has been obtained to support the partial regulatory network shown in FIG. 42.

Understanding the regulatory mechanisms that control hematopoiesis in the human should make it possible to manipulate the system in vivo. Such control would have a broad range of clinical applications, including in cancer therapy, treatment of blood diseases, genetic disorders, as well as stem cell gene therapy.

One of the approaches for gaining an insight into the regulation of hematopoiesis is to identify the genes that are specifically expressed at each stage of cell maturation and then to determine their function in the hematopoietic pathway. Genes that were specifically expressed in +++– cells, while not being expressed in ++++ or ++–+ cells, i.e., were identified to determine those genes that specifically provide an LTRC phenotype.

Specifically, using differential display PCR (DD PCR), 184 gene transcripts were identified from a total of 1395 DD PCR fragments, as significantly elevated or uniquely expressed in +++– cells, compared with ++++ and ++–+ cells. These 184 gene fragments were confirmed by reverse northern blots, subcloned, and sequenced.

Three known data bases, Genbank, EST (expression sequenced tag), and stem cell data base from Princeton university (developed by Ihor Lemishka), were screened. Seventy-two of the genes (39%) exhibited homology to genes with known function. Fifteen genes (8%) exhibited homology to sequences in the EST data base.

Ninety-seven genes (53%) appear to be novel, i.e., they do not have homology to any sequence in the three examined databases. The Celera database can be screened for these "unknown" genes. To obtain the full length version of these "unknown" genes, a commercial 17 day mouse embryo cDNA library was first screened. However, only 10.1% of the genes gave a positive signal in a PCR reaction.

The embryo cDNA library was derived from a mixture of cell types. Consequently, low expression transcripts from any single cell type would be buried in the background.

Accordingly, two cDNA libraries were constructed using whole mouse bone marrow as a starting point: one library was from "low density cells" and the second from "lineage negative" cells. Rather than needing approximately $1 \times 10^8$ cells as required for commercial cDNA library preparations, by scaling down each step, reasonable libraries with $1 \times 10^{4-5}$ cells have been obtained.

The low density cell and lineage negative cell cDNA libraries were constructed with the technology developed by Clontech and Gibco BRL, respectively. A tracer of radioactivity (32P dCTP) was used in an aliquot from each library construction to measure 1" and 2" a strand synthesis efficiency.

Twelve random clones were picked, and DNA was prepared followed by restriction enzyme digestion. The average size of the insert was 1.5 kb (with an insert size range of 0.8 kb to 3.1 kb) for the low density cell library and an average of 2.2 kb for the lineagenegative cell library, respectively. However, a total of 109 and 108 cells were required, respectively.

Comparing the positive PCR reactions using the "unknown" gene fragments for each of the three cDNA libraries, the observed frequency of positives was highest in the lineage negative cell cDNA library: 30%, lineage negative library; 18%, low density library; 10%, commercial 17 day embryo library. Nonetheless, +++– cells are still a relatively rare population even in the lineage negative library (50 in 100,000 cells). Seventy of the genes remain missing.

The appropriate resolution would be to construct a cDNA library from +++– cells. However, obtaining $1 \times 10^5$ +++– cells would be a very difficult task. Approximately 200+++– cells can be obtained from one mouse. Obtaining $1 \times 10^5$ +++– cells would require, therefore, harvesting bone marrow cells from 500 mice, a logistically impossible task for an academic laboratory. Furthermore, even 5 color sorting does not provide a pure population of cells.

Accordingly, production of a cDNA library on a chip from 1 or only a few cells in accordance with embodiments of microfluidic approaches in accordance with the present invention, would address both problems. Specifically, use of microfluidics would involve only a limited number of cells, and would result in relatively pure material due to the reduction of a mixture of cells in any population of primary cells.

While the above description has focused upon the use of microfluidic architectures for isolation and purification of nucleic acids from viruses, bacteria, and multi-cellular organisms, the present invention is not limited to this particular application. In accordance with alternative embodiments, components of biological entities other than nucleic acids may be recovered and purified using the present invention. For example, proteins present within a virus, bacteria, or cell may be exposed through lysis, and then recovered and analyzed and/or purified in accordance with embodiments of the present invention.

And while the above description has focused upon microfluidic architectures which combine the isolation of components of viruses, cells, or bacteria, with purification of the isolated components, this is not required by the present invention. In alternative embodiments, isolation and lysis of one or a subset of biological entities from a sample may be followed immediately by analysis, without necessarily requiring an intervening purification step.

Such alternative embodiments may be particularly valuable where microfluidic isolation of only one or a small number of biological entities has been achieved, reducing the overall complexity of the resulting lysed mixture. Such alternative embodiments may also prove valuable where mixtures are analyzed utilizing techniques highly sensitive to a specific target present therein.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth. Therefore, many modifications may be made to adapt a particular situation or material to the teachings of the invention without departing from the essential scope and spirit of the present invention. It is intended that the invention not be limited to the particular embodiment disclosed as the best mode contemplated for carrying out this invention,

What is claimed is:

1. A microfluidic apparatus comprising:
   (a) a solid substrate;
   (b) a cell separation and processing system embedded in the substrate that includes an arrangement of flow channels configured so that individual cells from a cell population can be singly isolated;
   (c) one or more inlet channels in the substrate connected with the cell separation and processing system so that a reagent can be delivered through the inlet channel(s) and combined with cells isolated by the system; and
   (d) one or more outlet channels in the substrate connected with the cell separation and processing system so that contents obtained by lysing isolated cells can be flowed through the outlet channel(s) and kept separate;
   wherein the apparatus is designed and constructed so that a user can prepare a plurality of cDNA libraries from single cells by a method that comprises:
   (1) receiving a sample of cells into the cell separation and processing system of the apparatus;
   (2) processing the sample in the cell separation and processing system such that a plurality of single cells from the sample are fluidically isolated from all other cells in the sample, thereby producing isolated single cells;
   (3) combining a lysing chemical or buffer with the isolated cells such that mRNA is liberated from each of at least some of the isolated single cells in a manner that keeps the mRNA from each of the isolated single cells separate; and
   (4) reverse transcribing and amplifying the mRNA liberated in step (3) such that a separate cDNA library is formed from at least some of the isolated single cells; thereby producing said plurality of cDNA libraries from single cells.

2. The microfluidic apparatus of claim 1, wherein the method further comprises:
   (5) flowing the separate cDNA libraries through the outlet channel(s) of the apparatus and keeping separate at least some of the cDNA libraries formed in step (4).

3. The microfluidic apparatus of claim 1, wherein step (2) and step (3) are performed separately.

4. The microfluidic apparatus of claim 1, wherein the cell separation and processing system is configured to singly isolate cells from the cell population by way of a plurality of valves in the system that are operable to close channels between single cells.

5. The microfluidic apparatus of claim 1, wherein the cell separation and processing system is configured to singly isolate bacteria.

6. The microfluidic apparatus of claim 1, wherein the cell separation and processing system is configured to singly isolate eukaryotic cells.

7. The microfluidic apparatus of claim 1, further comprising one or more mixing structures configured to actively mix a lysing agent delivered through the inlet channels with cells singly isolated by the cell separation and processing system.

8. The microfluidic apparatus of claim 7, wherein the one or more mixing structures are rotary mixers.

9. The microfluidic apparatus of claim 1, wherein step (3) comprises operating the apparatus so as to actively mix the lysis chemical or buffer with the single cells.

10. The microfluidic apparatus of claim 1, wherein step (3) comprises operating the apparatus so as to diffusively mix the lysis chemical or buffer with the single cells.

11. The microfluidic apparatus of claim 1, configured for sequence analysis of cDNA libraries from the single cells.

12. A microfluidic apparatus comprising:
   (a) a solid substrate;
   (b) a cell separation and processing system embedded in the substrate that includes an arrangement of flow channels configured so that individual cells from a cell population can be singly isolated;
   (c) one or more inlet channels in the substrate connected with the cell separation and processing system so that a reagent can be delivered through the inlet channel(s) and combined with cells isolated by the system; and
   (d) one or more outlet channels in the substrate connected with the cell separation and processing system so that contents obtained by lysing isolated cells can be flowed through the outlet channel(s) and kept separate;

wherein the apparatus is designed and constructed so that a user can prepare a plurality of nucleic acid libraries from single cells by a method that comprises:

(1) receiving a sample of cells into the cell separation and processing system of the apparatus;

(2) processing the sample in the cell separation and processing system such that a plurality of single cells from the sample are fluidically isolated from all other cells in the sample, thereby producing isolated single cells;

(3) combining a lysing chemical or buffer with the isolated cells such that nucleic acid is liberated from each of at least some of the isolated single cells in a manner that keeps the nucleic acid from each of the isolated single cells separate; and (4) amplifying the nucleic acid liberated in step (3) such that a separate nucleic acid library is formed from at least some of the isolated single cells;

thereby producing said plurality of nucleic acid libraries from single cells.

13. The microfluidic apparatus of claim 12, wherein the method further comprises:

flowing the separate nucleic acid libraries through the outlet channel(s) of the apparatus and keeping separate at least some of the nucleic acid libraries formed in step (4).

14. The microfluidic apparatus of claim 12, wherein step (2) and step (3) are performed separately.

15. The microfluidic apparatus of claim 12, wherein the cell separation and processing system is configured to singly isolate cells from the cell population by way of a plurality of valves in the system that are operable to close channels between single cells.

16. The microfluidic apparatus of claim 12, further comprising one or more mixing structures configured to actively mix a lysing agent delivered through the inlet channels with cells singly isolated by the cell separation and processing system.

17. The microfluidic apparatus of claim 16, wherein the one or more mixing structures are rotary mixers.

18. The microfluidic apparatus of claim 12, wherein step (3) comprises operating the apparatus so as to actively mix the lysis chemical or buffer with the single cells.

19. The microfluidic apparatus of claim 12, wherein step (3) comprises operating the apparatus so as to diffusively mix the lysis chemical or buffer with the single cells.

20. The microfluidic apparatus of claim 12, configured for sequence analysis of nucleic acid or cDNA libraries from the single cells.

* * * * *